(12) United States Patent
Kaseko et al.

(10) Patent No.: US 9,752,128 B2
(45) Date of Patent: Sep. 5, 2017

(54) METHODS OF GENERATING CELLS EXHIBITING PHENOTYPIC PLASTICITY

(75) Inventors: Galina Kaseko, Waverley (AU); Tohsak L. Mahaworasilpa, Kingsford (AU)

(73) Assignee: Stephen Sanig Research Institute Ltd., Eveleigh (AU)

( * ) Notice: Subject to any disclaimer, the term of this patent is extended or adjusted under 35 U.S.C. 154(b) by 0 days.

(21) Appl. No.: 13/377,296

(22) PCT Filed: Jun. 10, 2010

(86) PCT No.: PCT/AU2010/000716
§ 371 (c)(1),
(2), (4) Date: Apr. 3, 2012

(87) PCT Pub. No.: WO2010/141990
PCT Pub. Date: Dec. 16, 2010

(65) Prior Publication Data
US 2012/0088304 A1   Apr. 12, 2012

(30) Foreign Application Priority Data
Jun. 10, 2009   (AU) ................ 2009902649

(51) Int. Cl.
*C12N 5/16* (2006.01)
*C12N 5/078* (2010.01)
(52) U.S. Cl.
CPC ............. *C12N 5/16* (2013.01); *C12N 5/0634* (2013.01)
(58) Field of Classification Search
CPC ................................ C12N 5/16; C12N 5/0634
See application file for complete search history.

(56) References Cited

U.S. PATENT DOCUMENTS

| | | | |
|---|---|---|---|
| 8,778,677 B2 | 7/2014 | Kaseko et al. | |
| 2004/0234519 A1 | 11/2004 | Tso et al. | |
| 2007/0154995 A1* | 7/2007 | Trakht | 435/70.21 |
| 2012/0088272 A1 | 4/2012 | Kaseko et al. | |

FOREIGN PATENT DOCUMENTS

| | | |
|---|---|---|
| EP | 0 292 965 A2 | 11/1988 |
| EP | 0 850 952 A1 | 7/1998 |
| EP | 1 167 537 A1 | 1/2002 |
| JP | S64-60373 | 3/1989 |
| JP | 02-186982 | 7/1990 |
| JP | H08-84596 | 4/1996 |
| JP | H11-100400 | 4/1999 |
| JP | 2000-342279 | 12/2000 |
| JP | 2007-523622 | 8/2007 |
| JP | 2008-504289 | 2/2008 |
| JP | 2008-523086 | 7/2008 |
| JP | 2009-505666 | 2/2009 |
| RU | 2116346 C1 | 7/1998 |
| WO | WO 91/16430 A1 | 10/1991 |
| WO | WO 94/26923 A1 | 11/1994 |
| WO | WO 2005/014642 A2 | 2/2005 |
| WO | WO 2006/004663 A2 | 1/2006 |
| WO | WO 2006/063168 A2 | 6/2006 |
| WO | WO 2008/013552 A2 | 1/2008 |
| WO | WO 2010/141990 A1 | 12/2010 |

OTHER PUBLICATIONS

Harada et al International Journal of Oncology, 30: 1461-1468, 2007).*
Koeffler et al Blood, 1981, 58(6), 1159-1163.*
Prohaska et al (Seminar in Immunology, 2002, 14, 377-384.*
Hering et al (Biomed. Bioochim. Acta (1988) 2, 211-216.*
Kaseko et al (BMC Proc. 2011; 5(Suppl 8): P130.*
PCT/AU2010/000716, Jul. 29, 2010, International Search Report and Written Opinion.
Ainai et al., Renewal of EBV-hybridoma method: efficient generation of recombinant fully human neutralizing IgG antibodies specific for tetanus toxin by use of tetroma cells. Hum Antibodies. 2006;15(4):139-54.
Airoldi et al., Cytokine gene expression in neoplastic B cells from human mantle cell, follicular, and marginal zone lymphomas and in their postulated normal counterparts. Cancer Res. Feb. 15, 2001;61(4):1285-90.
Blackwood et al., Going the distance: a current view of enhancer action. Science. Jul. 3, 1998;281(5373):60-3.
Boerner et al., Production of antigen-specific human monoclonal antibodies from in vitro-primed human splenocytes. J Immunol. Jul. 1, 1991;147(1):86-95.
Carothers et al., Splicing mutations in the CHO DHFR gene preferentially induced by (±)-3 alpha,4 beta-dihydroxy-1 alpha,2 alpha-epoxy-1,2,3,4-tetrahydrobenzo[c]phenanthrene. Proc Natl Acad Sci U S A. Jul. 1990;87(14):5464-8.
Christensen et al., Cell type-specific post-translational modifications of mouse osteopontin are associated with different adhesive properties. J Biol Chem. Jul. 6, 2007;282(27):19463-72. Epub May 11, 2007.
Cullen, Expression of a cloned human interleukin-2 cDNA is enhanced by the substitution of a heterologous mRNA leader region. DNA. Nov. 1988;7(9):645-50.
Durocher et al., High-level and high-throughput recombinant protein production by transient transfection of suspension-growing human 293-EBNA1 cells. Nucleic Acids Res. Jan. 15, 2002;30(2):E9.
Feizi, Demonstration by monoclonal antibodies that carbohydrate structures of glycoproteins and glycolipids are onco-developmental antigens. Nature. Mar. 7-13, 1985;314(6006):53-7.
Girard et al., 100-liter transient transfection. Cytotechnology. Jan. 2002;38(1-3):15-21. doi: 10.1023/A:1021173124640.
Gramer et al., Removal of sialic acid from a glycoprotein in CHO cell culture supernatant by action of an extracellular CHO cell sialidase. Biotechnology (N Y). Jul. 1995;13(7):692-8.
Hartmann et al., Mechanism and function of a newly identified CpG DNA motif in human primary B cells. J Immunol. Jan. 15, 2000;164(2):944-52.

(Continued)

Primary Examiner — Anoop Singh
(74) Attorney, Agent, or Firm — Wolf, Greenfield & Sacks, P.C.

(57) ABSTRACT

The present invention relates to cellular differentiation and, in particular to hybrid cells that exhibit phenotypic plasticity and methods for producing these cells. The invention also relates to methods for generating specific cells of a desired phenotype. The invention still further relates to methods of producing hybrid cells with a capacity to de-differentiate into an earlier progenitor state. The invention further contemplates the use of hybrid cells in a range of applications, for example tissue generation.

7 Claims, 18 Drawing Sheets

(56) References Cited

OTHER PUBLICATIONS

Hering et al., Raji-K562 hybrids and their use for trioma production. Biomed Biochim Acta. 1988;47(2):211-6.

Hosoi et al., Optimization of cell culture conditions for G-CSF (granulocyte-colony stimulating factor) production by genetically engineered Namalwa KJM-1 cells. Cytotechnology. Sep. 1991;7(1):25-32.

Hur et al., CD19 signalling improves the Epstein-Barr virus-induced immortalization of human B cell. Cell Prolif. Feb. 2005;38(1):35-45.

Jordan et al., Calcium-phosphate mediated DNA transfer into HEK-293 cells in suspension: control of physicochemical parameters allows transfection in stirred media. Transfection and protein expression in mammalian cells. Cytotechnology. Jan. 1998;26(1):39-47. doi: 10.1023/A:1007917318181.

Kalantarov et al., Development of a fusion partner cell line for efficient production of human monoclonal antibodies from peripheral blood lymphocytes. Hum Antibodies. 2002;11(3):85-96.

Karpas et al., A human myeloma cell line suitable for the generation of human monoclonal antibodies. Proc Natl Acad Sci U S A. Feb. 13, 2001;98(4):1799-804.

Kimura et al., Quantitative analysis of Epstein-Barr virus load by using a real-time PCR assay. J. Clin Microbiol. Jan. 1999;37(1):132-6.

Kirman et al., Isolation of native human monoclonal autoantibodies to breast cancer. Hybrid Hybridomics. Dec. 2002;21(6):405-14.

Köhler et al., Continuous cultures of fused cells secreting antibody of predefined specificity. Nature. Aug. 7, 1975;256(5517):495-7.

Li et al., Human antibodies for immunotherapy development generated via a human B cell hybridoma technology. Proc Natl Acad Sci U S A. Mar. 7, 2006;103(10):3557-62. Epub Feb. 27, 2006.

Li et al., Packaging of intron-containing genes into retrovirus vectors by alphavirus vectors. Proc Natl Acad Sci U S A. Mar. 31, 1998;95(7):3650-4.

McIlroy et al., Infection frequency of dendritic cells and CD4+ T lymphocytes in spleens of human immunodeficiency virus-positive patients. J Virol. Aug. 1995;69(8):4737-45.

Meissner et al., Transient gene expression: recombinant protein production with suspension-adapted HEK293-EBNA cells. Biotechnol Bioeng. Oct. 20, 2001;75(2):197-203.

Merika et al., Enhanceosomes. Curr Opin Genet Dev. Apr. 2001;11(2):205-8.

Miyaji et al., Efficient expression of human beta-interferon in Namalwa KJM-1 cells adapted to serum-free medium by a dhfr gene coamplification method. Cytotechnology. Sep. 1990;4(2):173-80.

Miyaji et al., Expression of human beta-interferon in Namalwa KJM-1 which was adapted to serum-free medium. Cytotechnology. Mar. 1990;3(2):133-40.

Miyaji et al., Expression of human lymphotoxin in Namalwa KJM-1 cells adapted to serum-free medium. Cytotechnology. Jul. 1990;4(1):39-43.

Parham et al., Effects of pCIneo and pCEP4 expression vectors on transient and stable protein production in human and simian cell lines. Cytotechnology. May 2001;35(3):181-7. doi: 10.1023/A:1013131415382.

Paulson et al., Tissue-specific expression of sialyltransferases. J Biol Chem. Jul. 5, 1989;264(19):10931-4.

Pham et al., Large-scale transient transfection of serum-free suspension-growing HEK293 EBNA1 cells: peptone additives improve cell growth and transfection efficiency. Biotechnol Bioeng. Nov. 5, 2003;84(3):332-42.

Satoh et al., Efficient expression of pro-urokinase by human lymphoblastoid Namalwa KJM-1 cells using moloney retroviral promoter. Cytotechnology. 1995-1996;18(3):167-72.

Satoh et al., Stable production of recombinant pro-urokinase by human lymphoblastoid Namalwa KJM-1 cells: host-cell dependency of the expressed-protein stability. Cytotechnology. 1993;13(2):79-88.

Schlaeger et al., Transient gene expression in mammalian cells grown in serum-free suspension culture. Cytotechnology. Jul. 1999;30(1-3):71-83. doi: 10.1023/A:1008000327766.

Shinkawa et al., The absence of fucose but not the presence of galactose or bisecting N-acetylglucosamine of human IgG1 complex-type oligosaccharides shows the critical role of enhancing antibody-dependent cellular cytotoxicity. J Biol Chem. Jan. 31, 2003;278(5):3466-73. Epub Nov. 8, 2002.

Sugimoto et al., Incorrect us of "immortalization" for B-lymphoblastoid cell lines transformed by Epstein-Barr virus. J Virol. Nov. 1999;73(11):9690-1.

Toda et al., Proteome analysis of Epstein-Barr virus-transformed B-lymphoblasts and the proteome database. J Chromatogr B. Apr. 5, 2003;787(1):197-206.

Traggiai et al., An efficient method to make human monoclonal antibodies from memory B cells: potent neutralization of SARS coronavirus. Nat Med. Aug. 2004;10(8):871-5. Epub Jul. 11, 2004.

Urlaub et al., Isolation of Chinese hamster cell mutants deficient in dihydrofolate reductase activity. Proc Natl Acad Sci U S A. Jul. 1980;77(7):4216-20.

Van Dijk et al., Human antibodies as next generation therapeutics. Curr Opin Chem Biol. Aug. 2001;5(4):368-74.

Wang et al., Quantitation of mRNA by the polymerase chain reaction. Proc Natl Acad Sci U S A. Dec. 1989;86(24):9717-21. Erratum in: Proc Natl Acad Sci U S A Apr. 1990;87(7):2865.

Wojcieszyn et al., Studies on the mechanism of polyethylene glycol-mediated cell fusion using fluorescent membrane and cytoplasmic probes. J Cell Biol. Jan. 1983;96(1):151-9.

Zafiropoulos et al., Induction of antigen-specific isotype switching by in vitro immunization of human naive B lymphocytes. J Immunol Methods. Jan. 15, 1997;200(1-2):181-90.

Chung et al., Human embryonic stem cell lines generated without embryo destruction. Cell Stem Cell. Feb. 7, 2008;2(2):113-7. doi: 10.1016/j.stem.2007.12.013. Epub Jan. 10, 2008.

Gustafsson et al., SPAM-8, a mouse-human heteromyeloma fusion partner in the production of human monoclonal antibodies. Establishment of a human monoclonal antibody against cytomegalovirus. Hum Antibodies Hybridomas. Jan. 1991;2(1):26-32.

Messer Peters et al., Production of interspecies T cell hybrids which retain differentiation specific surface antigens. J Immunol Methods. Aug. 12, 1983;62(1):39-47.

Treves et al., Establishment of cell lines from somatic cell hybrids between human monocytes and mouse myeloma cells. J Immunol. Feb. 1984;132(2):690-4.

Lyman, Biology of flt3 ligand and receptor. Int J Hematol. Aug. 1995;62(2):63-73. Abstract only.

PCT/AU2010/000716, dated Jul. 29, 2010, International Search Report and Written Opinion.

PCT/AU2010/000715, dated Dec. 22, 2011, International Preliminary Report on Patentability.

PCT/AU2010/000715, dated Jul. 29, 2010, International Search Report and Written Opinion.

PCT/AU2010/000716, dated Dec. 22, 2011, International Preliminary Report on Patentability.

EP 10785597.5, dated Jan. 8, 2014, Extended European Search Report.

\* cited by examiner

SEQUENCE LISTING

<160> NUMBER OF SEQ ID NOS: 16

<210> SEQ ID NO 1
<211> LENGTH: 20
<212> TYPE: DNA
<213> ORGANISM: Homo sapiens

<400> SEQUENCE: 1 accccactg aaaaagatga                                                   20

<210> SEQ ID NO 2
<211> LENGTH: 20
<212> TYPE: DNA
<213> ORGANISM: Homo sapiens

<400> SEQUENCE: 2
atcttcaaac ctccatgatg                                                  20

<210> SEQ ID NO 3
<211> LENGTH: 22
<212> TYPE: DNA
<213> ORGANISM: Homo sapiens

<400> SEQUENCE: 3
ctcttctgtc cagtcacaga cc                                               22

<210> SEQ ID NO 4
<211> LENGTH: 22
<212> TYPE: DNA
<213> ORGANISM: Homo sapiens

<400> SEQUENCE: 4
gaatagctct ggtggcttgc aa                                               22

<210> SEQ ID NO 5
<211> LENGTH: 24
<212> TYPE: DNA
<213> ORGANISM: Homo sapiens

<400> SEQUENCE: 5
ctgtgacaat gatcgcactc tatg                                             24

<210> SEQ ID NO 6
<211> LENGTH: 26
<212> TYPE: DNA
<213> ORGANISM: Homo sapiens

<400> SEQUENCE: 6
gattccagtg cattcatagt aatctc                                           26

<210> SEQ ID NO 7
<211> LENGTH: 31
<212> TYPE: DNA
<213> ORGANISM: Homo sapiens

<400> SEQUENCE: 7
atgcatgcgg ccgcggcatg tgtttggcag c                                     31

<210> SEQ ID NO 8
<211> LENGTH: 35
<212> TYPE: DNA
<213> ORGANISM: Homo sapiens

<400> SEQUENCE: 8
atccgcggcc gcatcgatag gtcaccgtca agatt        35

<210> SEQ ID NO 9
<211> LENGTH: 21
<212> TYPE: DNA
<213> ORGANISM: Homo sapiens

<400> SEQUENCE: 9
agcaggacag gacatggagg a        21

<210> SEQ ID NO 10
<211> LENGTH: 22
<212> TYPE: DNA
<213> ORGANISM: Homo sapiens

<400> SEQUENCE: 10
atcctgttga tggaactgac gc        22

<210> SEQ ID NO 11
<211> LENGTH: 22
<212> TYPE: DNA
<213> ORGANISM: Homo sapiens

<400> SEQUENCE: 11
tcaccgtggc aacctgacca tg        22

<210> SEQ ID NO 12
<211> LENGTH: 23
<212> TYPE: DNA
<213> ORGANISM: Homo sapiens

<400> SEQUENCE: 12
gagacagcac gttcccgtta ctg        23

<210> SEQ ID NO 13
<211> LENGTH: 20
<212> TYPE: DNA
<213> ORGANISM: Homo sapiens

<400> SEQUENCE: 13
gacacggccg tgtattactg        20

<210> SEQ ID NO 14
<211> LENGTH: 34
<212> TYPE: DNA
<213> ORGANISM: Homo sapiens

<400> SEQUENCE: 14 atccgcgcc gcggaattct cacacaggag acga        34

<210> SEQ ID NO 15
<211> LENGTH: 24
<212> TYPE: DNA
<213> ORGANISM: Homo sapiens

<400> SEQUENCE: 15
atgacccagt ctccatcctc cctg

```
<210> SEQ ID NO 16
<211> LENGTH: 29
<212> TYPE: DNA
<213> ORGANISM: Homo sapiens

<400> SEQUENCE: 16
atgcggccgc gggaagatga agacagatg                                    29
```

METHODS OF GENERATING CELLS EXHIBITING PHENOTYPIC PLASTICITY

RELATED APPLICATION

This application is a national stage filing under 35U.S.C. §371 of international application PCT/AU2010/000716, filed Jun. 10, 2010, which was published under PCT Article 21(2) in English, the disclosure of which is incorporated by reference herein in its entirety.

TECHNICAL FIELD

The present invention relates to cellular differentiation and, in particular to hybrid cells that exhibit phenotypic plasticity and methods for producing these cells. The invention also relates to methods for generating specific cells of a desired phenotype. The invention still further relates to methods of producing hybrid cells with a capacity to de-differentiate into an earlier progenitor state. The invention further contemplates the use of hybrid cells in a range of applications, for example tissue generation.

BACKGROUND

Any discussion of the prior art throughout the specification should in no way be considered as an admission that such prior art is widely known or forms part of common general knowledge in the field.

Reports on the ability of stem cells to regenerate bodily tissues and on unique plasticity of the cellular stem cell compartment have opened the possibility of targeted tissue repair. Hematopoietic stem cells (HSCs) exhibit both a capacity for self-renewal and the potential to generate into a variety of specialised blood cell types (lineages) upon exposure to specific microenvironments. The process of differentiation of different blood cells, ie hematopoiesis, provides a valuable model for examining how genetic programs are established and executed in vertebrates, and also how homeostasis of blood formation is altered in leukemias. Recent findings not only indicate how this may be achieved but also show the extraordinary plasticity of tissue stem cells in vivo.

Hematopoiesis is usually depicted in a hierarchical fashion, with HSCs giving rise first to progenitors and then to precursors with varying capacities to differentiate down multiple or single lineage pathways. Studies investigating the plasticity of cells committed to a particular lineage have found that the process of lineage switching required transformation and/or expression of oncogenes. Moreover, when evidence for lineage switching was observed it was found to have occurred only in small percentages of cells (Klinken et al, Cell 53: 857-867, 1988; Graf et at, Blood 99: 3089-3101, 2002).

Specifically, experiments with Abelson virus transformed pre-B lymphoma cell line treated with 5-azacystidine resulted in a subset of cells exhibiting macrophage-like properties, including the ability to adhere to plastic as well as phagocytic and esterase activities (Boyd et al, Nature 297:691-693, 1982). More recent experiments have demonstrated that concomitant expression of E-myc and v-raf oncogenes in B lymphoma cell lines or pre-leukemic bone marrow B lineage cells can lead to their conversion to macrophages. These transfected macrophage-like cells processed multiple myelomonocytic markers such as colony stimulating receptor-1 and expressed lysozyme but also retained features of the original cells such as immunoglobulin rearrangement. In addition to transition to macrophages, B-lineage cells were also reported to transit to granulocytes upon transfection with max gene (Lindeman et al, Immunity 1: 517-527, 1994). Significantly, only very small fractions of cells expressing trans-genes actually switched lineage, indicating that the transition from one lineage to another is a complex process which is not completely understood (Klinken et al, Cell 53: 857-867, 1988; Borzello et al, Mol. Cell. Biol. 10:2703-2714, 1990).

An alternate experimental approach which investigated hematopoietic lineage plasticity involved the generation of gene-knockout mice. Specifically, B lineage cells derived from Pax-5 knockout mice exhibited characteristics of pre-B cells such as expression of B220, AA4.1, SL chain and c-Kit (low) but not CD19. These cells also exhibited characteristics of pluripotent stem cells such as continuous self-renewal on stromal cells in presence of interleukin 7 (IL-7), horning to the bone marrow after transplantation, and the ability to differentiate into most hematopoietic cell types both in vivo and in vitro. For example, when transplanted into RAG2 knockout mice these cells differentiate into T cells (Rolink et al, Nature 401:556-562, 1999). When grown in the presence of different cytokines or growth factors they differentiated into a range of different cell types. For example, treatment with IL-2 resulted in conversion to natural killer cells (NK cells), treatment with CSF-1 and granulocyte-macrophage colony-stimulating factor (GM-CSF), resulted in conversion to dendritic cells, treatment with CSF-1 resulted in conversion to macrophages, and treatment with IL-3, IL-6, stem cell factor (SCF) and granulocyte colony-stimulating factor (G-CSF) resulted in conversion to neutrophils (Nutt et al, Nature 401: 556-562, 1999).

Although plasticity appeared to be demonstrated with cells derived from Pax-5 knockout mice, cells exhibiting a phenotype comparable to the Pax-5 knockout pre-B cells most likely do not exist in wild type animals as culture of pre-B cells from wild type mice is problematic (Kee et al, Curr. Opin. Immunol. 13: 180-185, 2001).

Other studies using transgenic mice investigating plasticity of common lymphoid progenitors (CLPs), showed that CPLs from a transgenic mouse line ectopically expressing human IL-2 receptor β chain when cultured on stromal cells in presence of IL-7 differentiated into B cells and NK cells. When IL-2 was added to the culture they formed granulocytes and macrophages. However, these results could not be repeated from control CLPs grown under the same conditions (Kondo et al, Nature 407: 383-386, 2000). Accordingly, the results of these studies seem to suggest that inducing cell plasticity requires the expression of genes not normally expressed by committed cells.

The cells exhibiting phenotypic plasticity detailed in the experiments mentioned above were either derived from mouse lymphomas, were cells transformed by an oncogene, or altered by mutations. Limited data exist on the plasticity of normal B-cells. One set of experiments described the conversion of CD19, DJ-rearrangement positive and B220 negative B cells from bone marrow of adult mice into adherent macrophage like cells when cultured with IL-3, IL-6 and GM-CF. However, conversion into NK or T cells was not possible to achieve (Montecino-Rodriguez et al, Nat. Immunol. 2: 83-88, 2001).

Very limited data is available on the reverse transformation from myeloid lineage into B lymphoid lineage. The experiments that have been undertaken were primarily concerned with forced expression of early B lineage specific transcription factors encoded by E2A, EBF and RAG gene. For example, forced expression of E2A caused the cells to lose their adherent properties, down-regulate the expression of Mac-1 and c-fms, and induce a number of B lineage specific genes including an ability to form κ chain in response to mitogens (Kee et al, J. Exp. Med. 188: 699-713, 1998). The fact that these cells did not acquire full B-lineage phenotype suggests that the combination of E2A, EBF, and RAG gene expressions is not sufficient for lineage specification and that additional genes must be involved (Romanow et al, Mol. Cell. 5: 343-353, 2000).

There are also examples of the possible conversion between T-lineage and macrophages. A subset of purified pro-T cells when cultured in the conditioned medium from a thymic stromal cell line generated functional macrophages. The same conversion was observed in the presence of a combination of IL-6, IL-7 and macrophage colony-stimulating factor (M-CSF; CSF-1), but at a much lower frequency (Lee et al, J. Immunol. 166: 5964-5989, 2001).

The most described transdifferentiation is arguably the plasticity within myeloid-erythroid compartment. Most experiments in this field are based on enforced transcription factor expression. The most reproducible and predictable experimental system allowing direct differentiation of cultured cell lines from one lineage to another is based on transformation of avian erythroid-megakaryocytic progenitors by the Myb-Ets-encoding leukemia virus. These E26-MEP cells express a number of megakaryocytic and stem cell surface markers such as MEP21/thrombomucin/PCLP1 and GPIIaIIb/CD41 (Graf et al, Cell 70:201-213, 1992; McNagny et al, J. Cell. Biol. 138:1395-14-7, 1997) as well as GATA-1 and FOG-1 but no myelomonocytic cell surface markers and no or low levels of PU.1, C/EBPα and C/EBPβ. If v-Ets is inactivated in these cells, they differentiate into erythroid cells (Golay et al, Cell 55: 1147-1158, 1987; Rossi et al, Curr. Biol. 6: 866-872, 1988). Alternatively, inactivation of Myb leads to conversion of these cells into thrombocytes (Frampton et al, EMBO J. 14: 2866-2875, 1995). Through an introduction of oncogenes of the ras pathways via retroviral transformation or by activating protein kinase C (PKC) the cells can be committed to becoming either eosinophils or myeloblasts, depending on the strength of the signal (Graf et al, Cell 70:201-213, 1992; Rossi et al, EMBO J. 15: 1894-1901, 1996). It is widely acknowledged that maintenance of multi-potent or differentiated state is the result of an on-going process and that activation or repression of a single (or a few) nuclear regulators may lead to differentiation, lineage switching or de-differentiation (Orkin, Nature Rev. Genet. 1: 57-64, 2000). In this context, study of nuclear transcription factors that are restricted in their expression to particular lineages is of particular interest, as they establish gene expression programmes intrinsic to cell diversification. Whilst growth factors are important in sustaining hematopoiesis, cell viability and proliferation, they are not necessarily instructive for pathway differentiation (Sokolovsky et al, Proc. Natl. Acad. Sci. USA 95: 6573-6575, 1998; Stoffel et al, Proc Natl. Acad. Sci. USA 96: 698-702, 1999).

The complexity of lineage differentiation has been further illustrated by studies which indicate that the concentration or level at which a given factor is expressed may influence direction of lineage differentiation. Specifically, in a transformed chicken progenitor system (Kulessa et al, Genes Dev. 9: 1250-1262, 1995), the lineage outcome correlated with the level of GATA-1 expression. At low levels, it generated eosinophils and at high levels it produced erythroid and megakaryocytic cells. Recently, it has also been found that high levels of PU.1 favour the development of macrophages, whereas at lower levels, B cells are generated (DeKoter et al, Science 288: 146-149, 2000).

It has also recently emerged that HSCs possess a remarkable capacity to contribute to different types of tissue. Therefore, the ability to control or introduce the plasticity of cells has potentially many valuable applications. For example, functional hepatic reconstruction of FAH tyrosinase deficiency was achieved by using highly purified HSCs. Hepatocytes are derived from endoderm, thus it appears that mesodermally derived HSCs have a capacity to convert to an endodermal derivative (Lagasse et al, Nature Med. 6: 1229-1234, 2000). Another set of experiments points to even greater plasticity of HSCs, whereby a single stem cell derived from bone marrow demonstrated low level contribution to various epithelial tissues in many organs even though no data on functional capacity of these cells were presented (Krause et al, Cell 105: 369-377, 2001). Recent experiments with adult stem cells derived from enriched bone marrow populations further indicated a capacity to restore muscle cells after myocardial infarction (Orlic et al, Ann. NY Acad. Sci. 938: 221-230, 2001; Orlic et al, Nature 410: 701-705, 2001; Jackson et al, J. Clin. Invest. 107: 1395-1402, 2001).

The studies detailed above, clearly indicate that understanding and being able to introduce plasticity into cells has potentially valuable applications in for example tissue regeneration.

There is also increasing evidence that hematopoietic cells can retro- or de-differentiate into an earlier progenitor state. For example, chicken myelomonocytic cells transformed by a temperature sensitive (ts) mutant of v-myb exhibit an immature phenotype, resembling myeloblasts at the permissive temperature. However, at a non-permissive temperature they shift into adherent, phagocytic, macrophage-like cells and cease dividing. Time-lapse experiments showed that this process was reversible with most adherent cells acquiring back blast morphology and re-entering the cell cycle within 2 to 3 days after shift to the permissive temperature (Beug et al, Genes Dev. 1: 277-286, 1987).

As yet, the majority of studies investigating trans-differentiation have been done with non-human cells as no reproducible and stable model exists which allows the generation of functionally differentiated myeloid or lymphoid cells from a single cell population by manipulation of the environment.

At present, all trans-differentiation studies within a hematopoietic lineage have been carried out in non-human models requiring transplantation into living host. Moreover, none of these model systems have demonstrated a high frequency of cells that switch to different lineages, thus limiting the efficacy of in vitro and in vivo studies. Most significantly, these models frequently involve the use of cell phenotypes which do not exist naturally, such as cells isolated from transgenic animals or artificially transformed cells.

There is limited or no data available in relation to trans-differentiation of mature effector cells. This results from a lack of a cell system or animal model which includes markers of mature phenotypes of B cells, T cells and myeloid cells, specifically markers such as CD19, CD4 or CD3, and CD15. The majority of experiments with B lineage transdifferentiation involve pre-B cells with very low frequency of conversion to mature CD19 positive cells. Whilst conversion between B lineage and myeloid and T lymphoid to myeloid has been achieved with limited success, no inter-conversion between B and T-lymphoid lineage has been observed.

It is an object of the present invention to overcome or ameliorate at least one of the disadvantages of the prior art, or to provide a useful alternative.

SUMMARY OF INVENTION

It is generally considered that multi-fusion cells are unstable and that the more cells involved in a fusion, the greater the instability of the resulting hybrid cell. Surprisingly, in the present invention, hybrid cells resulting from the fusion of a number of cells, for example three cells, exhibit functional stability. In particular, it has been found that cells derived from different lineages can be somatically fused or hybridised to form substantially stable chimeric/hybrid cells. More particularly, the present invention relates to cross-lineage chimeric/hybrid cells generated from the hybridisation of at least three parental cells resulting in a tri-hybrid where at least two parental cells are derived from different lineages and wherein a myeloma cell is not included in the hybridisation.

It has also surprisingly been found that the stable chimeric/hybrid cells of the invention exhibit phenotypic plasticity which allows their conversion into a cell of a desired phenotype such as a desired lineage by treatment with a predetermined exogenous factor or factors. These factors may include a cytokine, a growth factor, an immunoglobulin, a receptor ligand, a cell such as a stromal cell or a combination thereof.

Previously known methods of altering cellular phenotype have involved cellular transformation, for example, by alteration of oncogene expression or isolation of cells from transgenic animals. These methods are technically complex and produce inefficient results, which routinely include low levels of cellular phenotypic plasticity. Moreover, these known methods can not readily be employed on human cells.

The present invention provides significant advantages over previously known methods in terms of providing a stable cellular system allowing efficient trans-differentiation or de-differentiation. Moreover, the present invention permits the trans-differentiation or de-differentiation of human cells.

In one embodiment, the present invention relates to providing a simple and versatile model system for investigating the process of cell differentiation, for example differentiation of blood cells, ie hematopoiesis. The present invention also relates to providing a valuable model for examining how genetic programs are established and executed in vertebrates. The present invention also relates to providing an understanding of the formation of cellular malignancies, for example how homeostasis of blood formation is altered in leukemias.

In an alternative embodiment, the present invention also relates to the generation of cells that express phenotypic plasticity that may be used in applications such as the generation of specific cells or tissues for the treatment of a disease.

The present invention may represent a model system study of the differentiation process. Also, there may be situations where the ability to differentiate or de-dedifferentiate specific cells from mature cells may be advantageous. For example, some patients lack the ability to produce enough cells with a particular phenotype due to mutation at some point in the differentiation pathway. For example, they may have pre-B cells but not mature B cells. Isolating pre-B cells from such patients and driving them to B cells would not help. However, their other mature cell types without mutation may be trans-differentiated to B cells using the invention.

In certain embodiments the invention relates to the creation of a haematopoietic transdifferentiation system (HTS) which allows the generation of B cells, T cells or myelomonocytic cells on demand.

In one embodiment a tri-hybrid cell exhibiting cellular plasticity may be generated by the hybridisation of one myelomonocytic progenitor (either immortal or primary), one B cell (either immortal or primary) and one T cell (either immortal or primary) wherein said hybrid cell expresses specific CD markers from all of the cell types used in the hybridisation for example CD15, CD19, CD4. However, the skilled addressee will understand that the present invention is not limited to hybrid cells expressing these particular markers.

In certain specific embodiments, the hybrid cells of the invention may be generated by hybridisation of, for example:

one common myelomonocytic progenitor K562 (CD72$^+$ CD15$^+$) and one primary B cell (CD19) and one T cell (CD4)—KBT;

one common myelomonocytic progenitor K562 and immortal B cell WIL2NS and immortal T cell MOLT4—KMW; or one common myelomonocytic progenitor derived from primary bone marrow CD34$^+$CD15$^+$ cell, one immortal B cell WIL2NS and one primary T cell—WTM.

In a particularly preferred embodiment, the hybrid cells of the invention may be differentiated into a B, T or myelomonocytic cell on demand by either exposing them to various factors such as a cytokine, a growth factor, an immunoglobulin, a receptor ligand a cell, such as a stromal cell or a combination thereof or by further hybridising them with a desired cell type. In another embodiment, the hybrid cell of the invention may be de-differentiated by further hybridising them with another cell such as a progenitor cell such or a cell that expresses for example CD34.

According to a first aspect, the present invention provides a method of generating a cell of predetermined phenotype said method comprising the steps of hybridising:

a first cell, wherein said first cell is a stem cell or a cell derived from an uncommitted progenitor cell;

a second cell derived from a common lymphoid progenitor cell; and a third cell derived from a common lymphoid progenitor cell, to produce a hybrid cell and exposing said hybrid cell to a predetermined environment such that said hybrid cell becomes said cell of a predetermined phenotype.

In one embodiment the predetermined phenotype is a B cell, a T cell or a myeloid cell. In an alternate embodiment, the predetermined phenotype is a de-differentiated phenotype relative to the hybrid cell. The de-differentiated phenotype comprises for example expression of one or more of CD34 or CD10 or Pax-5 or λ-like.

In certain embodiments the first cell is a cell derived from a common myeloid progenitor cell, the second cell is a cell derived from a B lymphoid lineage and the third cell is a cell derived from a T lymphoid lineage.

Preferably, the cell derived from a common myeloid progenitor cell, is a myelomonocytic progenitor cell, monocyte, macrophage, eosinophil, neutrophil, dendritic cell or basophil. As such, it is clear that the invention provides a method of generating a cell of predetermined phenotype comprising the step of hybridising a myelomonocytic progenitor cell, monocyte, macrophage, eosinophil, neutrophil, dendritic cell or basophil, a B lymphoid cell and a T lymphoid cell.

Preferably the cell derived from a common myeloid progenitor cell displays at least one of the following CD antigens CD16, CD15 or CD14. As such, it is clear that the invention provides a method of generating a cell of predetermined phenotype comprising hybridising a common myeloid progenitor cell that displays at least one of the following CD antigens CD16, CD15 or CD14, a B lymphoid cell and a T lymphoid cell.

In one embodiment, the cell derived from a common myeloid progenitor cell is a monocyte. As such, the invention provides a method of generating a cell of predetermined phenotype comprising hybridising a monocyte, a B lymphoid cell and a T lymphoid cell.

In one embodiment, the cell derived from a common myeloid progenitor cell is a primary myelomonocytic progenitor. As such, the invention provides a method of generating a cell of predetermined phenotype comprising hybridising a primary myelomonocytic progenitor, a B lymphoid cell and a T lymphoid cell.

In one embodiment, the cell derived from a common myeloid progenitor cell is an immortalised cell. As such, it is clear that the invention provides a method of generating a cell of predetermined phenotype comprising hybridising an immortalised cell selected from a myelomonocytic progenitor, monocyte, macrophage, eosinophil, neutrophil, dendritic cell or basophil, a B lymphoid cell and a T lymphoid cell.

In another embodiment, the cell derived from a common myeloid progenitor cell is derived from spleen, peripheral blood, umbilical cord blood or bone marrow. As such, it is clear that the invention provides a method of generating a cell of predetermined phenotype comprising hybridising a common myeloid progenitor cell derived from spleen, peripheral blood, umbilical cord blood or bone marrow, a B lymphoid cell and a T lymphoid cell.

In another embodiment, the cell derived from B lymphoid lineage is a pre-B cell, an immature B cell, a naïve B cell, an activated B cell or an effector B cell. As such, it is clear that the invention provides a method of generating a cell of predetermined phenotype comprising hybridising a common myeloid progenitor cell or a stem cell, a B lymphoid cell selected from a pre-B cell, an immature B cell, a naïve B cell, an activated B cell or an effector B cell and a T lymphoid cell.

In one embodiment, the effector B cell is an antigen-experienced B-cell or a plasma cell. As such, the invention provides a method of generating a cell of predetermined phenotype comprising hybridising a common myeloid progenitor cell or stem cell, an antigen-experienced B-cell or a plasma cell and a T lymphoid cell.

In one embodiment, the cell derived from B lymphoid lineage displays at least one of the following CD antigens CD19, CD20, CD72 or CD5. As such, the invention provides a method of generating a cell of predetermined phenotype comprising hybridising a common myeloid progenitor cell or a stem cell, a B lymphoid cell which displays at least one of the following CD antigens CD19, CD20, CD72 or CD5 and a T lymphoid cell.

In one embodiment, the cell derived from T lymphoid lineage is a pre-T cell, an immature T cell, a naïve T cell, an activated T cell or an effector T cell. As such, the invention provides a method of generating a cell of predetermined phenotype comprising hybridising a common myeloid progenitor cell or stem cell, a B lymphoid cell and a T lymphoid cell selected from a pre-T cell, an immature T cell, a naïve T cell, an activated T cell or an effector T cell.

In one embodiment, said cell derived from T lymphoid lineage displays at least one of the following CD antigens CD3, CD4, CD5 or CD8. As such, the invention provides a method of generating a cell of predetermined phenotype comprising hybridising a common myeloid progenitor cell or stem cell, a B lymphoid cell and a T lymphoid cell which displays at least one of the following CD antigens CD3, CD4, CD5 or CD8.

In one embodiment, the cell derived from B lymphoid lineage is an immortalised cell. As such, the invention provides a method of generating a cell of predetermined phenotype comprising hybridising a common myeloid progenitor cell or stem cell, an immortal B lymphoid cell and a T lymphoid cell.

In one embodiment, the cell derived from T lymphoid lineage is an immortalised cell. As such, the invention provides a method of generating a cell of predetermined phenotype comprising hybridising a common myeloid progenitor cell or stem cell, a B lymphoid cell and an immortal T lymphoid cell.

In one embodiment, said cell derived from B lymphoid lineage is derived from lymphoid tissue. As such, the invention provides a method of generating a cell of predetermined phenotype comprising hybridising a common myeloid progenitor cell or stem cell, a B lymphoid cell derived from lymphoid tissue and a T lymphoid cell.

In one embodiment, said cell derived from T lymphoid lineage is derived from lymphoid tissue. As such, invention provides a method of generating a cell of predetermined phenotype comprising hybridising a common myeloid progenitor cell or stem cell, a B lymphoid cell and a T lymphoid cell derived from lymphoid tissue.

Where the B or T lymphoid cells included in the method of the invention are derived from lymphoid tissue said lymphoid tissue is preferably selected from peripheral blood, cord blood, spleen, bone marrow, thymus, tonsils, adenoids, and regional lymph nodes.

In one embodiment, at least one of the cells included in the method of the invention is a human cell. It will also be clear that the method of the invention may include cells other than a human cell for example a mouse cell.

In one embodiment, the cell derived from a common myeloid progenitor cell is a K562 cell. As such, it will be clear that the invention provides a method of generating a cell of predetermined phenotype comprising hybridising a K562 cell, a B lymphoid cell and a T lymphoid cell.

In one embodiment, the second cell or the third cell is a WIL2NS cell or a MOLT4 cell respectively. As such, it will be clear that the invention provides a method of generating a cell of predetermined phenotype comprising hybridising a common myeloid progenitor cell or stem cell, a WIL2NS cell and a T lymphoid cell. The invention also provides a method of generating a cell of predetermined phenotype comprising hybridising a common myeloid progenitor cell or stein cell, a B lymphoid cell and a MOLT4 cell.

In one embodiment, the first cell is a K562 cell, the second cell is a WIL2NS cell and the third cell is a MOLT4 cell.

In another embodiment, the first cell is a K562 cell, the second cell is a primary B cell and the third cell is a primary T cell.

In another embodiment, the first cell is a primary human monocyte, the second cell is a WIL2NS cell and the third cell is a primary T cell.

In another embodiment, the first cell is a primary human myelomonocytic progenitor, the second cell is a WIL2NS cell and the third cell is a primary human T cell.

In another embodiment, the first cell is a K562 cell, the second cell is a WIL2NS cell and the third cell is a primary T cell.

In still a further embodiment, the first cell is a primary mouse monocyte, the second cell is an SP2 cell and the third cell is a primary mouse T cell.

In certain embodiments, the B cell and the T cell express CD5. In alternate embodiments the B cell expresses CD20 and CD72 and said T cell express CD4 and CD8.

In certain embodiments, the hybrid cell generated by the method of the invention is further hybridised with another cell. Wherein the other cell may be, for example a stem cell or a progenitor cell.

In certain embodiments, the predetermined environment comprises a thymic stromal cell, a cytokine, a growth factor, an immunoglobulin, a receptor ligand or combination thereof. As such, it will be clear that the method of the invention provides hybridising: three cells, as described above, for example
- a first cell, wherein said first cell is a cell derived from an uncommitted progenitor cell;
- a second cell derived from a common lymphoid progenitor cell; and
- a third cell derived from a common lymphoid progenitor cell, to produce a hybrid cell and exposing said hybrid cell to thymic stromal cells, a cytokine, a growth factor, an immunoglobulin, a receptor ligand or combination thereof such that said hybrid cell becomes said cell of a predetermined phenotype.

In certain embodiments, the cytokine or growth factor included in the predetermined environment is selected from the group consisting of IL-2, IL-3, IL-4, IL-5, IL-6, 1-10, IL-1 beta, IL-7, IL-23, TGF-beta, M-CSF, GM-CSF and IFN-gamma.

In certain embodiments, the immunoglobulin is selected from the group consisting of anti-IL-4, anti-IFN-gamma and anti-CD3/CD28.

In certain embodiments, the receptor ligand is Flt 3 ligand or CD40 ligand.

In another aspect, the present invention provides a hybrid cell generated by hybridisation of:
- a first cell, wherein said first cell is a stem cell or a cell derived from an uncommitted progenitor cell;
- a second cell derived from a common lymphoid progenitor cell; and
- a third cell derived from a common lymphoid progenitor cell, and wherein said first cell is not a myeloma cell.

In one embodiment, said second cell is a cell derived from B lymphoid lineage and said third cell is a cell derived from B lymphoid lineage.

In another embodiment, said second cell is a cell derived from B lymphoid lineage and said third cell is a cell derived from T lymphoid lineage.

Preferably, said first cell is a cell derived from a common myeloid progenitor cell. As such, it is clear that the invention provides a hybrid cell generated by hybridisation of a common myeloid progenitor cell or a stem cell, and two B lymphoid cells. The invention also provides a hybrid cell generated by hybridisation of a common myeloid progenitor cell, or a stem cell, a B lymphoid cell and a T lymphoid cell.

Preferably said cell derived from a common myeloid progenitor cell, is a myelomonocytic progenitor cell, monocyte, macrophage, eosinophil, neutrophil, dendritic cell or basophil. As such it is clear that the invention provides a hybrid cell generated by hybridisation of a myelomonocytic progenitor cell, monocyte, macrophage, eosinophil, neutrophil, dendritic cell or basophil and two B lymphoid cells. The invention also provides a hybrid cell generated by hybridisation of a myelomonocytic progenitor cell, monocyte, macrophage, eosinophil, neutrophil, dendritic cell or basophil, a B lymphoid cell and a T lymphoid cell.

Preferably said cell derived from a common myeloid progenitor cell displays at least one of the following CD antigens CD16, CD15 or CD14. As such it is clear that the invention provides a hybrid cell generated by hybridisation of a common myeloid progenitor cell that displays at least one of the following CD antigens CD16, CD15 or CD14 and two B lymphoid cells. The invention also provides a hybrid cell generated by hybridisation of a hybrid cell generated by hybridisation of a common myeloid progenitor cell that displays at least one of the following CD antigens CD16, CD15 or CD14, a B lymphoid cell and a T lymphoid cell.

In one embodiment, said cell derived from a common myeloid progenitor cell is a monocyte. As such, the invention provides a hybrid cell generated by hybridisation of a monocyte and two B lymphoid cells. The invention also provides a hybrid cell generated by hybridisation of a monocyte, a B lymphoid cell and a T lymphoid cell.

In another embodiment, said cell derived from a common myeloid progenitor cell is a primary myelomonocytic progenitor. As such, the invention provides a hybrid cell generated by hybridisation of a primary myelomonocytic progenitor cell and two B lymphoid cells. The invention also provides a hybrid cell generated by hybridisation of a primary myelomonocytic progenitor cell, a B lymphoid cell and a T lymphoid cell.

In one embodiment, said cell derived from a common myeloid progenitor cell is an immortalised cell. As such, it is clear that the invention provides a hybrid cell generated by hybridisation of an immortalised cell selected from a myelomonocytic progenitor cell, monocyte, macrophage, eosinophil, neutrophil, dendritic cell or basophil and two B lymphoid cells. The invention also provides a hybrid cell generated by hybridisation of an immortalised cell selected from a myelomonocytic progenitor cell, monocyte, macrophage, eosinophil, neutrophil, dendritic cell or basophil, a B lymphoid cell and a T lymphoid cell.

In another embodiment, said cell derived from a common myeloid progenitor cell is derived from spleen, peripheral blood, umbilical cord blood or bone marrow. As such, it is clear that the invention provides a hybrid cell generated by hybridisation of a common myeloid progenitor cell derived from spleen, peripheral blood, umbilical cord blood or bone marrow and two B lymphoid cells. The invention also provides a hybrid cell generated by hybridisation of a common myeloid progenitor cell derived from spleen, peripheral blood, umbilical cord blood or bone marrow, a B lymphoid cell and a T lymphoid cell.

In another embodiment, said cell derived from B lymphoid lineage is a pre-B cell, an immature B cell, a naïve B cell, an activated B cell or an effector B cell. As such, it is clear that the invention provides a hybrid cell generated by hybridisation of a common myeloid progenitor cell or a stem cell and two B lymphoid cells selected from a pre-B cell, an immature B cell, a naïve B cell, an activated B cell or an effector B cell. The invention also provides a hybrid cell generated by hybridisation of a common myeloid progenitor cell or stem cell, a B lymphoid cell selected from a pre-B cell, an immature B cell, a naïve B cell, an activated B cell or an effector B cell and a T lymphoid cell.

In one embodiment, said effector B cell is an antigen-experienced B-cell or a plasma cell. As such, the invention provides a hybrid cell generated by hybridisation of a common myeloid progenitor cell or stem cell and two B lymphoid cells selected from an antigen-experienced B-cell or a plasma cell. The invention also provides a hybrid cell generated by hybridisation of a common myeloid progenitor cell or stem cell, an antigen-experienced B-cell or a plasma cell and a T lymphoid cell.

In one embodiment, said cell derived from B lymphoid lineage displays at least one of the following CD antigens CD19, CD20, CD72 or CD5. As such, the invention provides a hybrid cell generated by hybridisation of a common myeloid progenitor cell or stem cell and two B lymphoid cells which display at least one of the following CD antigens CD19, CD20, CD72 or CD5. The invention also provides a hybrid cell generated by hybridisation of a common myeloid progenitor cell or stem cell, a B lymphoid cell which displays at least one of the following CD antigens CD19, CD20, CD72 or CD5 and a T lymphoid cell.

In one embodiment, said cell derived from T lymphoid lineage is a pre-T cell, an immature T cell, a naïve T cell, an activated T cell or an effector T cell. As such, the invention provides a hybrid cell generated by hybridisation of a common myeloid progenitor cell or stem cell, a B lymphoid cell and a T lymphoid cell selected from a pre-T cell, an immature T cell, a naïve T cell, an activated T cell or an effector T cell.

In one embodiment, said cell derived from T lymphoid lineage displays at least one of the following CD antigens CD3, CD4, CD5 or CD8. As such, the invention provides a hybrid cell generated by hybridisation of a common myeloid progenitor cell or stem cell, a B lymphoid cell and a T lymphoid cell which displays at least one of the following CD antigens CD3, CD4, CD5 or CD8.

In one embodiment, said cell derived from B lymphoid lineage is an immortalised cell. As such, the invention provides a hybrid cell generated by hybridisation of a common myeloid progenitor cell or stem cell and two B lymphoid cells, at least one of which can be an immortal cell. The invention also provides a hybrid cell generated by hybridisation of a common myeloid progenitor cell or stem cell, an immortal B lymphoid cell and a T lymphoid cell.

In one embodiment, said cell derived from T lymphoid lineage is an immortalised cell. As such, the invention provides a hybrid cell generated by hybridisation of a common myeloid progenitor cell or stem cell, a B lymphoid cell and an immortal T lymphoid cell.

In one embodiment, said cell derived from B lymphoid lineage is derived from lymphoid tissue. As such, the invention provides a hybrid cell generated by hybridisation of a common myeloid progenitor cell or stem cell and two B lymphoid cells derived from lymphoid tissue. The invention also provides a hybrid cell generated by hybridisation of a common myeloid progenitor cell or stem cell, B lymphoid cell derived from lymphoid tissue and a T lymphoid cell.

In one embodiment, said cell derived from T lymphoid lineage is derived from lymphoid tissue. As such, invention provides a hybrid cell generated by hybridisation of a common myeloid progenitor cell or stem cell, B lymphoid cell and a T lymphoid cell derived from lymphoid tissue.

Where the B or T lymphoid cells included in the hybrid cells of the invention are derived from lymphoid tissue said lymphoid tissue is preferably selected from peripheral blood, cord blood, spleen, bone marrow, thymus, tonsils, adenoids, and regional lymph node.

In one embodiment, at least one of the cells included in the generation of the hybrid cell of the invention is a human cell. It will also be clear that the hybrid cell of the invention may include a cell other than a human cell for example a mouse cell.

In one embodiment, said cell derived from a common myeloid progenitor cell is a K562 cell. As such, it will be clear that the invention provides a hybrid cell generated by hybridisation of a K562 cell and two B lymphoid cells. The invention also provides a hybrid cell generated by hybridisation of a K562 cell, an immortal B lymphoid cell and a T lymphoid cell.

In one embodiment, said second cell or said third cell is a WIL2NS cell or a MOLT4 cell respectively. As such, it will be clear that the invention provides a hybrid cell generated by hybridisation of a common myeloid progenitor cell or stem cell, a WIL2NS cell and a T lymphoid cell. The invention also provides a hybrid cell generated by hybridisation of a common myeloid progenitor cell or stem cell, a B lymphoid cell and a MOLT4 cell.

In one embodiment, said first cell is a K562 cell, said second cell is a WIL2NS cell and said third cell is a MOLT4 cell.

In another embodiment, said first cell is a K562 cell, said second cell is a primary B cell and said third cell is a primary T cell.

In another embodiment, said first cell is a primary human monocyte, said second cell is a WIL2NS cell and said third cell is a primary T cell.

In another embodiment, said first cell is a primary human myelomonocytic progenitor, said second cell is a WIL2NS cell and said third cell is a primary human T cell.

In another embodiment, said first cell is a K562 cell, said second cell is a WIL2NS cell and said third cell is a primary T cell.

In another embodiment, said first cell is a primary monocyte, said second cell is a WIL2NS cell and said third cell is a WIL2NS cell.

In another embodiment, said first cell is a primary mouse monocyte, said second cell is a SP2 cell and said third cell is a primary mouse T cell.

In another embodiment, said first cell is a primary mouse monocyte, said second cell is a SP2 cell and said third cell is a SP2 cell.

In another embodiment, said first cell is a primary human or mouse monocyte, said second cell is a WIL2-NS cell and said third cell is a SP2 cell.

In one embodiment, the hybrid cell of the invention expresses a desired protein. In one embodiment said protein is an endogenous protein. In another embodiment, said protein is a recombinant protein. Preferably, said protein is a cytokine eg a colony stimulating factor or an interleukin. In one embodiment said protein is GM-CSF. In another embodiment, said protein is interleukin 2. In yet another embodiment, said protein is a receptor or fragment thereof. In yet another embodiment, said protein is a soluble receptor.

In one embodiment, said protein is a human IL-4 receptor alpha chain. In another embodiment said protein is IgM. In yet another embodiment, said protein is IgG. In a still a further embodiment said protein is CD54.

In one embodiment, said hybridisation used to generate the hybrid cell of the invention is achieved by electrical means. In another embodiment, said hybridisation to generate the hybrid cell of the invention is achieved by chemical means.

In one embodiment, the hybrid cell of the invention is further hybridised with a cell that expresses a protein of interest.

In one embodiment, said hybridisation used to generate the hybrid cell of the invention is carried out by hybridising three individual cells.

In another embodiment, said hybridisation used to generate the hybrid cell of the invention is carried out using three populations of cells wherein each population includes a plurality of identical cell types or phenotypes.

In one embodiment, said hybrid cell of the invention is enriched for a particular cell type-defining marker to permit the expression of a protein exhibiting a desired post-translational modification or desired functionality.

DEFINITIONS

In the context of the present invention, the words "comprise", "comprising" and the like are to be construed in their inclusive, as opposed to their exclusive, sense, that is in the sense of "including, but not limited to".

Hybrid Cell

A hybrid cell is a cell that comprises components from more than one genome (other than zygotes and their derivatives). It is a cell that is constructed from a somatic cell hybridisation (or a whole cell hybridisation) of, for example, two or more biological cells (parent cells). The parent cells can be obtained from either of the same lineage (or species) or a different lineage (or species). The hybrid cell created from the same lineage and species is dubbed auto-hybrid, whereas that of different lineages is dubbed a hetero-hybrid.

Chimeric Cell

A chimeric cell is an artificially produced hybrid cell with a genome originating from two or more different species.

Cross-Lineage Hybrid Cell

A cross-lineage hybrid cell is an artificially produced hybrid cell with a genome originating from two or more cells derived from different cell lineages. Hematopoietic cells for example, are divided into two main lineages: lymphoid (T cells, B cells and NK cells) and myeloid (monocytes and macrophages, neutrophils, basophils and eosinophils, erythrocytes, megakaryocytes/platelets, dendritic cells).

Tri-Hybrid Cell

A tri-hybrid cell is an artificially produced hybrid cell with a genome originating from three cells.

Stable

When referring to a cell, the term "stable" denotes a cell's capacity to demonstrate a consistency of a given growth or productivity parameter, or consistency of the cell line's product characteristics with increasing generation number. When used in reference to a stable transfectant it denotes a cell line that expresses a trans-gene at a relatively constant level substantially indefinitely.

Somatic Cell Hybridisation

In the context of the present application the term "somatic cell hybridisation" refers to a process in which one single viable cell is created from two or more diploid (non-gamete) cells (parent cells) in such a way that the plasma-membranes of the cells are induced to be in good contact, a reversible breakdown of the plasma membranes of the parent cells at the point of contact is simultaneously induced and the entities or organelles of each parent cell are combined within the envelope of the newly formed single cell. The newly formed single cell is dubbed a hybridised cell or hybrid cell.

Stem Cell

The term "stem cell" refers to an unspecialised cell with a capacity to divide by mitosis and to develop into a range of different cell types. Stem cells may include embryonic stem cells, "adult" stem cells derived from umbilical cord or stem cells derived from adults. Stem cells include cells that have an unlimited capacity to differentiate into all cell types, ie totipotent cells. Stem cells also may include cells that are limited in their capacity to differentiate into specialised cells, for example pluripotent, multipotent, oligopotent or unipotent stem cells.

Immortalised Cell

The term "immortalised" cell refers to a cell which has the capacity for indefinite growth. It will be clear that an immortalised cell may be derived from an in vivo malignancy or embryo. Alternatively, an immortalised cell may be derived by performing an action on a cell that induces a capacity for indefinite growth. These actions may include, for example, in vitro transformation processes eg the introduction of viral genes such as Epstein-Barr virus (EBV), Simian virus 40 (SV40) T antigen, adenovirus E1A and E1B, and human papillomavirus (HPV) E6 and E7. Alternatively, an immortalised cell may be derived from a cell via expression of the telomerase reverse transcriptase protein (TERT) or other means. Immortalised cells may also be derived from cells in which oncogene expression has been modified. Immortalised cells may be derived from any action that induces a capacity for indefinite growth including, but not limited to, UV exposure or spontaneous transformation in which the mechanism for immortality is not known.

Myeloma Cell

The term "myeloma cell" refers to a malignancy of a plasma cell.

Hybridoma

The term "hybridoma" refers to a cell which is produced by the hybridisation of a myeloma cell and a B-cell derived from the spleen of an immunised animal. Hybridomas are immortalised cells with a capacity to produce monoclonal antibodies.

Phenotype

The term "phenotype" refers to the physical characteristics or morphology of a cell. For example it may relate to a particular cell lineage, for example lymphoid or myeloid lineage. Alternatively, the term "phenotype" may relate to the expression of one or more molecules for example on the surface of the cell, such as, CD markers or molecules inside the cell, such as transcription factors.

Uncommitted Progenitor Cell

An uncommitted progenitor cell is an early descendant of a stem cell that can only differentiate into limited kinds of cells without being committed to any specific lineage, but it cannot renew itself anymore.

Common Myeloid Progenitor Cell

A common myeloid progenitor cell is a progeny of a hematopoietic stem cell restricted to the myeloid lineage and capable of giving rise to either megakaryocyte/erythrocyte or granulocyte/macrophage progenitors but not lymphoid cells.

B Lymphoid Lineage-Derived Cell

A B lymphoid lineage-derived cell is any cell originating from a common lymphoid progenitor following its B lineage commitment to become any type of B cells.

T Lymphoid Lineage-Derived Cell

A T lymphoid lineage-derived cell is any cell originating from a common lymphoid progenitor following its T lineage commitment to become any type of T cells.

Granulocyte-Macrophage Progenitor Cell

A granulocyte-macrophage progenitor cell is a progenitor cell originating from a common myeloid progenitor cell and being committed to the granulocyte and monocyte lineages but not to megakaryocyte and erythroid lineages.

Megakaryocyte-Erythroid Progenitor Cell

A megakaryocyte-erythroid progenitor cell is a progenitor cell originating from a common myeloid progenitor cell and being committed to the megakaryocyte and erythroid lineages but not to granulocyte and monocyte lineages.

Pre-B Cell

A pre-B-cell is a developing B cell at the stage when the heavy chain of membrane bound IgM is expressed with surrogate light chain.

Immature B Cell

An immature B cell refers to a developing B cell in bone marrow where at the recombination stage of antibody loci VJ are rearranged on L chains and VDJ are rearranged on H chains IgM receptor expression is exhibited.

Naïve B Cell

A naïve B cell is a mature B cell that has differentiated and matured in bone marrow through random gene rearrangement of its surface immunoglobulin but not has yet encountered cognate antigen in the periphery.

Activated B Cell

An activated B cell is a type of mature B cell that has encountered its cognate antigen in the periphery through antigen recognition via BCR resulting in a combination of clonal proliferation and terminal differentiation into plasma cells in a T-dependent or independent manner.

Effector B Cell

An effector B cell is often synonymous with an antibody secreting plasma cell, a type of short-lived B cell which secretes antibodies specific to a particular antigen as well as a plethora of cytokines to engage other cells of immune systems.

Memory B-Cell

A memory B cells is a long-lived B cell formed from an activated B cell that is specific to the antigen encountered during the primary immune response and capable of quick response following a second exposure to the same antigen.

Plasma Cell

A plasma cell is a terminal post-mitotic, short-lived cell of immune system, which differentiates from a B cell upon stimulation by $CD4^+$ lymphocyte (Th cells) and secretes a large amount of antibodies.

Plasticity

The term "plasticity" refers to the ability of a cell with a given genotype to change its phenotype, the change may be in response to changes in the environment.

Pre-T Cell

Pre-T cell is a developing T cell at the stage when VbDbJb is complete and TCR beta chain is expressed in a double negative ($CD4^-CD8^-$) T cell ($CD3^+$).

Immature T Cell

An immature T cell is a developing T cell which has migrated from bone marrow to thymus but has not completed the re-arrangement of its TCR, or selection for its TCR binding capacity to self-peptides presented in the context of self-major histocompatibility complex (MEC) molecules or undergone commitment to the T killer or T helper lineages which correlate precisely with a cell's TCR specificity towards MHC class I or II molecules, respectively. Lineage commitment is marked phenotypically by the loss of expression of one of the co-receptor molecules, CD8 or CD4.

Naïve T cell

A naïve T cell is a mature T cell that has differentiated in bone marrow, and successfully undergone the positive and negative processes of central selection in the thymus with re-agreement of its TCR and loss of one of the co-receptor molecules but not has yet encountered cognate antigen in the periphery.

Activated T Cell

An activated T cell is a T cell that, through engagement of both TCR and CD28 on the cell surface by the Major Histocompatibility complex peptide (peptide:MHC complex) and B7 family members on the antigen presenting cells respectively, is set on becoming an antigen-specific effector T cell.

Effector T Cell

An effector T cell is a type of short-lived T lymphocyte that is able to respond immediately upon contact with cells bearing the appropriate peptide:MHC complex for the cell.

Transdifferentiation

The term "transdifferentiation" refers to a process which takes place when a non-stem cell of particular type transforms into a different type of cell or when an already differentiated stem cell creates cells outside its already committed differentiation pathway.

BRIEF DESCRIPTION OF THE FIGURES

FIG. 24A shows the loss of the CD19 expression by such cells with simultaneous acquisition of CD3 expression whereas FIG. 24B confirms the expression of CD54 by CD3 positive T cells.

DESCRIPTION OF THE INVENTION

A preferred embodiment of the invention is further described by the following non-limiting examples with reference to the accompanying figures.

EXAMPLE 1

1. Cell Selection, Cell Manipulation and Single-Cell Cloning

The following examples describe cell preparations including selection and isolation (or sorting) of mammalian cell lines and primary cells used for the creation of HTS. The choice of particular selection technique to obtain pure population of cells with specific characteristics or use of a particular marker (or markers) for the isolation of the cells of a particular phenotype is not in anyway restrictive but rather indicative. Other cellular markers or sorting procedures can be used to deliver similar results.

1.1. Selection of Cells from Immortal Human Cell Lines

All immortal cell lines (see below) were grown in suspension culture under standard (normal) conditions in a $CO_2$ incubator at 37° C. in humidified 5% $CO_2$ atmosphere using modified RPMI1640 (Roswell Park Memorial Institute medium) with $NaHCO_3$ (JRH Biosciences), 20 mM Hepes (Sigma), 4 mM L-glutamine (Sigma) and supplemented with 10% Foetal calf serum, FCS, (JRH Biosciences). Unless stated otherwise, the tissue culture medium (TC medium)

described here is the standard medium to culture all the immortal cell lines, primary cancer cells, primary cell cultures and established tri-hybrid cell lines for the present invention. In general, all the cell lines, primary cancer cells and primary cells used were cultured in antibiotics-free environment. However, when there was a suspicion of a high risk of bacterial and/or fungal contamination, 2% penicillin (5000 units)/streptomycin (5 mg) solution (Sigma) was included in the standard medium.

Human cell lines used in this invention are as follows: — Common myeloid progenitor lineage, K562 (a cell line derived from a human chronic myelogeous leukaemia), T lymphoid lineage, MOLT4 (human T lymphoblast) and B lymphoid lineage, WIL2NS (human B lymphoblast).

1.1.1. Single-Cell Delivery System

Figure 27:
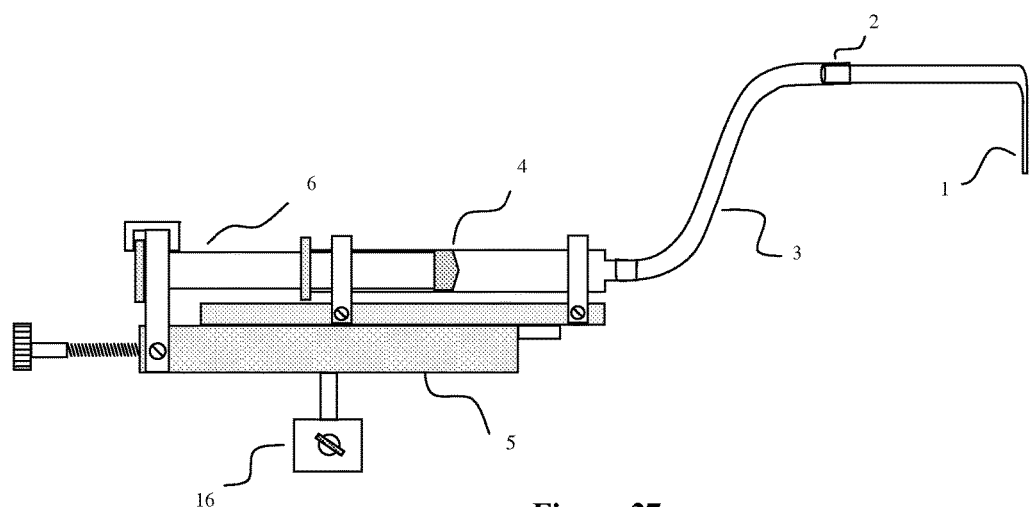
FIG. 27. A single-cell manipulation/delivery system.
Figure 28:
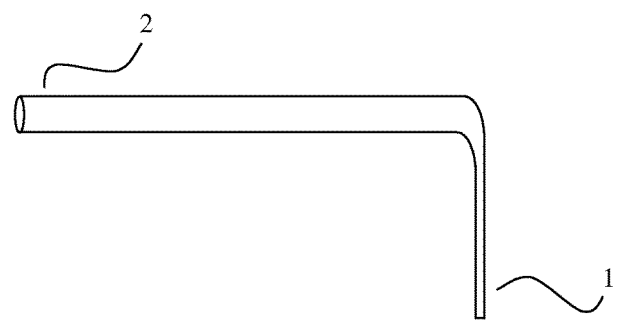
FIG. 28. A glass micro-pipette.

Cell isolation or sorting, cell manipulation and single-cell cloning are essential processes throughout this invention. Here we describe a single-cell delivering system which was established for manipulating and/or cloning a single cell of interest. The cell delivery system (FIG. 27) consists mainly of a glass micro-pipette, a 1 ml syringe and a one-dimensional coarse manipulator. FIG. 28 shows a glass, L-shape micro-pipette used for picking up a single cell of interest. The pipette was made of a haematocrit capillary tube, 75 millimeters (mm) in length, with an outer and an inner diameter of 1.5 mm and 1.10 mm, respectively. By using heat, one end of the tube was pulled such that the tip (1) with an inner diameter of approximately 250-300 micrometers (μm) and the wall of the tip of approximately 30 μm thick was obtained. The other end of the micro-pipette remained unmodified (2). In the cell delivery system (FIG. 27), a syringe (4) is mounted on a coarse manipulator, which is in turn mounted on a magnetic stand (16). The system works in such a way that the plunger (6) of the syringe can be forced to move very slowly, either forward or backward relatively to the syringe. In order to manipulate a single cell of interest, the syringe must be connected to the unmodified end of the micro-pipette (2) as shown in the figure using a flexible, medical grade tube (3). The single-cell delivering system must be sterilised by flushing several times with 70% alcohol and finally filled up without air bubbles with an appropriate tissue culture medium or solution, whatever needed, prior to any cell manipulation.

1.1.2. Single-Cell Cloning

Clones of cells from each cell line were established by single cell cloning. A technique of cloning or manipulating a single cell of any biological cells, for example, cells of K562 cell line, used in this invention is described below.

5 μl of cell suspension of K562 cells were taken out from its culture at the log-phase and deposited into a well of a tissue culture 96-well plate (TC plate, Becton and Dickinson or BD), which contained 150 μl of TC medium. The well was designated a "cell-storing well". The plate was placed on an XY microscope stage of an inverted microscope (Axiovert 40C, Carl Zeiss). Prior to single cell manipulating/cloning process, a micro-pipette (FIG. 28) was completely filled up with TC medium without air bubbles. The micro-pipette, the tubing and the syringe of the single-cell delivery system (FIG. 27) were mounted on a one-dimensional coarse manipulator (5) (Narishege). The micro-pipette tip (1) was arranged in such a way that the tip was located in the centre of the optical view of the microscope. To manipulate and clone a single cell of K562, the micro-pipette was inserted into the cell-storing well. By moving the plunger of the syringe very slowly in a sucking direction, a single cell of K562 was deposited in the micro-pipette. The micro-pipette was retracted from the cell-storing well. By moving the microscope stage laterally from the cell-storing well to an adjacent well, designated "a cloning well", and by subsequently inserting the micro-pipette into this cloning well, the single cell in the micro-pipette was then gently released from the micro-pipette. This was achieved by moving the plunger of the syringe very slowly in a releasing direction. The process of withdrawing a single cell from the cell-storing well and depositing the single cell into the cloning well was repeated numerous times until 60 single-cell clones per TC plate were obtained. The cloning plate was incubated in a humidified incubator (Thermoline Scientific), operated at 37° C. with 5% $CO_2$, for a period of 10 days. The medium in each cloning well was replenished with fresh TC medium regularly during the incubation period. Cell proliferation of each clone from each cloning well was recorded every 24 hours. At the end of the incubation period, a number of clones of K562 cells were established. A clone with the highest proliferation rate or the highest level of a marker of interest that expressed on the cell surface, for example, CD71 transferrin receptor on K562 cells, was selected for establishment of HTS or further experiments.

1.1.3 Sorting of $CD71^+$ Cells

As an example, the method below describes a cell selection and sorting of CD71 positive cells of myelomonocytic lineage from K562 cell line using a fluorescence-activated cell sorter (FACS).

Figure 1:
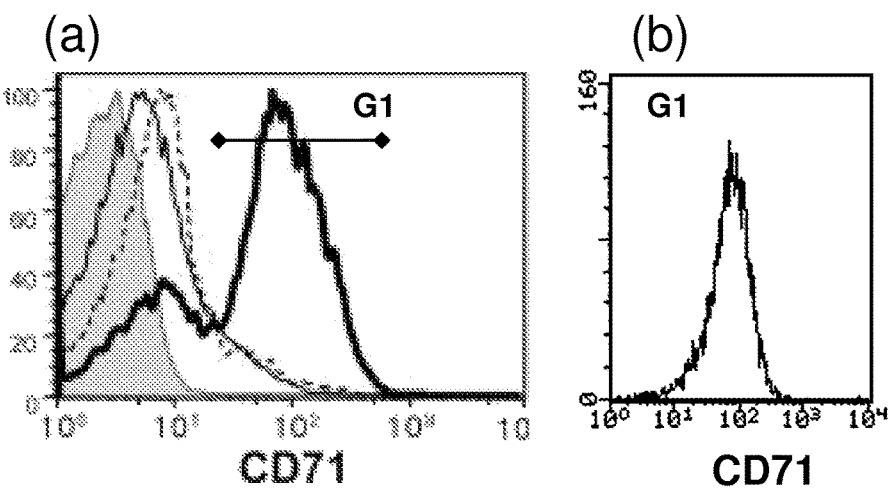
FIG. 1. Identification and sort-purified $CD71^+$ K562 cells.

For this purpose, $1 \times 10^5$ K562 cells suspended in 100 μl of a phosphate buffer solution (Dulbeco PBS) containing 2% bovine serum albumin, BSA, (Sigma) were incubated in the dark with 20 μl of either phycoerythrin (PE) conjugated anti-CD71 (BD Pharmingen) or PE conjugated isotypic control antibodies IgG2a, κ (BD Pharmingen) for 30 minutes at room temperature. The incubation mixture was diluted with 1 ml of PBS and the stained cells were collected by centrifuging at 300 g for 10 minutes. Following an additional wash with 1 ml of PBS, the stained cells were suspended in 1 ml of PBS and analysed immediately using a FACS (BD FACSCalibur). FIG. 1 shows profiles of $CD71^+$ cells of K562 cell line. The $CD71^+$ positive cells were gated and sorted out (FIG. 1a). Approximately, 65% of original K562 population were positive for CD71. The sorted cells were centrifuged at 300 g for 10 minutes and suspended in 1 ml of PBS for further experiments. 100 ml of suspended $CD71^+$-sorted cells were collected for purity analysis as shown in FIG. 1b. A purity of 99% of $CD71^+$ sorted cells was obtained. Following cell sorting, the $CD71^+$ cells of K562 cell line were either used for further experiments or placed in the culture under standard culture conditions and marked as CD71 enriched K562 cells. The same methodology was used to establish CD71-enriched WIL2NS and CD71-enriched MOLT4 cultures.

1.2 Isolation of Myelomonocytic Cells

Myelomonocytic progenitor cells can be derived from any immortal myelomonocytic cell lines or from primary haematopoietic tissues such as bone marrow. Below are examples of isolating myelomonocytic progenitor cells from human myeloid cell line K562 and from bone marrow samples.

1.2.1 Selection of Myelomonocytic Cells from $CD71^+$ K562 Culture

To ensure the myelomonocytic phenotype of the cells for cell hybridisation experiments, $CD71^+$ K562 cells were further enriched for $CD15^+$ cells using FACS analysis and followed by sorting.

CD71-enriched K562 cells described in Section 1.1.3 were labelled with PE anti-human CD71 and FITC anti-human CD15 (BD Pharmingen). $1 \times 10^5$ washed CD71-enriched K562 cells suspended in 100 µl of PBS containing 2% BSA were incubated in the dark with 20 µl of either anti-human CD71-PE and anti-human CD15-FITC antibodies or negative isotypic control antibodies or FITC and PE labelled negative isotypic control antibodies for 30 minutes at room temperature. The incubation mixture was diluted with 1 ml of PBS and the stained cells were collected by centrifuging at 300 g for 10 minutes. Following an additional wash with 1 ml of PBS, the stained cells were suspended in 1 ml of PBS and analysed immediately using a FACS Calibur (BD).

Figure 2:
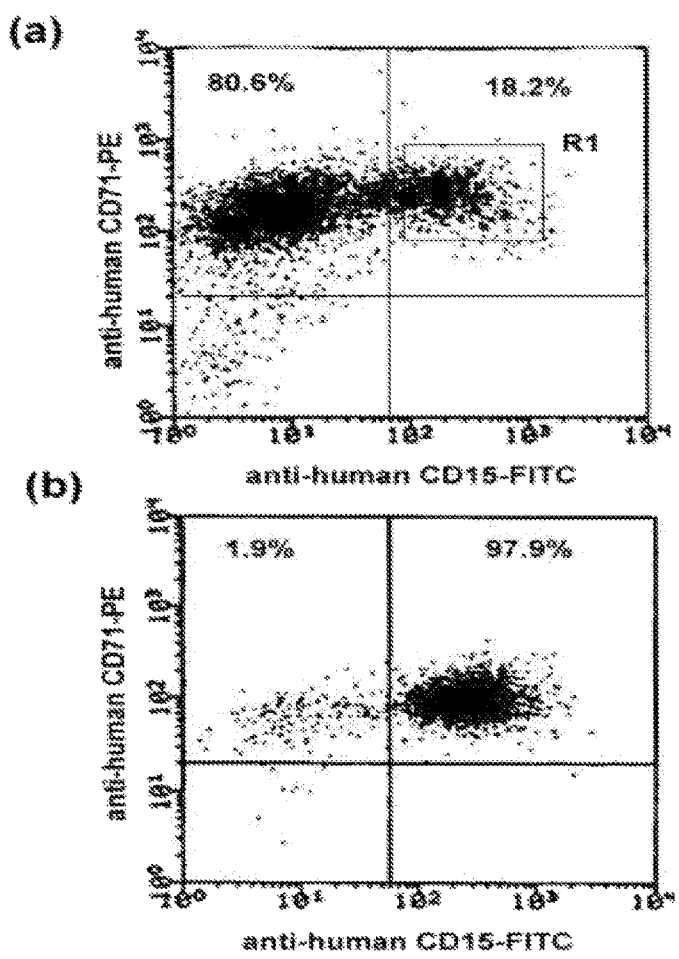
FIG. 2. FACS profiles of CD15 and CD71 positive K562 cells; (a) approximately 18% of original CD71-enriched K562 cell population were positive for CD15 (R1 region) and (b) re-analysis of CD15 positive K562 cells following two months in culture.

A typical FACS profile is shown in FIG. 2a. After 5 months in the culture, 99% of the CD71-enriched K562 cells remained positive for CD71, which approximately 18% expressed surface CD15. The cells positive for both CD71 and CD15 were gated (FIG. 2a) and sorted out. The sorted cells were collected by centrifuging at 300 g for 10 minutes and suspended in 1 ml of PBS for further experiments. 100 µl of suspended $CD71^+CD15^+$ sorted cells were collected for purity analysis. Following two months culture, the sorted cells were re-analysed for co-expression of CD71 and CD15 (FIG. 2b). The results indicate that that approximately 98% of the purified cells retained both CD 71 and CD15. It was found that some of the cells which earlier expressed both CD71 and CD15 on the surface had lost their CD15 expression (FIG. 2b) suggesting that commitment to myelomonocytic lineage in K562 cells is not stable and reversible.

1.2.2 Selection of Uncommitted and Myelomonocytic Progenitor Cells from Primary Cells As an example, the method below describes the selection of uncommitted cells or cells of the myelogenous lineage from bone marrow samples obtained from patients with acute myelogenous leukaemia (AML). The same method could also be applied to select cells of other lineages from bone marrow samples of corresponding blood malignancies.

Bone marrow aspirates from patients with AML were obtained after informed consent. The samples were extracted from the patients whose diagnosis of AML was established prior to conducting experiments. AML mononuclear cells were isolated using the same density gradient centrifugation procedure as described in Section 1.3.1, and $CD34^+$ cells from the samples were sorted or isolated using a FACS.

To stain or label the mononuclear cells obtained above, 10 µl of a mouse anti-human CD34-PE antibody (BD Pharmingen) or a PE isotype control antibody (BD Pharmingen) were added to 100 µl of a given aliquot of $1\times10^6$ mononuclear cells in a staining medium (PBS+5% BSA). For a given aliquot, the staining mixture was incubated for 30 minutes on ice. 10 ml of ice-cold staining medium was added to the cell pellet and centrifuged for 7 min at 350 g and 4° C. Supernatants were aspirated and then the cell pellet was resuspended by flicking the tube in which a comparable volume of ice-cold staining medium was added. The stained cells were centrifuged and washed once more in ice-cold staining medium. The labelled cells were suspended in staining medium and applied to FACS. After setting appropriate sorting gates for $CD34^+$ cell population, the cell fractions were collected. The $CD34^+$ cells were either used straight away or placed in the culture for enrichment of myelomonocytic cells.

For enrichment cultures, $40\times10^3$ cells of the $CD34^+$-enriched cells were plated in 12 well plates pre-coated with synthetic extracellular matrix. The cells were expanded in complete TC medium supplemented with 57 mM of β-mercaptoethanol (Sigma), 1 mM hydrocortisone and 20 ng/ml of human interleukin-3 (IL-3) and human granulocyte colony-stimulating factor (G-CSF). After 48 hours in the culture, the cells were further selected for CD15 expression using FACS.

For fluorescence-cell staining, a mouse anti-human CD15-FITC (BD Pharmingen) and a mouse anti-human CD34-PE (BD Pharmingen) were used and a similar cell staining method described earlier in this Section was also employed. The stained samples were analysed using a FACS. After setting appropriate sorting gates for CD34 and CD15 positive cell population ($CD34^+CD15^+$) or for CD34 positive and CD15 negative cell population ($CD34^+CD15$), the fractions were collected.

Figure 3:
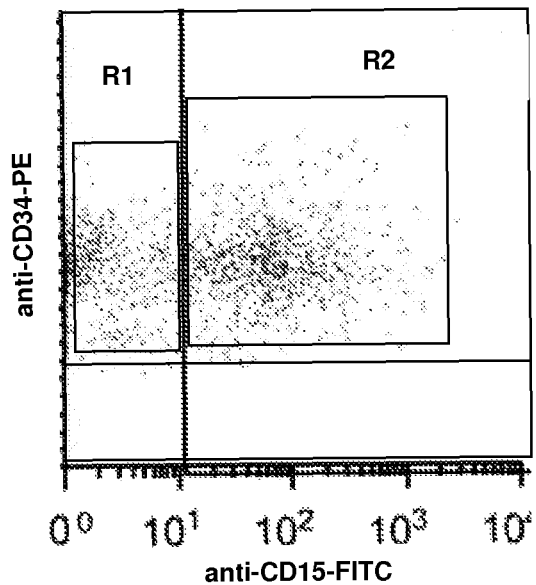
FIG. 3. Sorting of $CD34^+$ and $CD34^+CD15^+$ cells from the $CD34^+$ enriched AML mononuclear cells after 48 hours in the culture.

The typical expression profile and sorting gates for $CD34^+$ cells and for CD15 expression on the $CD34^+$ AML cells after 48 hours in culture is shown in FIG. 3. Approximately, 54% of AML mononuclear cells tested positive for CD15 whilst maintaining their CD34 expression, whereas the rest of the cell population retained its CD34 expression without committing to myelomonocytic lineage. The $CD34^+CD15^+$ cells were used in experiments for creating a trans-differentiation system, while uncommitted $CD34^+$ cells were used for de-differentiation experiments.

1.3 Isolation of Lymphocytes

For the establishment of a transdifferentiation system, the lymphocytes can be derived either from any type specific immortal cells or from primary lymphocytes. The preparation of B and T lymphocytes derived from immortal WIL2NS and MOLT4 cell lines, respectively, was described in Section 1.1.3. The primary lymphocytes can be isolated from any lymphoid tissues such as peripheral blood, cord blood, spleen, bone marrow, thymus, tonsils, and regional lymph nodes. As a first step, all lymphoid tissues were processed to isolate mononuclear cells.

1.3.1. Isolation of Human Mononuclear Cells from Bone Marrow, Peripheral Blood or Umbilical Cord Blood Peripheral blood samples were collected from healthy individuals after informed consent. Each blood sample was collected in heparinised tubes (Vacutainer, BD), pooled, and diluted in RPMI1640.

Human bone marrow aspirates were obtained from patients who underwent bone marrow biopsies and had normal bone marrow without any blood abnormalities. The samples were diluted at a ratio of 1:3 with RPMI1640.

Human umbilical cord blood samples were obtained from normal full-term vaginal deliveries after informed consent. Each cord blood was collected with a heparinised 60 ml syringe after delivery of the infant and ligation of the cord, prior to expulsion of the placenta. Each sample was diluted in RPMI1640.

Peripheral blood mononuclear cells (PBMCs), bone marrow mononuclear cells (BMMCs) and umbilical cord blood mononuclear cells (UCBMCs) were prepared by density centrifugation over Ficoll-Paque (Amersham Pharmacia). In brief, 10 ml of Ficoll-Paque were layered under 20 ml of cell suspension using cannulae tube attached to a 20 ml syringe. The sample cells were centrifuged at 1,700 rpm (700 g) for 40 minutes at 4° C. The cells in the interface were collected and washed in 50 ml of RPMI1640 by centrifugation at 2,000 rpm (1,000 g) for 10 minutes. The supernatant was discarded and pelleted cells were re-suspended in 40 ml of RPMI1640 and centrifuged at 1,300 rpm (400 g) for 10 minutes. The red blood cells and platelets were removed by lysis with 0.83% (wt/vol) $NH_4Cl$ and a second centrifugation over Ficoll-Paque diluted at a ratio of 1:2 with PBS, respectively.

The isolated mononuclear cells were used for culturing or analysis and sorting into cell specific fractions through a FACS.

1.3.2. Isolation of Human Mononuclear Cells from Solid Lymphoid Tissues

The method below describes the procedure used in this invention for isolating mononuclear cells from spleen. The same method can be used for isolating mononuclear cells from thymus, tonsil or regional lymph nodes. A method for cell staining and sorting is also given.

Spleen samples were obtained from organ transplant donors following the national ethical guidelines. Blocks of spleen, approximately 2×2×3 cm each, were kept at 4° C. in RPMI 1640 until isolation of the splenocytes. Each block was cut into small pieces through the mesh of a sterile sieve using the plunger of a syringe. The cells were then dissociated enzymatically by digestion with 20 U/ml type VII collagenase (Sigma) and 20 U/ml DNase (Sigma) in complete medium for 30 minutes at room temperature. The cell aggregates were further dissociated by the addition of EDTA to attain 10 mM and agitation for 5 minutes at room temperature. The splenocytes were then washed with complete medium twice to stop enzymatic digestion and re-suspended in RPMI 1640. These conditions did not affect surface molecule expression compared to non-enzymatic dissociation procedures (McIlroy et al 1995). Spleen mononuclear cells were isolated from these splenocyte suspensions by density gradient centrifugation as described in Section 1.3.1 except for the removal of red blood cells. The spleen mononuclear cells were re-suspended in RPMI1640 and cell concentration was adjusted to $1\times10^6$ cells per ml. Cell viability was above 98% as determined by trypan blue exclusion.

1.3.3. Isolation of Mature B Cells and Helper T Cells from Human Spleens and Peripheral Blood The tissue samples were initially processed to extract the mononuclear cell population as described in Section 1.3.1 and Section 1.3.2. Fluorescence-cell staining followed by cell sorting was then performed within 4 hours of the isolation of the mononuclear cell population. The cells were suspended in complete medium under standard culture conditions (see Section 1.1) until staining.

Below are examples of staining and sorting of B and T cells from primary cells. Usually, the selections of B cells and helper T cells were based on the surface expressions of CD19 and CD4, respectively.

In brief, 10 µl of each of mouse anti-human CD19-FITC conjugated antibody (BD Pharmingen) and mouse anti-human CD4-PE conjugated antibody (BD Pharmingen) or appropriate isotype control were added to a 100 µl aliquot of mononuclear cells in staining medium (PBS+5% BSA), containing $1\times10^5$ cells per aliquot. For a given aliquot of mononuclear cell population, the staining mixture was incubated for 30 minutes on ice. 10 ml of ice-cold staining medium were added to the staining mixture and centrifuged for 7 minutes at 350 g and 4° C. The supernatant was aspirated and then the cell pellet was re-suspended by flicking the tube on which a comparable volume of ice-cold staining medium was added. The stained cells were centrifuged and washed once more in ice-cold staining medium. The process was repeated for other aliquots. The stained cells were analysed using a FACS. At least 20,000 gated events were analysed for each sample. After setting appropriate sorting gates for CD19 positive B cell population ($CD19^+CD4^-$) or for CD4 positive T cell population ($CD4^+CD19^-$), the fractions were collected. 1 ml of each fraction was collected for purity analysis and the rest of each fraction was re-suspended in complete medium for further experiments.

A small number of cells ($\leq 5\times10^5$ cells) were sorted directly into microcentrifuge tubes with appropriate adapters. Prior to sorting, a small volume (0.1 to 0.2 ml) of supplemented RPMI1640 was added to the recovery tubes in order to mix with the sorted sample and improve viability of sorted cells. After sorting, provided the number of recovered cells permitted, 20 µl of each sorted cell sample was diluted at 1:10 with staining medium for re-analysis to verify its purity. An acceptable purity was $\geq 95\%$. Further 20 to 40 µl of FCS per ml of sorted sample were added and followed by centrifugation for 7 min at 350 g, 4° C. The cells were then re-suspended in the standard tissue culture medium. If sufficient cells were available, they were counted to determine yield.

A FACS profile of spleen samples labelled with anti-human CD19-FITC and anti-human CD4-PE is shown in FIG. 10a, whereas the profiles of purity analysis of sorted $CD19^+$ B cells and $CD4^+$ T cells are shown in FIGS. 10b and 10c. The cell purity in the fractions exceeded 98% for $CD19^+$ cells and 96% for $CD4^+$ cells.

The sorting and purity profiles for $CD19^+$ and $CD4^+$ cells from peripheral blood were essentially similar to those from spleen samples, only fewer numbers of each cell population were obtained.

1.3.4. Isolation of CD5 Positive (Antigen-Experienced) B Cells and CD5 Negative (Naïve) B Cells from Human Umbilical Cord Blood Mononuclear cells were prepared from umbilical cord blood samples as described in Section 1.3.1. Fluorescence-cell staining followed by cell sorting was performed within 4 hours of the isolation of mononuclear cell population. In this particular example, sorting of CD5 negative (naïve) B cells and CD5 positive (antigen-experienced) B cells from human umbilical cord blood, was carried out using a mouse anti-human CD5-FITC antibody (BD Pharmingen), a mouse anti-human CD19-PE antibody (BD Pharmingen) or appropriate isotype control according to the method described previously (Section 1.3.3).

Figure 4:
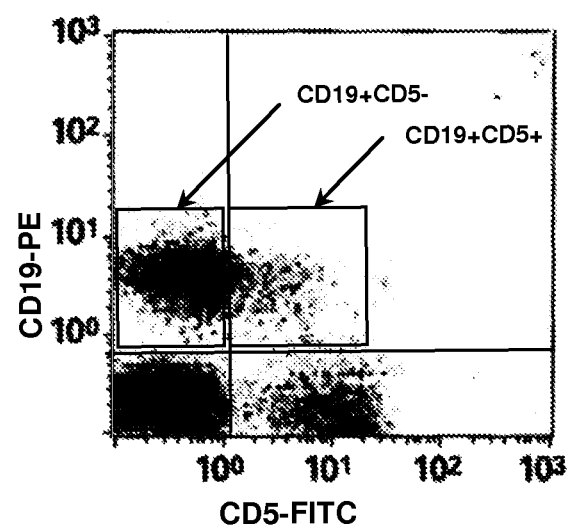
FIG. 4. A FACS profile of umbilical cord blood mononuclear cells stained with mouse anti-human CD19 and mouse anti-human CD5 antibodies.

The stained samples were analysed using a FACS. At least 20,000 gated events were analysed for each sample. After setting appropriate sorting gates for CD5 negative B cell population ($CD19^+CD5^-$) or for CD5 positive B cell population ($CD19^+CD5^+$) population, a number of fractions were collected. FIG. 4 shows a typical profile of the samples stained with mouse anti-human CD19 and mouse anti-human CD5.

The percentage of B cells in the sample ranged from 4 to 19.2% and $CD5^+$ B cells ranged from 0.8 to 7.2% of total circulating lymphocytes.

Figure 5:
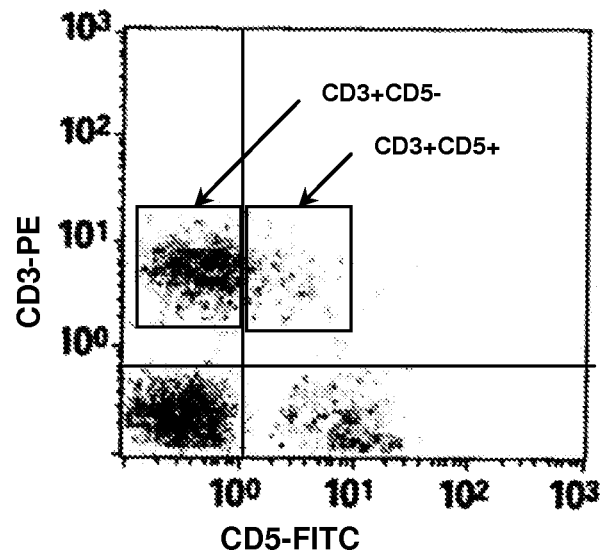
FIG. 5. A FACS profile of mononuclear umbilical cord blood cells stained with mouse anti-human CD3 and mouse anti-human CD5 antibodies.

1.3.5. Isolation of CD5 Positive (Antigen-Experienced) T Cells and Cd5 Negative (Naïve) T Cells from Human Umbilical Cord Blood Mononuclear cells were extracted from umbilical cord blood samples using a similar method as described in Section 1.3.1. Fluorescence-cell staining followed by cell sorting was performed within 4 hours of the isolation of mononuclear cell population. In this particular example for sorting of CD5 positive (antigen-experienced) T cells and CD5 negative (naïve) T cells from human umbilical cord blood, was carried out using a mouse anti-human CD5-FITC antibody (BD Pharmingen), a mouse anti-human CD3-PE antibody (BD Pharmingen) or appropriate isotype control according to the method of cell described previously (Section 1.3.3). The stained cells were analysed using a FACS. At least 20,000 gated events were analysed. The sorting gates were set to collect fractions containing either CD5 negative T cells ($CD3^+CD5^-$) or CD5 positive T cells (CD3$^+$CD5$^+$). FIG. 5 shows a typical profile of the samples stained with mouse anti-human CD3 and mouse anti-human CD5 antibodies.

Effectively, the same method used to recover and analyse the sorted populations has been described in Section 1.3.3.

The percentage of T cells in the samples ranged from 1.7 to 13.5% and CD5$^+$ T cells ranged from 0.4 to 1.3% of total circulated lymphocytes.

Figure 6:
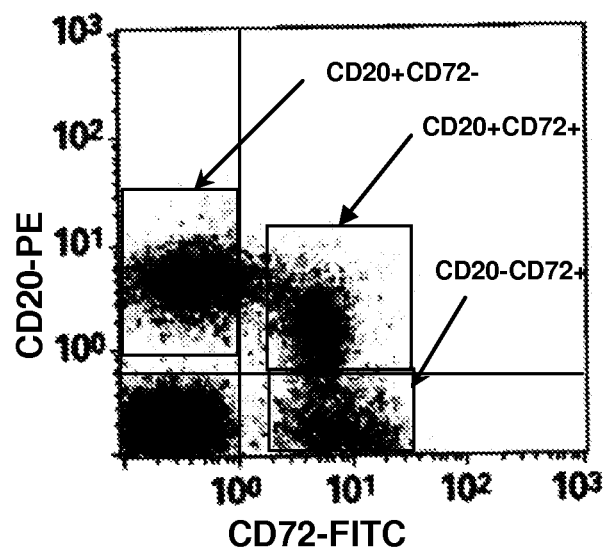
FIG. 6. A FACS profile of bone marrow mononuclear cells stained with mouse anti-human CD20 and mouse anti-human CD72 antibodies.

1.3.6. Isolation of Early B Cells, Activated and Resting B Cells Based on CD 20 and CD 72 Expressions from Human Bone Marrow Mononuclear Population Mononuclear cells were extracted from bone marrow using the method described previously (Section 1.3.1). The fluorescence-cell staining followed by cell sorting was performed within 4 hours of the isolation of mononuclear cell population. Staining and sorting the activated B cells is described previously in Section 1.3.3. Specifically, 10 µl of a mouse anti-human CD72-FITC antibody (BD Pharmingen) and 20 µl of a mouse anti-human CD20-PE antibody (BD Pharmingen) or appropriate isotype control (PE mouse IgG2b, κ antibodies) were used. The stained cells were analysed using a FACS. The sorting gates were set to collect fractions containing either CD20 positive population comprising pre-B cells, resting and activated B cells, follicular dendritic cells (CD20$^+$CD72$^-$) or CD72 positive cell population comprising early B cells (CD20$^-$CD72$^+$) or activated B cells (CD20$^+$CD72$^+$). FIG. 6 represents a typical profile of the samples stained with mouse anti-human CD20 and mouse anti-human CD72 antibodies.

Effectively, the same method as described in Section 1.3.3 was applied to recover and analyse sorted cells.

Typically, approximately 10-15% of bone marrow mononuclear cell population was positive for both CD20 and CD72; 9-12% of cells were positive for CD20 but negative for CD72; and approximately 8% were positive for CD72 only.

1.3.7. Isolation of Thymocyte Subpopulations by Magnetic Bead Sorting

Using the MACS CD4 Multisort kit (Miltenyi Biotec GmbH), CD4$^-$CD8$^-$ double negative thymocytes, CD4$^+$CD8$^+$ double positive thymocytes, and CD4$^+$ and CD8$^+$ single positive thymocyte cell populations were sorted out according to the manufacturer's instructions. Briefly, thymocytes collected using a similar method as that described in Section 1.3.2 were incubated with CD4 Multisort CD4 microbeads for 30 minutes. After washing with 5 mM EDTA and 0.5% BSA in PBS, the labelled cells were separated on magnetic columns. The positively selected thymocytes, which were retained on the magnetic column, contained CD4$^+$ single positive and CD4$^+$CD8$^+$ double positive cell populations, whereas the CD4 depleted cell population, which was eluded through the column, contained CD8$^+$ single positive and CD4$^-$CD8$^-$ double negative cells. To remove microbeads from the CD4 positively selected cell populations, the cells were incubated with MACS Multisort release reagent. After 20 minutes, the digestion was stopped, and the cells were labelled for 30 minutes with CD8 microbeads. The CD4$^+$CD8$^+$ double positive thymocytes were obtained by positive selection, whereas CD4$^+$ single positive cells were found in the depleted cell population. The CD4 depleted cell population was incubated for 30 minutes with CD8 microbeads. After applying labelled cells on a magnetic column, CD8$^+$ single positive cells could be separated from the CD4$^-$CD8$^-$ double negative thymocytes. The purities of the four different thymocyte subpopulations were evaluated by flow cytometric analysis. The accepted purity was more than 95%.

1.3.8 Isolation of CD54$^+$ T Cells from Human Tonsils.

Figure 7:
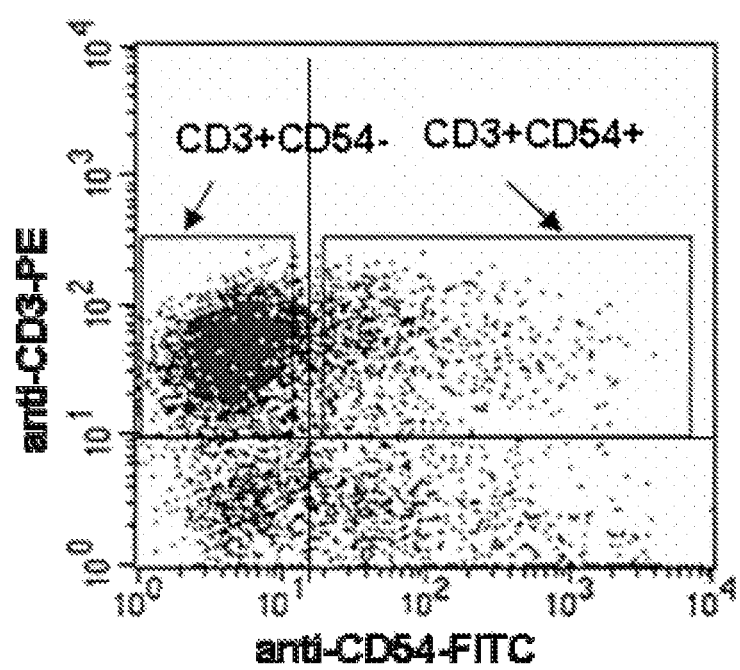
FIG. 7. A typical FACS profile of tonsilar mononuclear cells stained for CD3 and CD54.

Mononuclear cells were extracted from human tonsils using the method described in Section 1.3.2. The fluorescence-cell staining followed by cell sorting was performed within 4 hours of the isolation of the mononuclear cell population. CD54$^+$ T cells (intercellular adhesion molecule-1 or ICAM-1) were extracted from the mononuclear tonsillar cell population, using a mouse anti-human CD3-PE antibody (BD Pharmingen) and a mouse anti-human CD54-FITC antibody (BD Pharmingen) or an appropriate isotype control were chosen using the cell staining/sorting method as described in Section 1.3.5. The stained cells were analysed using a FACS. The sorting gates were set to collect fractions containing either CD3$^+$ T cells (i.e. CD3$^+$CD54$^-$ cells) or activated CD54$^+$ T cells (i.e. CD3$^+$CD54$^+$ cells). FIG. 7 shows a FACS profile of the samples stained with mouse anti-human CD3 and mouse anti-human CD54 antibodies. The CD3$^+$ cells were used for the creation of HTS, whereas CD54$^+$ activated T cells were used for transdifferentiation experiments.

The results showed that whilst T cells constituted the majority (82%) of mononuclear cells isolated from tonsils, only 9% were CD54$^+$ T cells.

1.4. Generation and Selection of Human Lymphocytes Secreting IgM and IgG

Purified B cells (see Section 1.3.3) were seeded at 3.75× 10$^5$ cells/ml in wells of 96 round bottom well plates (Corning) coated with mouse anti-human CD154 antibody (BD Pharmingen). The cells were cultured in complete RPMI1640 medium supplemented with 10% heat inactivated ultra-low IgG Foetal Bovine Serum, FBS, (Gibco/BRL) and 100 U/ml of human interleukin 4 (IL-4) (R&D systems) and 50 ng/ml of human interleukin 10 (IL-10) added after day 3 in the culture. The cultures were replenished by replacing half of the culture medium every 2 to 3 days. Cell viability and counts were evaluated in triplicate by trypan blue exclusion using a hemocytometer. At day 5 and day 10, cultured lymphocytes were harvested, washed twice in PBS and analysed by FACS using mouse anti-human CD19-PE, mouse anti-human IgM-FITC or mouse anti-human IgG-FITC antibodies (all from BD Pharmingen). All stainings were achieved with 1 µg of each antibody per 1×10$^6$ cells at 4° C. In all of the analyses, more than 95% of cells were double-negative with markers set according to isotype-matched negative control staining. The regions containing dead cells and debris were excluded from analysis. All analyses were done by gating 5,000 to 10,000 viable cells.

Figure 8:
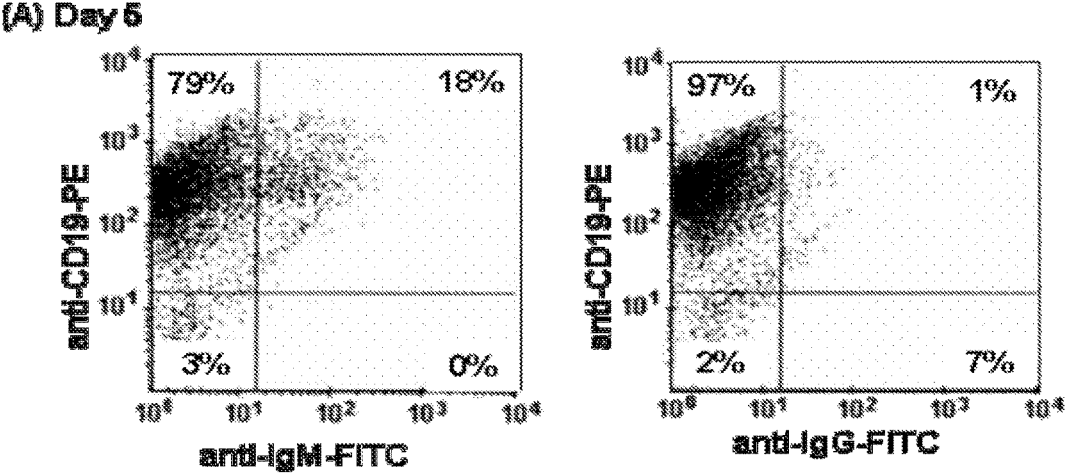
FIG. 8. The presence of IgM and IgG positive cultured lymphocytes; (A) after 5 days in the culture 18% of $CD19^+$ cells were IgM positive and only 1% had detectable IgG on the surface and (B) after 10 days, the percentage of IgM positive lymphocytes reduced to only 2% whilst the percentage of IgG positive cells increased to 15%.
Figure 8:
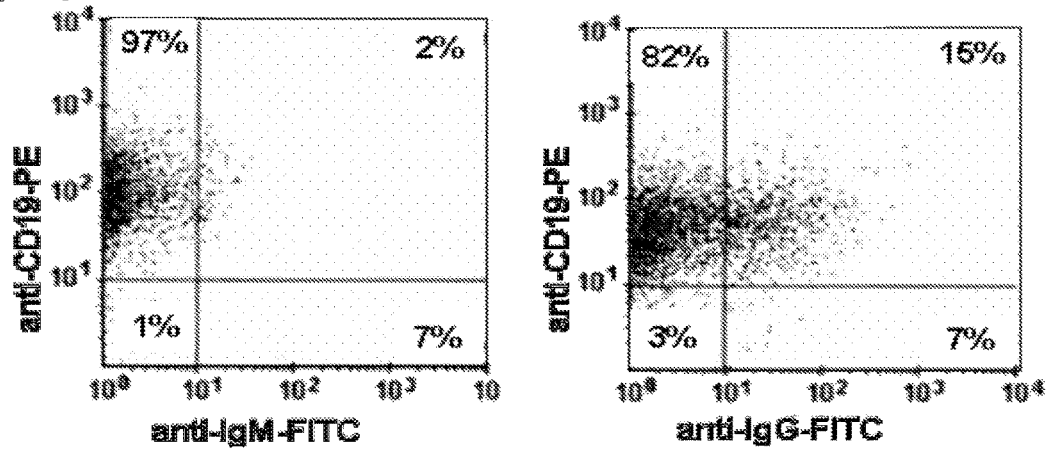

Typical profiles of IgM and IgG positive cells in the cultured lymphocytes are shown in FIG. 8. After 5 days in the culture 18% of CD19$^+$ cells were IgM positive and only 1% had detectable IgG on the surface, whereas after 10 days the percentage of IgM positive lymphocytes reduced to only 2% whilst the percentage of IgG positive cells increased to 15%. After setting appropriate gates the IgM positive and IgG positive fractions were sorted out.

IgM and IgG concentrations in the culture were determined by a standard ELISA using 96 ELISA well plates and plastic-absorbed goat-affinity-purified antibodies to human µ and γ chains. The bound antibodies were revealed with HRP-conjugated sheep anti-human Ig antibodies. All antibodies were from Sigma. ABTS was used as a substrate and optical densities were measured at 405 nm. Table 1 summarises the levels of IgM and IgG detected in the B lymphocyte culture after 5 and 10 days.

TABLE 1

Production of IgM and IgG in primary B lymphocyte culture

| Period in culture | IgM (ng/10⁶ cells) | IgG (ng/10⁶ cells) |
|---|---|---|
| 5 days | 2,480 ± 182 | 850 ± 92 |
| 10 days | 1,215 ± 260 | 1,914 ± 101 |

The production of IgM declined after 5 days in the culture whereas IgG production increased.

EXAMPLE 2

2. Somatic Cell Hybridisation

Several methods of somatic cell hybridisation are well known in the art. These include but are not limited to, for example, a biological method using fusagenic virus such as Sendai virus (Kohler and Milstein, 1975), a chemical means using polyethylene glycol (PEG) (Wojciersyn, et al, 1983), and an electrical method using electric fields (Neil, and Zimmermann, 1993). Each method can induce or cause the plasma membranes of cells of interest to be reversibly permeable and to hybridise.

Regardless of cell hybridisation methods mentioned above, two essential steps are, in principle, required in order to achieve cell hybridisation. First, the plasma membranes of the cells to be hybridised must be brought into good cell membrane contact. Second, a reversible breakdown of the plasma membranes at the point of contact must be simultaneously induced.

For the electrical cell hybridisation method, the cells of interest can be brought into good cell membrane contact by using an alternating-current electric field (AC field) with an appropriate field frequency and then be induced to hybridise when they are exposed to a short electric pulse simultaneously with the AC field.

To elaborate further, the electrical cell hybridisation involves the following physical phenomena; dielectrophoresis (DEP) and an electrical breakdown of the plasma cell membranes.

Figure 30:
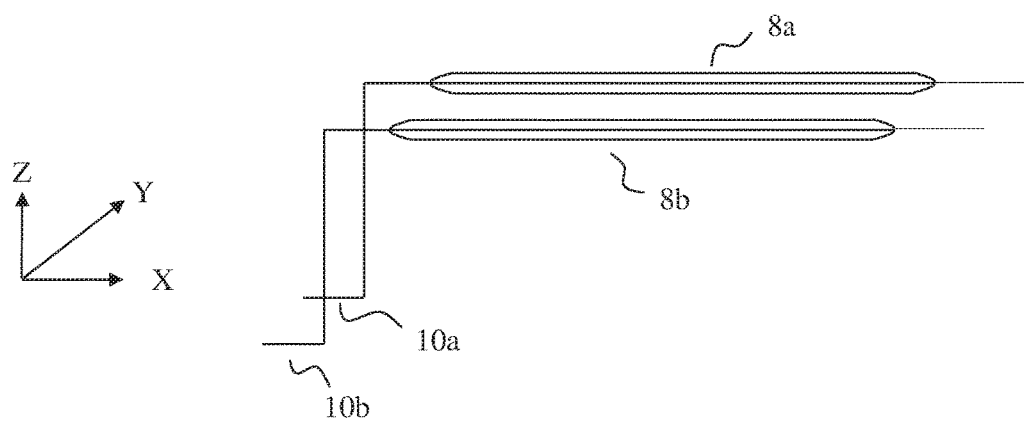
FIG. 30. Two parallel micro-electrodes.

Dielectrophoresis (Pohl 1978) is a phenomenon which describes the movement of dielectric particles such as biological cells when they are suspended in an appropriate solution and subject to a non-uniform AC electric field of an appropriate frequency. It is well documented that the movement of cells can be described as a (i) translation or migration of dielectric particles, for example at field frequencies between 0.5-2.0 megahertz (MHz) for Sp2 cells suspended in 100 mM sorbitol (Mahaworasilpa, 1992) and (ii) rotation of dielectric particles (Mahaworasilpa, 1992), for example at field frequencies between 2-10 kilohertz (kHz) for Sp2 cells suspended in 100 mM sorbitol. A non-uniform field can be generated by applying an electric field across a pair of electrodes, for instance, electrical, cylindrical wires that can be arranged in a number of configurations. The configuration most widely used is a parallel electrode configuration (FIG. 30). In the presence of a non-uniform field, DEP can cause dielectric particles (i.e. biological cells) to attract one another and simultaneously migrate towards the regions of the most intense field. As a result, it forms a chain or string of cells and, in turn, it induces good cell membrane contact. It is evident that the mutual attraction of cells is strongly promoted when the cells are suspended in solutions of moderately low electrical conductivity.

The electrical breakdown of cell membranes can be induced when the cells suspended in a suitable hybridisation solution are exposed to an electric pulse with an appropriate pulse amplitude and width (Zimmermann, 1982). A range of pulse widths, for example, square pulses of 1 to 200 microseconds (μsec) is widely used, depending upon the types of cells to be hybridised.

2.1. Electrical Cell Hybridization System

In certain embodiments of this invention, an electrical cell technique may be used to create hybridised cells, such as trans-differentiating cells.

2.1.1. Cell Manipulation System

In order to manipulate individual cells of interest prior to cell hybridisation, the single-cell manipulation/delivery system described previously (Section 1.1.1) was used throughout this invention.

2.1.2. Microelectrodes

Figure 29:
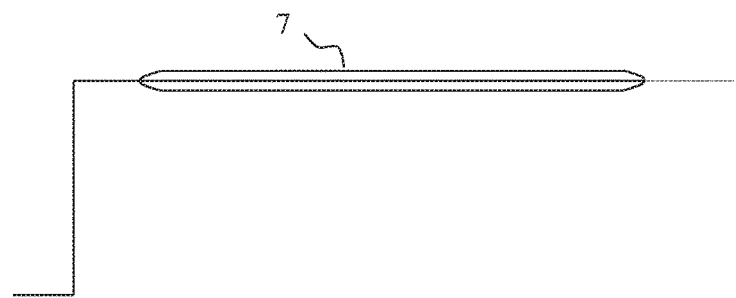
FIG. 29. A micro-electrode.

In this invention two L-shape microelectrodes were used. FIG. 29 shows a microelectrode which was made of an uncoated nickel alloy, 128 μm in diameter (7). The shaft of the microelectrode was covered with a haematocrit capillary tube, 1.5 mm outer diameter. The L-shape Section of the microelectrode was configured to allow a consistent area of the surface of both the horizontal and vertical Sections of the electrode to be exposed to a medium or an appropriate solution (Mahaworasilpa, 1992). Prior to the cell hybridisation process, two microelectrodes were mounted on two fine micromanipulators, one for each microelectrode. These microelectrodes were arranged in such a way that a parallel electrode configuration of each electrode was obtained (FIG. 30). Each fine micromanipulator was hydraulically driven and allowed movement as fine as 0.5 μm to be made in the X, Y or Z direction.

2.1.3. Cell Chamber and Configuration

Figure 31:
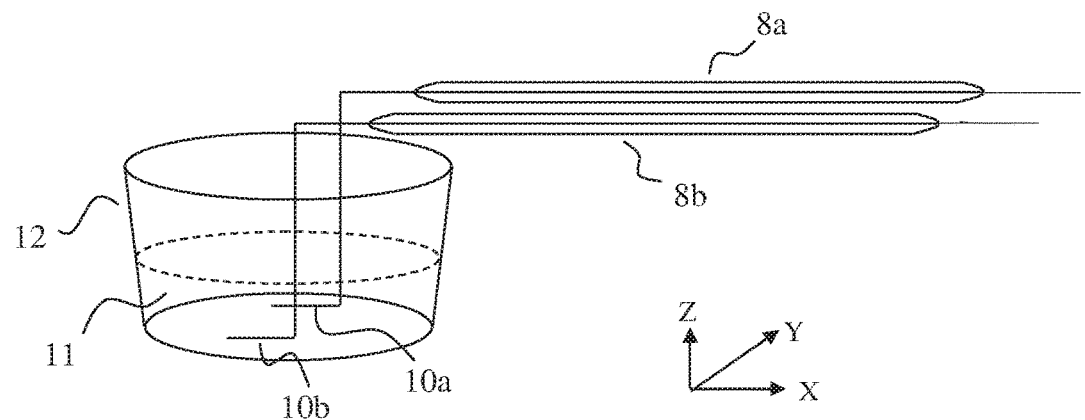
FIG. 31. Two micro-electrodes in a well of a tissue culture plate.
Figure 32:
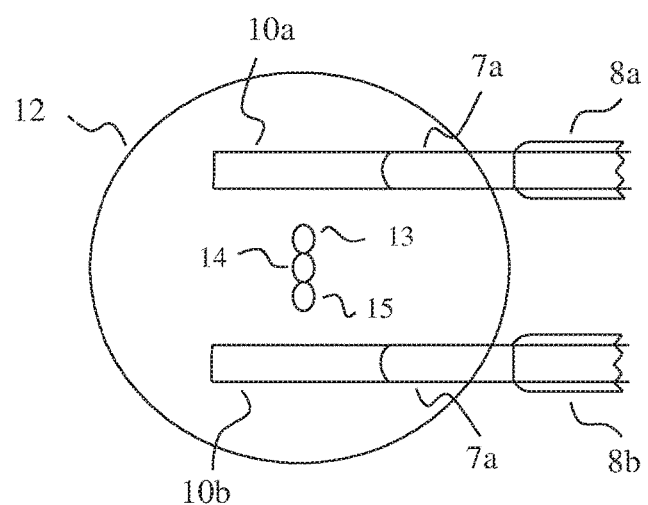
FIG. 32. A top-view of a well containing 3 cells intermediate 2 microelectrodes.
Figure 33:
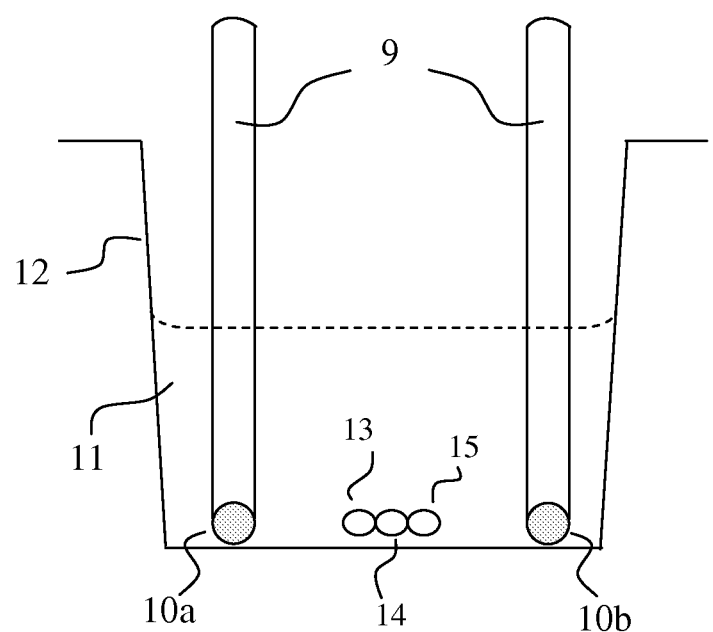
FIG. 33. A side-view of the well of FIG. 32.

FIG. 31 shows two parallel electrodes in a well of a standard 96-well-flat-bottom TC plate, the well serves as a cell hybridisation chamber in certain embodiments of this invention. To perform cell hybridisation the microelectrodes were submerged in an appropriate medium (11) contained with the well (12) of a standard 96-well tissue culture plate. FIG. 32 and FIG. 33 show a top view and a lateral-view of the parallel electrode configuration respectively, where, for example three pre-selected cells to be hybridised are placed in between the parallel electrodes in such a way that they can be induced to align or form a chain of cells in the presence of an appropriate AC electric field.

EXAMPLE 3

3. Examples of Establishing Hematopoietic Transdifferentiation Systems by Electrical Cell Hybridization Method The following Sections provide examples of the creation of haematopoietic transdifferentiation systems (HTS) obtained by hybridising cells from either different lineages or cell types or same lineages/or cell types but different phenotypes. Each stable system underwent analysis to confirm that it simultaneously possessed phenotypic characteristics of parent cells. The confirmation was based on the analysis of lineage specific cell surface markers, intracellular expression of lineage specific markers, the presence of RNA transcripts of lineage specific markers, and/or the secretion of lineage specific proteins. The examples below illustrate the most typical phenotypic characteristics of transdifferentiation systems. However, these examples are in no way limited to a particular marker chosen.

3.1. HTS Derived from One Immortal Myelomonocytic Progenitor, One Immortal B Lymphocyte and One Immortal T Lymphocyte—HTS-KMW As an example, this type of HTS was created by hybridising one immortal myelomonocytic progenitor K562 cell, one immortal T lymphoid MOLT4 cell and one immortal B lymphoid WIL2NS cell. The HTS so obtained was labelled as a HTS-KMW system (followed by its serial number). The following steps for the process of establishing HTS-KMW, the solutions (hybridisation, culture and recovery media) and the parameters used in this invention are described below.

3.1.1. Cell Preparation for HTS-KMW

K562, WIL2NS, and MOLT4 cell lines were cultured in our standard TC medium (see Section 1.1) and incubated in a humidified incubator at 37° C., 5% $CO_2$. As a routine, each cell line was passaged every 3 days. Prior to cell hybridisation, the stable clone of each cell type which had the highest proliferation rate was established using the procedure described in Section 1.1.2. In some experiments, $CD71^+$-enriched cell populations established as described in Section 1.1.3 were used. Also, on some occasions, the $CD15^+$ cells of $CD71^+$-enriched K562 population (Section 1.1.3) were used in experiments.

3.1.2. Cell Hybridisation Protocol for Establishing HTS-KMW

A few wells of a TC 96-well plate were used as cell hybridisation wells. Each well was filled with approximately 150 μl of hybridisation medium, which consisted of 240 mM sorbitol (Sigma), 2.0 mM $KH_2PO_4$ (Sigma), 0.4 mM $CaCl_2$ (Sigma), 0.2 mM $Mg(C_2H_3O_2)_2$ (Sigma) and 0.2 mM $Ca(C_2H_3O_2)_2$ (Sigma), supplemented with 0.2% bovine serum albumin, BSA (Sigma). Prior to electrical cell hybridisation, the cells of the pre-selected clone of each cell type were washed once in a hybridisation medium for a few minutes and transferred to a well containing the fresh hybridisation medium. The well was designated as a pre-hybridisation well. Before the cell hybridisation process, a single and washed cell of each selected clone was manipulated according to Section 1.1.1 such that only three cells, one from each selected clone, were positioned in between a pair of identical, parallel electrodes, which was submerged to the bottom of the well (as shown in FIG. 33). The separation of the electrodes was set at 400 micrometers (e.g. 400 μm).

To achieve electrical cell hybridisation, firstly, an alternating current (AC) field with a frequency of 0.8 MHz and a field strength of circa 50-60 kilovolts per meter (e.g. 50-60 kV/m) was applied between the electrodes for a few seconds until the three cells were induced to attract to one another by dielectrophoresis, DEP, and form a string of cells. This process caused the cells to make good cell membrane contact. The cells were arranged in such a way that K562 cell was in the middle of the cell alignment (14) (see FIG. 32 or 33). Then, two electric square pulses, with an interval of 3 seconds between the pulses, were applied simultaneously with the AC field. Each pulse with an intensity of circa 170 kV/m and a pulse width of 75 micro-seconds (e.g. 75 μsec) was used. After the completion of the second square pulse, the AC field was kept on continuously for another 5 seconds, resulting in cell hybridisation into a single tri-hybridised cell. For certain embodiments of this invention, it was observed that hybridisation of the three cells might not take place simultaneously, i.e. hybridisation of two out of the three cells frequently occurred first followed by the hybridisation of the third cell. In some cases an additional square pulse was required to obtain a complete three-cell hybridisation. The newly created tri-hybridised trans-differentiating cell was then transferred from the hybridisation well to a recovery well, which was located in a different row from that of the hybridisation wells. Each recovery well contained 150 μl standard TC medium (see Section 1.1). Each newly established trans-differentiating cell was incubated, one trans-differentiating cell per recovery well, in a humidified incubator, operated at 37° C. and 5% $CO_2$ content, for seven days. Most of the trans-differentiating tri-hybrid cells were found to divide within 36 hours after the cell hybridisation event. At the end of the incubation period, the medium in each recovery well was appropriately replenished with fresh standard medium. This stimulated cell proliferation of each trans-differentiating tri-hybrid clone. Two or three days later dividing or surviving cells were identified from each recovery well and were plated into the wells of a standard 24-well TC plate, giving rise to a set of trans-differentiating tri-hybrid clones. Each trans-differentiating tri-hybrid clone was cultured in the 24-well plate for another week before being transferred into a 25 $cm^2$ TC flask, containing 10 milliliters (ml) of our standard culture medium (see Section 1.1) and being labelled appropriately for further analysis. The entire process of electrical cell hybridisation and trans-differentiating tri-hybrid recovery process was repeated for a number of times in order to create a batch of stable trans-differentiating tri-hybrid cells.

3.1.3. Lineage Marker Profile of HTS-KMW

An example of the verification of co-expression of lineage specific markers on established HTS-KMW cell line is given below.

After a HTS-KMW cell line had been established under normal culture conditions for 6 months, the HTS-KMW cell population was analysed for the expression of specific CD markers of myeloid, B and T lymphoid lineages.

A tri-colour FACS analysis was utilised to verify co-expressions of the following CD markers: CD19 originating from WIL2NS, CD15 originating from K562, and CD4 originating from MOLT4.

In brief, 100 μl of HTS-KMW cells at concentration of $1 \times 10^6$ cells/ml in PBS containing 5% BSA were suspended in 100 μl of PBS and incubated for 30 min at 4° C. with 0.5 mg/100 ml of mouse anti-human CD15-PerCP, 0.25 mg/100 ml of mouse anti-human CD4-PE and 1.0 mg/100 ml of mouse anti-human CD19-FITC antibodies or an appropriate isotype control. All mouse anti-human antibodies were acquired from BD Pharmingen. After extensive washing with PBS, the labelled cells were analysed using FACSCalibur flow cytometer and CellQuest Pro software.

Figure 9:
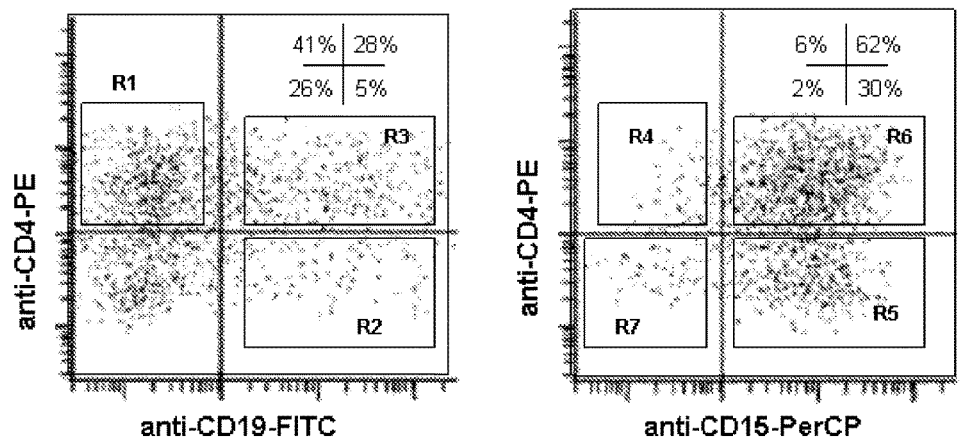
FIG. 9. FACS Profiles of CD expressions on HTS-KMW cells and sorting regions for different phenotypic cell populations.

FIG. 9 shows typical FACS profile of the HTS-KMW cells, which indicates that the HTS-KMW cells, where lineage specific characteristics come from immortal phenotypes, contain heterogeneous cell populations of mixed phenotypes, with myeloid being predominant. However, 62% of HTS-KMW cells shared myeloid and T lymphoid phenotypes and 28% of HTS-KMW cells express T and B lymphoid phenotypes.

3.1.4. Isolation of Different Phenotypic Populations from HTS-KMW

The HTS-KMW cells were further sorted into six different phenotypic populations, specifically: (1) $CD15^+CD19^+CD4^+$; (2) $CD15^+CD19^+CD4^-$; (3) $CD15^+CD19^-CD4^+$; (4) $CD15^-CD19^+CD4^+$; (5) $CD15^-CD19^+CD4^-$; (6) $CD15^-CD19^-CD4^+$.

The sorting regions were set as shown in FIG. 9. The sorting gates for different cell populations were defined as follows: (1) $CD15^+CD19^+CD4^+$ cell population designated as HTS-KMW.1 and counted in both R3 and R6 regions; (2)

CD15$^+$CD19$^+$CD4$^-$ cell population designated as HTS-KMW.2 and counted in both R5 and R2 regions; (3) CD15$^+$CD19$^-$CD4$^+$ cell population designated as HTS-KMW.3 and counted in both R6 and R1 regions; (4) CD15$^-$CD19$^+$CD4$^+$ cell population designated as HTS-KMW.4 and counted in both R4 and R3 regions; (5) CD15$^-$CD19$^+$CD4$^-$ cell population designated as HTS-KMW.5 and counted in both R7 and R2 regions; (6) CD15$^-$CD19$^-$CD4$^+$ cell population designated as HTS-KMW.6 and counted in both R4 and R1 regions. Sorted cell populations were transferred into fresh culture medium and grown as separate cultures under normal culture conditions. The purity of each cell population was verified immediately after sorting with accepted purity of 98%.

3.2. HTS Derived from One Immortal Myelomonocytic Progenitor, One Primary B Lymphocyte and One Primary T Lymphocyte—HTS-KBT As an example, this type of FITS was created by somatic cell hybridisation of one immortal myeloid cell derived from K562 cell line, one primary human B cell and one primary human T cell. The type of HTS was dubbed HTS-KBT followed by serial number.

3.2.1. Cell Preparation for Establishing HTS-KBT

The preparation of K562 cells prior to the creation of HTS-KBT has been described previously (Section 1.1.3). The primary cells used in the creation of HTS-KBT included (i) mature B cells (CD19$^+$) derived from spleen, peripheral blood or umbilical cord blood; early B cells (CD20$^-$CD72$^+$) derived from bone marrow; activated B cells (CD20$^+$CD72$^+$) derived from bone marrow; antigen experienced B cells (CD19$^+$CD5$^+$) derived from umbilical cord blood and (ii) helper T cells (CD4$^+$) derived from spleen and peripheral blood, antigen-experienced T cells (CD3$^+$CD5$^+$) derived from umbilical cord blood; CD3$^+$ T cells from umbilical cord blood, as well as double positive T cells (CD4$^+$CD8$^+$) derived from thymus were used in experiments. The isolation of various primary lymphoid cells from various lymphoid tissues has been described previously in Section 1.3.

3.2.2. Cell Hybridisation Protocol for Establishing HTS-KBT

The cell hybridisation protocol for establishing HTS-KBT is similar to that used for establishment of HTS-KMW (Section 3.1.2), except that the medium and the AC electric fields and pulses varied. The hybridisation medium used in these experiments consisted of 230 mM sorbitol, 1.8 mM KH$_2$PO$_4$, 0.5 mM CaCl$_2$, 0.2 mM Mg(C$_2$H$_3$O$_2$)$_2$ and 0.3 mM Ca(C$_2$H$_3$O$_2$)$_2$, supplemented with 0.3% BSA. An AC field of 0.5 MHz and 65-75 kV/m was applied simultaneously with a train of three square pulses at a 3-second interval, each with a pulse width of 100 μsec and strength of 175-185 kV/m. The AC field was switched on continuously for another 5 sec after the completion of the third square pulse resulting in the hybridisation of the cells to produce a cross-lineage tri-hybrid cell. The incubation and HTS tri-hybrid recovery protocols of each newly formed transdifferentiating hybrid cell has been described previously (Section 3.1.2).

3.2.3. Lineage Marker Profile of HTS-KBT

Examples of the verification of co-expression of lineage specific markers on established HTS-KBT cells are given below.

Figure 10:
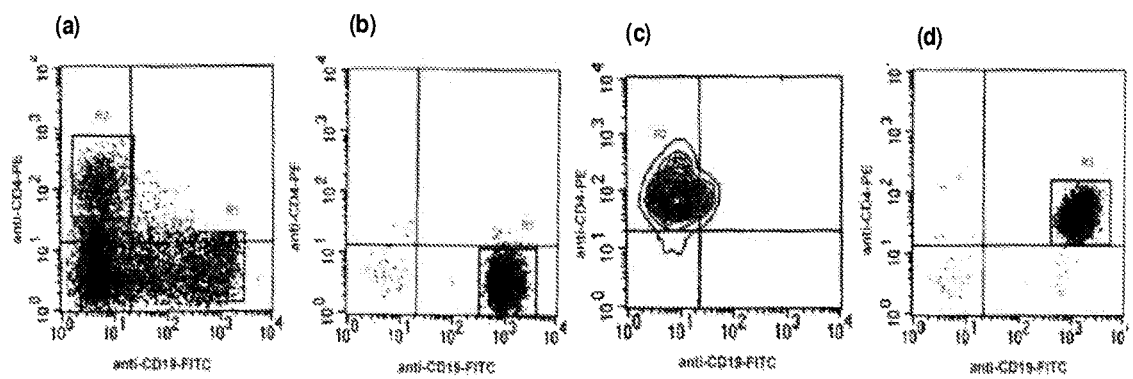
FIG. 10. Expressions of CD4 and CD19 on primary mixed spleen lymphocytes, populations of sorted CD4 and CD19 and a resulting HTS-KBT cell line; (a) expression of CD4 and CD19 on primary spleen lymphocytes (b) purity profile of sorted $CD19^+$ cells (98.1%); (c) purity profile of sorted $CD4^+$ cells (96.8%); (d) co-expression of CD19 and CD4 on HTS-KBT cells. More than 99% of HTS-KBT cell population co-express markers for both B and T cells.

3.2.3.1 Marker Profile of HTS-KBT Established from One Immortal Myeloid Cell, One Primary Mature B Cell and One Primary Effector T Helper Cell After a HTS-KBT cell line, for example, had been established under normal culture conditions for a few months, the cell line was analysed for the expression of lineage specific CD markers. The cells of HTS-KBT cell line were labelled with mouse anti-human CD19 and CD4 antibodies using the same protocols as described in cell preparation prior to hybridisation (Section 1.3.3). FIG. 10($d$) shows FACS profiles (CD19 and CD4 labels) of a HTS-KBT cell line established from one immortal myelomonocytic cell and 2 primary cells. Typically, more than 99% of cells in such a stable cross-lineage tri-hybrid expressed CD markers for both B and T cells with the density similar to that of parent, primary cells.

3.2.3.2 Marker Profile of HTS-KBT Established from One Immortal Myeloid Cell and Two Primary Antigen-Experienced Lymphoid Cells (B and T Cells)

In another embodiment a HTS-KBT cell line derived from cell hybridisation of one K562 cell, one antigen-experienced B and one antigen-experienced T cell was established. This variant of HTS-KBT was designated as HTS-KBT$^{AE}$. The cells were analysed for co-expression of CD19, CD3 and CD5 using a FACS.

Figure 11:
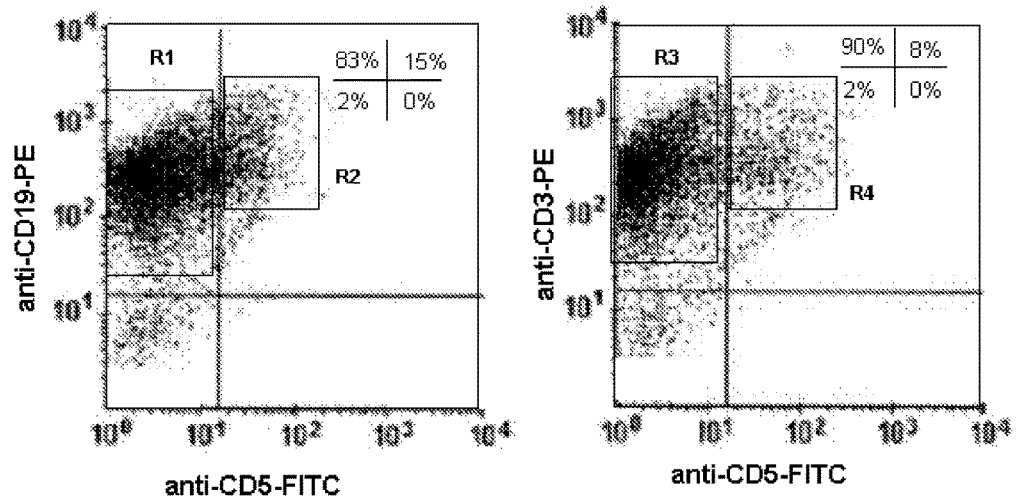
FIG. 11. Expressions of CD19, CD3 and CD5 on HTS-$KBT^{AE}$ line derived from one immortal myeloid and two primary antigen-experienced lymphoid cells: (a) expressions of CD19 and CD5 on HTS-KBT$^{AE}$ cell surface; (b) expressions of CD3 and CD5 on HTS-KBT$^{AE}$ cells.

In brief, the cells were labelled with mouse anti-human CD5-FITC and mouse anti-human CD19-PE or mouse anti-human CD4-PE antibodies using the same protocols as in cell preparation prior to cell hybridisation (Section 1.3.3). FIG. 11 shows FACS profiles of cells of such HTS-KBT$^{AE}$ cell line. The results show that 5-10% of the HTS-KBT$^{AE}$ cell population retained its memory of antigen exposure by maintaining cell surface expression of CD5 molecule whilst being positive for CD3 or/and CD19. Also at least 83% of CD5 negative cell population co-expressed both B lineage (CD19) and T lineage (CD3) markers.

3.2.3.3 Isolation of Different Phenotypic Populations from HTS-KBT$^{AE}$

The HTS-KBT$^{AE}$ cells were further sorted into six different phenotypic populations, specifically: (1) CD3$^+$CD19$^+$CD5$^+$; (2) CD3$^+$CD19$^+$CD5$^-$; (3) CD3$^+$CD19$^-$CD5$^+$; (4) CD3$^+$CD19$^-$CD5$^-$; (5) CD3$^-$CD19$^+$CD5$^+$; (6) CD3'CD19+CD5$^-$.

The sorting regions were set as shown in FIG. 11. The sorting gates for different cell populations were defined as follows: (1) CD3$^+$CD19$^+$CD5$^+$ cell population designated HTS-KBT$^{AE}$.1 and counted in both R2 and R4 regions; (2) CD3$^+$CD19$^+$CD5" cell population designated as HTS-KBT$^{AE}$.2 and counted in both R1 and R3 regions; (3) CD3$^+$CD19$^-$CD5$^+$ cell population designated as HTS-KBT$^{AE}$.3 and counted in R4 region but not R2 region; (4) CD3$^+$CD19$^-$CD5$^-$ cell population designated HTS-KBT$^{AE}$.4 and counted in R3 region but not R1 region; (5) CD3$^-$CD19$^+$CD5$^+$ cell population designated as HTS-KBT$^{AE}$.5 and counted in R2 but not R4 region; (6) CD3$^-$CD19$^+$CD5$^-$ cell population designated as HTS-KBT$^{AE}$.6 and counted in R1 but not R3 region. Sorted cell populations were transferred into fresh culture medium and grown as separate cultures under normal culture conditions. The purity of each cell population was verified immediately after sorting with accepted purity of 98%.

3.2.3.4 Marker Profile of Hts-Kbt Established from One Immortal Myeloid Cell, an Activated B Cell and One Primary Double Positive Uncommitted Effector T Cell In another embodiment a HTS-KBT cell line derived from cell hybridisation of one K562, one T cell (double positive for CD4$^+$ and CD8$^+$) isolated from thymus and one activated B cell (CD20$^+$ and CD72$^+$) isolated from bone marrow was established. This variant of HTS-KBT was designated as HTS-KBT$^{DP}$. The cells were analysed for co-expressions of CD4, CD8, CD20 and CD72 on the cell surface.

Figure 12:
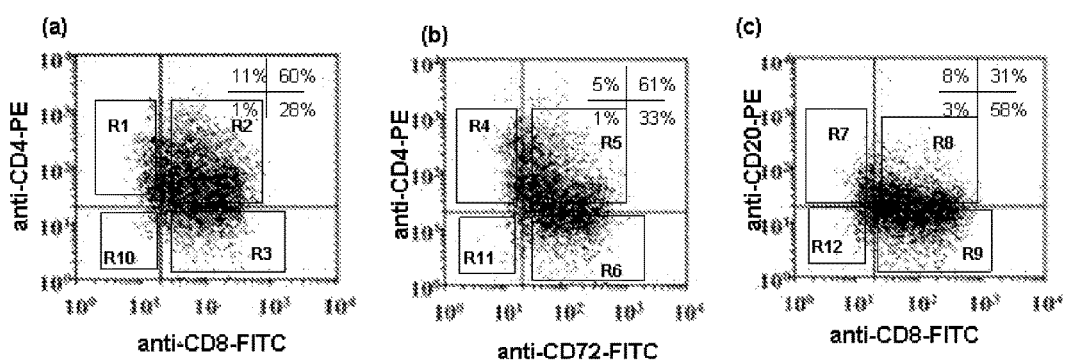
FIG. 12. Surface expressions of CD4, CD8, CD72 and CD20 on HTS-KBT$^{DP}$ cells derived from one immortal myeloid and two primary lymphoid cells derived from bone marrow and thymus: (a) expressions of CD4 and CD8 on the surface of HTS-KBT$^{DP}$, (b) expressions of CD4 and CD72 on the surface of HTS-KBT$^{DP}$, (c) expressions of CD20 and CD8 on the surface of HTS-KBT$^{DP}$.

In brief, the HTS-KBT$^{DP}$ cells were either labelled with antibody combination of mouse anti-human CD4-PE and mouse anti-human CD72-FITC antibodies or mouse anti-human CD20-PE and mouse anti-human CD8-FITC antibodies or mouse anti-human CD4-PE and mouse anti-human CD8-FITC antibodies using the same protocol as described for isolation of primary lymphocytes (Section 1.3). FIG. 12 shows FACS profiles of such HTS-KBT$^{DP}$ cells.

The results (see FIG. 12) showed that 99% of HTS-KBT$^{DP}$ cells expressed either of double positive T cell derived CD4 or CD8 on its surface where 66-71% of cells were being positive for CD4 and 88-89% of cells were being positive for CD8. In 60% of these cells, the expression of CD4 and CD8 was concurrent. Whilst being positive for CD4 derived from double positive thymocytes, 61% of cells were also positive for CD72 derived from activated B cells of bone marrow. However, 94% of HTS-KBT$^{DB}$ population expressed CD72 on their surface. On the other hand, 31% of CD8 positive cells co-expressed CD20. The total number of CD20 positive cells was 39%.

3.2.3.5 Isolation of Different Phenotypic Populations from HTS-KBT$^{DP}$

The HTS-KBT$^{DP}$ cells were further sorted into fifteen different phenotypic populations, specifically: (1) CD4$^+$CD8$^+$CD20$^+$CD72$^+$; (2) CD4$^+$CD8$^+$CD20$^+$CD72$^-$; (3) CD4$^+$CD8$^+$CD20$^-$CD72$^+$; (4) CD4$^+$CD8$^+$CD20$^-$CD72$^-$; (5) CD4$^+$CD8$^-$CD20$^+$CD72$^+$; (6) CD4$^+$CD8$^-$CD20$^+$CD72$^-$; (7) CD4$^+$CD8$^-$CD20$^-$CD72$^+$; (8) CD4$^+$CD8$^-$CD20$^-$CD72$^-$; (9) CD4$^-$CD8$^+$CD20$^+$CD72$^+$; (10) CD4$^-$CD8$^+$CD20$^+$CD72$^-$; (11) CD4$^-$CD8$^+$CD20$^-$CD72$^+$; (12) CD4$^-$CD8$^+$CD20$^-$CD72$^-$; (13) CD4$^-$CD8$^-$CD20$^+$CD72$^+$; (14) CD4$^-$CD8$^-$CD20$^+$CD72$^-$; (15) CD4$^-$CD8$^-$CD20$^-$CD72$^+$.

The sorting regions were set as shown in FIG. 12. The sorting gates for different cell populations were defined as follows: (1) CD4$^+$CD8$^+$CD20$^+$CD72$^+$ cell population designated HTS-KBT$^{DP}$.1 and counted in all three regions of R2, R5 and R8; (2) CD4$^+$CD8$^+$CD20$^+$CD72$^-$ cell population designated as HTS-KBT$^{DP}$.2 and counted in all three regions of R2, R8 and R4; (3) CD4$^+$CD8$^+$CD20$^-$CD72$^+$ cell population designated as HTS-KBT$^{DP}$.3 and counted in all three regions of R2, R5 and R9; (4) CD4$^+$CD8$^+$CD20$^-$CD72$^-$ cell population designated HTS-KBT$^{DP}$.4 and counted in all three regions of R2, R4 and R9; (5) CD4$^+$CD8$^-$CD20$^+$CD72$^+$ cell population designated as HTS-KBT$^{DP}$.5 and counted in all three regions of R1, R5 and R7; (6) CD4$^+$CD8$^-$CD20$^+$CD72$^-$ cell population designated as HTS-KBT$^{DP}$.6 and counted in all three regions of R1, R4 and R7; (7) CD4$^+$CD8$^-$CD20$^-$CD72$^+$ cell population designated as HTS-KBT$^{DP}$.7 and counted in all three regions of R1, R5 and R12; (8) CD4$^+$CD8$^-$CD20$^-$CD72$^-$ cell population designated as HTS-KBT$^{DP}$.8 and counted in all three regions of R1, R4 and R12; (9) CD4$^-$CD8$^+$CD20$^+$CD72$^+$ cell population designated as HTS-KBT$^{DP}$.9 and counted in all three regions of R3, R6 and R8; (10) CD4$^-$CD8$^+$CD20$^+$CD72$^-$ cell population designated as HTS-KBT$^{DP}$.10 and counted in all three regions of R3, R11 and R8; (11) CD4$^-$CD8$^+$CD20$^-$CD72$^+$ cell population designated as HTS-KBT$^{DP}$.11 and counted in all three regions of R3, R6 and R9; (12) CD4$^-$CD8$^+$CD20$^-$CD72$^-$ cell population designated as HTS-KBT$^{DP}$.12 and counted in all three regions of R3, R11 and R9; (13) CD4$^-$CD8$^-$CD20$^+$CD72$^+$ cell population designated as HTS-KBT$^{DP}$.13 and counted in all three regions of R10, R6 and R7; (14) CD4$^-$CD8$^-$CD20$^+$CD72$^-$ cell population designated as HTS-KBT$^{DP}$.14 and counted in all three regions of R10, R11 and R7; (15) CD4$^-$CD8$^-$CD20$^-$CD72$^+$ cell population designated as HTS-KBT$^{DP}$.15 and counted in all three regions of R10, R6 and R12. Sorted cell populations were transferred into fresh culture medium and grown as separate cultures under normal culture conditions. The purity of each cell population was verified immediately after sorting with accepted purity of 98%.

3.3 Example of HTS Derived from Primary Myelomonocytic Progenitor, Immortal B Lymphocyte and Primary T Lymphocyte—HTS-WTM As an example, this type of HTS was created by somatic cell hybridisation of one primary myeloid progenitor derived from bone marrow, one immortal human B cell derived from WIL2NS cell line and one primary human T cell. The type of HTS was dubbed HTS-WTM followed by serial number.

3.3.1. Cell Preparation for Establishing HTS-WTM

The preparation of WIL2NS cells used in the creation of HTS-WTM was described previously in Section 1.1.3. The primary cells of helper T cells (CD4$^+$) derived from spleen, peripheral blood, umbilical cord blood and thymus were used in these experiments. The isolation of various primary lymphoid cells from various lymphoid tissues has been described previously (Section 1.3). The primary myeloid progenitor cells were derived from CD34$^+$CD15$^+$ bone marrow mononuclear cells described in Section 1.2.2.

3.3.2. Cell Hybridisation Protocol for Establishing HTS-WTM

The cell hybridisation protocol for HTS-WTM production was similar to that used for HTS-KMW production (see Section 3.1.2), except that the medium varied. The hybridisation medium used in these experiments consisted of 235 mM sorbitol, 1.8 mM KH$_2$PO$_4$, 0.5 mM CaCl$_2$, 0.3 mM Mg(C$_2$H$_3$O$_2$)$_2$, and 0.25 mM Ca(C$_2$H$_3$O$_2$)$_2$ (Sigma), supplemented with 0.3% BSA. The exact electrical protocol as described in Section 3.2.2 was used for the production of WTM. The incubation and HTS tri-hybrid recovery protocols of each newly formed trans-differentiating hybrid cell has been described previously (Section 3.1.2).

3.3.3. Lineage Marker Profile of HTS-WTM

Examples of the verification of co-expression of lineage specific markers on established HTS-WTM cells are given below.

Figure 13:
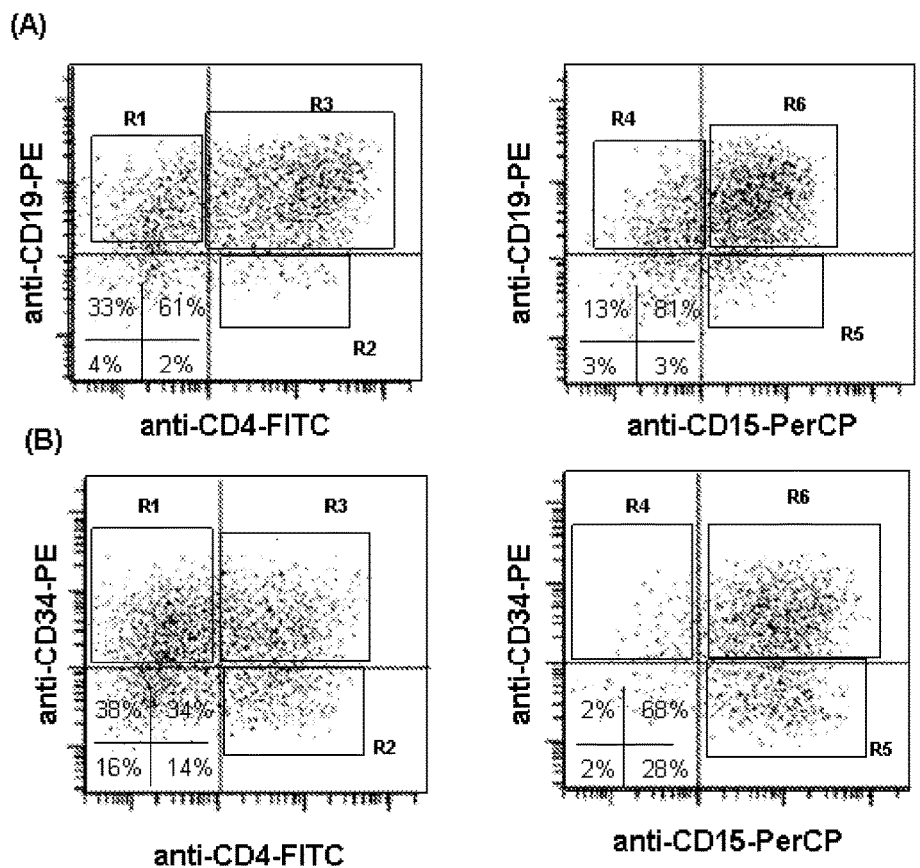
FIG. 13. CD expressions on the surface of HTS-WTM cells originating from myelomonocytic progenitor cells; (A) tri-colour staining with CD19, CD4 and CD15 and (B) tri-colour staining with CD34 and CD15 derived from myelomonocytic progenitor and CD4 derived from effector T cell.

3.3.3.1 Marker Profile of HTS-WTM Established from One Primary Myeloid Progenitor, One Immortal Lymphoid Cell and One Primary T Cell After HTS-WTM cell line derived from cell hybridisation of one immortal B lymphocyte derived from WIL2NS cell line, one primary T cell and one myelomonocytic progenitor had been cultured under normal conditions (see Section 1.1) for 6 months, the HTS-WTM cell population was analysed for the expression of lineage specific CD markers. The expression of surface markers for CD19 (B lineage), CD4 (T lineage), CD15 (myeloid lineage) and CD34 (progenitor cell) were analysed. In brief, the cells of this HTS-WMT cell line were labelled with combination of mouse anti-human CD19-PE, mouse anti-human CD4-FITC (BD Pharmingen) and mouse anti-human CD15-PerCP antibodies or with a combination of mouse anti-human CD34-PE, mouse anti-human CD4-FITC and mouse anti-human CD15-PerCP antibodies. The cell staining was performed according to the protocols described earlier (Section 1.3.3). Typical expression profiles of HTS-WTM cells originating from CD34$^+$CD15$^+$ myelomonocytic progenitor cell are shown in FIG. 13. The analysis showed that approximately 81% of HTS-WTM cells shared B lineage and myelomonocytic phenotypes (CD19$^+$CD15$^+$) and 61% of CD19$^+$ were also positive for CD4, T lineage marker. 34% of CD4$^+$ cells retained also CD34 on their surface and 68% of CD34$^+$ cells expressed CD15. Interestingly, 28% of CD34$^+$ cells do not retain expression of CD15 even though both CD34 and CD15 come from the same source (myelomonocytic progenitor cell).

3.3.3.2 Isolation of Different Phenotypic Populations from HTS-WTM

The HTS-WTM cells were further sorted into six different phenotypic populations, specifically: (1) $CD15^+CD19^+CD4^+$; (2) $CD15^+CD19^+CD4^-$; (3) $CD15^+CD19^-CD4^+$; (4) $CD15^-CD19^+CD4^+$; (5) $CD15^-CD19^+CD4^-$; and (6) $CD15^-CD19^-CD4^+$ based on the expressions of CD15, CD19 and CD4; or (7) $CD15^+CD34^+CD4^+$; (8) $CD15^+34^+CD4^-$; (9) $CD15^+34^-CD4^+$; (10) $CD15^-CD34^+CD4^+$; (11) $CD15^-CD34^+CD4^-$; and (12) $CD15^-CD34^-CD4^+$ based on the expression of CD15, CD34 and CD4.

The sorting regions were set as shown in FIGS. 13(A) and 13(B). The sorting gates for different cell populations based on CD15, CD19 and CD4 expression were defined as follows: (1) $CD15^+CD19^+CD4^+$ cell population designated as HTS-WTM.1 and counted in both R3 and R6 regions; (2) $CD15^+CD19^+CD4^-$ cell population designated as HTS-WTM.2 and counted in both R6 and R1 regions; (3) $CD15^+CD19^-CD4^+$ cell population designated as HTS-WTM.3 and counted in both R5 and R2 regions; (4) $CD15^+CD19^-CD4^-$ cell population designated as HTS-WTM.4 and counted in R5 region and NOT in regions R1, R2, and R3; (5) $CD15^-CD19^+CD4^+$ cell population designated as HTS-WTM.5 and counted in both R3 and R4 regions and NOT in regions R5 and R6; (6) $CD15^-CD19^-CD4^+$ cell population designated as HTS-WTM.6 and counted in R2 region and NOT in regions R4, R5, and R6. Sorted cell populations were transferred into fresh culture medium and grown as separate cultures under normal culture conditions. The purity of each cell population was verified immediately after sorting with accepted purity of 98%.

FIG. 13B shows sorting gates for different cell populations based on the expressions of CD15, CD34 and CD4. The gates were defined as follow: (7) $CD15^+CD34^+CD4^+$ cell population designated as HTS-WTM.7 and counted in both regions R3 and R6; (8) $CD15^+34^+CD4^-$ cell population designated as HTS-WRM.8 and counted in both regions R1 and R6; (9) $CD15^+34^-CD4^+$ cell population designated as HTS-WTM.9 and counted in both regions R2 and R5; (10) $CD15^-CD34^+CD4^+$ cell population designated as HTS-WTM.10 and counted in both regions R3 and R4; (n) $CD15^-CD34^+CD4^-$ cell population designated as HTS-WTM.11 and counted in both regions R1 and R4; and (12) $CD15^-CD34^-CD4^+$ cell population designated as HTS-WTM.12 and counted in region R2 and NOT in regions R2 and NOT in regions R4, R5, and R6. Sorted cell populations were transferred into fresh culture medium and grown as separate cultures under normal culture conditions. The purity of each cell population was verified immediately after sorting with accepted purity of 98%.

EXAMPLE 4

4. Transdifferentiation of HTS Cells into Different Cell Phenotypes by Changing Environmental Condition This example shows some of the possible models of cell transdifferentiation into different phenotypes through exposing a given HTS to a cell lineage permissive or a cell lineage promoting environment. Each example is in no way restricted to conditions given here.

4.1. Transdifferentiation of HTS Cells into $CD4^+$ T Cells

The HTS cells derived from the following subpopulations HTS-KMW.1, HTS-KMW.6, HTS-KBT, HTS-KBT$^{AE}$.1, HTS-KBT$^{AE}$.4, HTS-WTM.1, HTS-WTM.6, HTS-WTM.7 and HTS-WTM.12 and produced as describe in Section 3.1.4, Section 3.2.3.1, Section 3.2.3.3 and Section 3.3.3.2 as wells as control cultures of K562, MOLT4 and WIL2NS cells were transferred into fresh culture medium and cell concentration was adjusted to 250,000 to 500,000 cells per ml. The cell culture was supplemented with 10 U/ml of human IL-2 (BD Biosciences), 10 ng/mL of human IL-1 beta (BD Biosciences), 10 ng/ml of human IL-23 (R&D Systems), 1 µg/ml of anti-IL-4, 1 µg/mL of anti-IFN-γ and anti-CD3/CD28 activation beads at a ratio of 1 bead per cell (Invitrogen) and seeded in U-bottom 96 well plates at 200 µl per well (Corning). An increasing concentration of TGF-beta at 0.1, 1 and 10 ng/ml was added to a series of four wells. The culture media was replaced with fresh medium containing all cytokines and antibodies at days 3 and 5. On day 8 the cells were stained with anti-CD4, anti-CD19 and anti-CD15 and analysed by flow cytometry as described in Section 1.3.3. Prior to the staining cells were activated for 5 hours with 50 ng/ml of PMA, 500 ng/ml of ionomycin and 1× of BD GoldgiStop.

Figure 14:
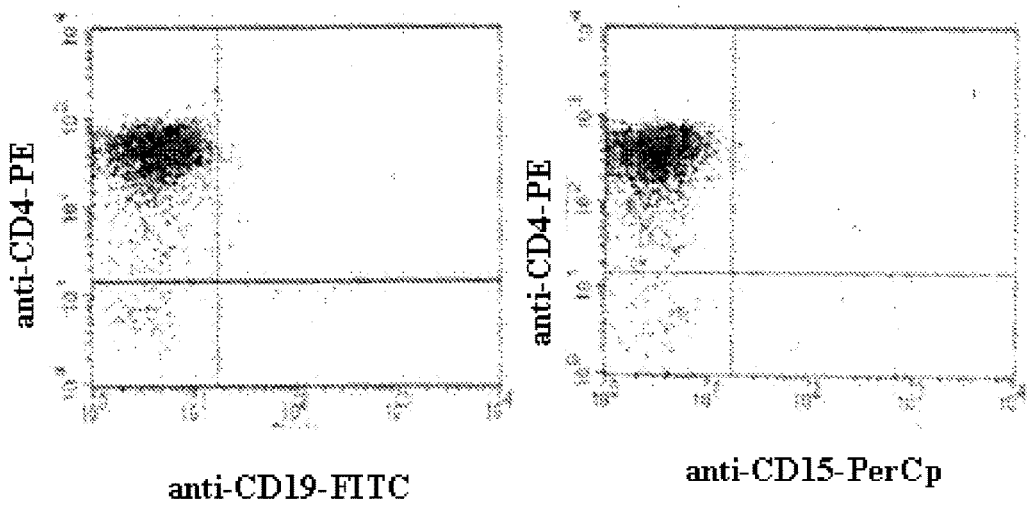
FIG. 14. A representative staining profile for CD4, CD19 and CD15 in cultures of HTS-KMW.6, HTS-WTM.6 and HTS-WTM.12 after 8 days in CD4 phenotype promoting environment where 100% of cells retained CD4 as the only marker on their cell surface (single positive CD4 cells). Not shown in the Figure, in HTS-KMW.1 culture, single CD4$^+$ cells represented 49% out of starting population consisting of 100% of triple positive CD15$^+$CD19$^+$CD4$^+$ cells; in HTS-KBT, it reached 50% out of initial 100% double positive CD19$^+$CD4$^+$ population; in HTS-KBT$^{AE}$.1, it reached 61% out of 100% triple positive CD3$^+$CD19$^+$CD5$^+$ population; in HTS- KBTAE.4, it reached 74% out of initial 100% of CD3$^+$ cells; in HTS-WTM.1, it reached 82% from 100% triple positive CD15$^+$CD19$^+$CD4$^+$ population; and in HTS-WTM.7, 71% of cells became single CD4 positive cells from 100% triple positive population of CD15$^+$CD34$^+$CD4$^+$ phenotype.

The cells were then labeled with mouse anti-human CD4-PE, anti-human CD19-FITC and anti-human CD15-PerCp antibodies as described in Section 3.1.3. FIG. 14 shows representative profile of tri-staining for CD4, CD19 and CD15 in cultures where 100% of cells expressed only CD4 on the surface after induced differentiation towards $CD4^+$ cells. In the HTS-KMW.1 culture, the single $CD4^+$ cells reached 49% out of total cell population initiated from pure population of triple positive ($CD15^+CD19^+CD4^+$) cells. In HTS-KBT it reached 50% derived out of initial 100% double positive ($CD19^+CD4^+$) population; 61% in HTS-KBT$^{AE}$.1 out of 100% triple positive ($CD3^+CD19^+CD5^+$) population; 74% in HTS-KBT$^{AE}$.4 out of initial 100% of $CD3^+$ cells; 82% in HTS-WTM.1 out of 100% triple positive ($CD15^+CD19^+CD4^+$) population; and 71% in HTS-WTM.7 became single CD4 positive cells from 100% triple positive population of $CD15^+CD34^+CD4^+$ phenotype. All control cultures of K562, MOLT4 and WIL2NS cells maintained their marker expression profile unchanged.

4.1.1 Characterisation of $CD4^+$ T Cells Generated from HTS

Single positive $CD4^+$ cells generated from HTS cultures induced towards $CD4^+$ T cells were sorted out for further analysis of markers expression and functional characterisation. Accepted purity was 98% of the total population of $CD4^+$ T cells.

4.1.1.1 Phenotypic profile of $CD4^+$ cells generated from HTS cultures Single positive CD4 cells derived from T lymphocyte permissive HTS cultures were further analysed for the expression of the following molecules on the cell surface either exclusively expressed on the surface of $CD4^+$ T cells or important for $CD8^+$ T cell functions: TCRαβ-T cell receptor; CD25IL-2 receptor alpha expressed activated T cells and in combination with CD4 denotes regulatory subset of $CD4^+$ T cells; CD27—involved in T cell co-stimulation; CD28—indicating activation of naïve T cells; CD62L—expressed on naïve and memory T cells and involved in horning; CD69—signal transduction molecule on activated T cells; CD95—upregulated upon activation; and CD45RO—indicating activated T cell or memory T cells. Each marker expression was assessed in combination with CD4. For this purpose, the cells were stained with mouse anti-human CD4-PE in combination with either mouse anti-human CD25-FITC, mouse anti-human CD27-FITC, mouse anti-human CD62L-FITC, mouse anti-human CD69-FITC, mouse anti-human CD95-FITC or mouse anti-human CD45RO-FITC following essentially the same protocol described in Section 1.3.3. Table 2 summarises the phenotypic profile of CD4+ T lymphocytes derived from different HTS cultures.

Whilst all of the cells from various cultures expressed the mature form of TCR on their surface, the CD expression profile shows a variety of the CD4$^+$ subsets generated in HTS cultures. Cells showed different abilities to homing as evidence by CD62L expression which markedly correlated to the level of expression for various activation molecules. It was possible to generate not only a subset of activated T helper cells but also a CD4$^+$CD25$^+$ regulatory subset of the T cells particularly in HTS-WTM cultures originating from primary myelomonocytic progenitor cells.

TABLE 2

Phenotypic profile of CD4+ cells generated from T cell permissive HTS cultures

| HTS culture | % single CD4+ | % of CD4+ Cells Expressing | | | | | | | |
|---|---|---|---|---|---|---|---|---|---|
| | | TCRαβ | CD25 | CD27 | CD28 | CD62L | CD69 | CD95 | CD45OR |
| KMW.1 | 49 | 100 | <1 | 5 | 6 | <1 | 7 | 21 | 7 |
| KMW.6 | 100 | 100 | <1 | 9 | 12 | <1 | 14 | 24 | 10 |
| KBT | 50 | 100 | 5 | 21 | 19 | 8 | 10 | 11 | 8 |
| KBT$^{AE}$.1 | 61 | 100 | 25 | 57 | 43 | 23 | 62 | 43 | 53 |
| KBT$^{AE}$.4 | 74 | 100 | 40 | 61 | 57 | 31 | 68 | 56 | 50 |
| WTM.1 | 82 | 100 | 10 | 19 | 23 | 12 | 21 | 24 | 13 |
| WTM.6 | 100 | 100 | 18 | 41 | 44 | 18 | 26 | 20 | 12 |
| WTM.7 | 71 | 100 | 48 | 12 | 25 | 47 | 15 | 6 | 6 |
| WTM.12 | 100 | 100 | 62 | 38 | 51 | 64 | 17 | 21 | 14 |

4.1.1.2 Production of Cytokines by CD4$^+$ Cells Generated from HTS Cultures

Single positive CD4$^+$ cells generated from T cell permissive HTS culture were further analysed for the production of IL-2, IL-4, IL-8, IL-10, IFN-γ and TNF-α following polyclonal activation with 10 ng/ml of lipopolysaccharide (LPS) for 4 days. The cells were seeded in 200,000 cells in 200 µl of complete medium per well of 96-flat-bottom well plates. The supernatants were removed and analysed by respective ELISA kit (all purchased from Invitrogen). Table 3 represents a typical profile of cytokine production in polyclonally stimulated CD4$^+$ derived from HTS cultures.

TABLE 3

Concentration of various cytokines in supernatants of CD4$^+$ cells generated from HTS cultures in a T lymphoid promoting environment

| HTS culture | Cytokine concentration in HTS cultures/ng/ml | | | | | |
|---|---|---|---|---|---|---|
| | IL-2 | IL-4 | IL-8 | IL10 | IFN-γ | TNF-α |
| KMW.1 | 14.5 | 68.9 | 12.3 | 19.4 | 0.72 | 12.8 |
| KMW.6 | 38.9 | 72.3 | 11.9 | 21.5 | 0.98 | 18.3 |
| KBT | 21.4 | 69.7 | 23.9 | 29.7 | 1.01 | 8.7 |
| KBT$^{AE}$.1 | 18.3 | 62.3 | 28.7 | 56.3 | 2.46 | 5.9 |
| KBT$^{AE}$.4 | 16.1 | 74.3 | 22.4 | 62.1 | 3.11 | 10.1 |
| WTM.1 | 42.7 | 45.1 | 44.1 | 39.8 | 1.98 | 1.05 |
| WTM.6 | 41.8 | 44.8 | 45.8 | 41.2 | 2.33 | 1.46 |
| WTM.7 | 45.4 | 49.8 | 40.1 | 35.2 | 3.25 | 4.3 |
| WTM.12 | 46.1 | 50.4 | 39.8 | 35.8 | 4.2 | 5.8 |

The cytokine profiles reconfirm the presence of different T cell subsets in CD4$^+$ cells generated from HTS cultures in T cell permissive environment ranging from inflammatory dominant to regulatory dominant profiles.

4.2. Transdifferentiation of HTS Cells into Cytotoxic CD8$^+$ T Cells

The cells derived from the following HTS populations HTS-KBT$^{AE}$.1 and HTS-KBT$^{AE}$.4 described in Section 3.2.3.3; HTS-KBT$^{DP}$.1, HTS-KBT$^{DP}$.4, and HTS-KBT$^{DP}$.12 described in Sections 3.2.3.5 as wells as control culture of K562 were used for differentiation of cytotoxic CD8$^+$ T lymphocytes.

For this purpose, control K562 cells and cells derived from each HTS populations were seeded at 100,000 cells per well in 24 well plates covered with monolayer of human thymic stromal cells. The thymic stromal cells were prepared from minced small fragment of thymus digested into a single cell suspension by incubation in PBS with 0.5 mg/ml of collagenase and 2 U/ml DNase I at 37° C. for 60 minutes with frequent agitation. The cell suspension was washed once with culture medium (RPMI1640, 10% FCS, 10 IU/ml penicillin, 10 pg/ml streptomycin, and 1 mmol/L L-glutamine). The thymic stromal cultures were established using either fresh or cryopreserved cells in 24-well plates at 10$^6$ cells per well in 2 ml of culture medium. After 2 days, the non-adherent cells were removed by washing 3 times with the culture medium. The monolayer was then maintained in the culture medium that was changed at least twice per week. The HTS cultures were also supplemented with 1% non-essential amino acids, 10 ng/ml of human IL-7 and 100 U/ml of human IL-2 (BD Bioscience). The culture medium was replaced with fresh medium containing cytokines at days 5 and 10.

Figure 15:
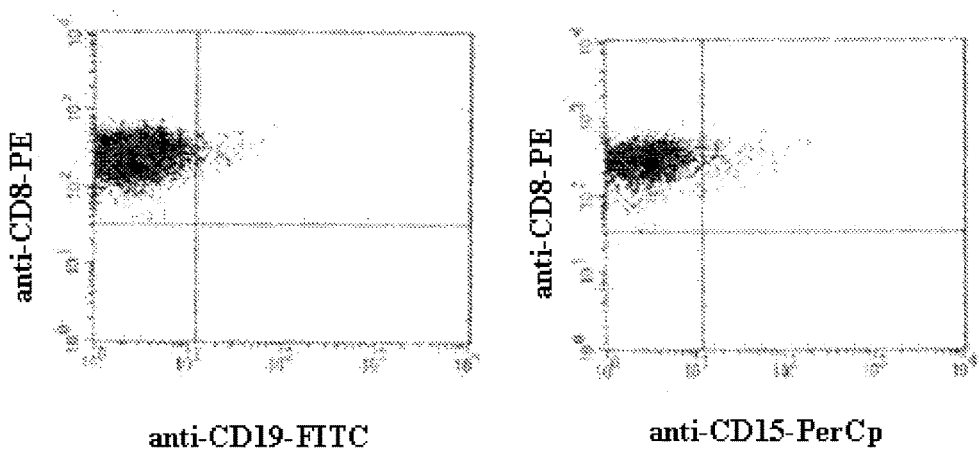
FIG. 15. A representative staining profile for CD8, CD19 and CD15 in HTS KBT$^{DP}$.12 culture where 100% of cells stained positive for just CD8 after 14 days of exposure to CD8$^+$ promoting environment. Not shown in the Figure, in KBT$^{AE}$.1, the number of single positive CD8 cells reached 53% from 100% triple positive CD3$^+$CD19$^+$CD5$^+$ population; in KBT$^{AE}$.4, it reached 61% derived from 100% single CD3$^+$ population; in HTS KBT$^{DP}$.1 and in HTS KBT$^{DP}$.4, these numbers were 72% and 86% out of 100% CD4$^+$CD8$^+$CD20$^+$CD72$^+$ and CD4$^+$CD8$^+$CD20$^-$CD71$^-$ populations, respectively.

On day 14, the HTS cells were analysed for the expression of CD8, CD19 and CD15. For this purpose, the cells were then labeled with mouse anti-human CD8-PE, anti-human CD19-FITC and anti-human CD15-PerCp antibodies as described in Section 1.3.3. FIG. 15 shows a typical profile of the lineage marker in HTS KBT$^{DP}$.12 culture where 100% of cells presented single positive (CD8$^+$) phenotype after induced differentiation towards CD8$^+$ cells. In KBT$^{AE}$.1, the number of single positive CD8 cells reached 53% from 100% triple positive CD3$^+$CD19$^+$CD5$^+$ population where in KBT$^{AE}$.4 such number was 61% derived from 100% single CD3$^+$ population. In HTS KBT$^{DP}$.1 and in HTS KBT$^{DP}$.4, the percentages of single CD8$^+$ cells climbed to 72% and 86% out of 100% CD4$^+$CD8$^+$CD20$^+$CD72$^+$ and CD4$^+$CD8$^+$CD20$^-$CD71$^-$ populations, respectively. No changes were been observed in control K562 cultures.

4.2.1 Characterisation of CD8$^+$ Cells Generated from HTS Cultures Single positive CD8$^+$ cells generated from HTS cultures induced towards cytotoxic T cells were sorted out for further analysis of markers expression and functional characterisation.

4.2.1.1 Phenotypic Profile of CD8$^+$ Cells Generated from HTS Cultures

Single positive CD8 cells derived from T lymphocyte permissive HTS cultures were further analysed for the expression of the following molecules on the cell surface either exclusively expressed on the surface of cytotoxic T cells or important for CD8+ T cell functions: TCRαβ-T cell receptor; CD8α and CD8β where down-regulation of β chain indicates prior antigen exposure; CD27—involved in T cell co-stimulation; CD28—indicating activation of naïve T cells; CD62L—expressed on naïve and memory T cells and involved in homing; CD95—up-regulated upon activation; and CD45RO—indicating activated T cell or memory T cells. At first, the cells were labeled with anti-human CD8α-PE (BD Pharmingen) and anti-human CD8β-FITC (BD Pharmingen) following essentially the same protocol described in Section 1.3.3. In subsequent stainings, anti-human CD8β-FITC was used in combination with anti-human TCRαβ-FITC, anti-human CD27-FITC, anti-human CD28-FITC, anti-human CD62L-FITC, anti-human CD95-FITC or anti-human CD45RO-FITC (all from BD Pharmingen). Table 4 summarises a phenotypic profile of CD8+ T lymphocytes derived from different HTS cultures.

TABLE 4

Phenotypic profile of CD8+ cells generated from T cell permissive HTS cultures

| HTS culture | % single CD8+ | % of CD8+ Cells Expressing | | | | | | | |
|---|---|---|---|---|---|---|---|---|---|
| | | TCRαβ | CD27 | CD28 | CD62L | CD95 | CD45OR | CD8α | CD8β |
| KBT$^{AE}$.1 | 53 | 100 | 51 | 41 | 22 | 45 | 52 | 100 | 100 |
| KBT$^{AE}$.4 | 61 | 100 | 64 | 52 | 28 | 53 | 49 | 100 | 100 |
| KBT$^{DP}$.1 | 74 | 100 | 71 | 30 | 8 | 29 | 11 | 100 | 100 |
| KBT$^{DP}$.4 | 86 | 100 | 68 | 28 | 10 | 32 | 16 | 100 | 100 |
| KBT$^{DP}$.12 | 100 | 100 | 75 | 32 | 8 | 36 | 12 | 100 | 100 |

The marker profiling revealed that all of the cells in various populations were homogeneous for expression of TCRαβ alone with both chains α and β for CD8. However, the cell populations showed not only a heterogeneous expression of other markers but also a different degree of marker expressions involved in activation, homing and memory.

4.2.1.2 Production of Cytokines by CD8+Cells Generated from HTS Cultures

Figure 16:
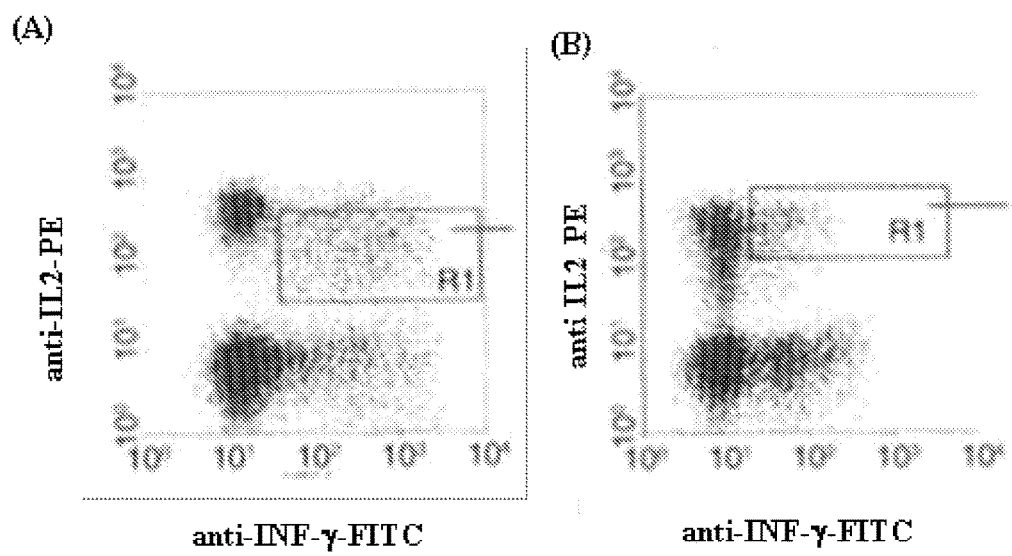
FIG. 16. Intracellular production of human IL-2 and human IFN-γ in single positive CD8 cells of HTS-KBT$^{AE}$.4 (A) and HTS-KBT$^{DP}$.12 (B) cultures. Whilst both cultures contained cells producing IL-2, IFN-γ or both, HTS-KBTDP.12 culture had a wide range of production levels for IL-2, in contrast the HTS-KBT$^{AE}$.4 culture exhibited a wider range of IFN-γ concentrations.

Single positive CD8 cells generated from HTS cultures were analysed for intracellular production of IFN-γ and IL-2. For this purpose, single positive CD8 cells derived from HTS cultures in T lymphoid condition were stimulated with phorbolester (PMA) at 50 ng/ml and ionamycin at 500 ng/ml under standard culture conditions. After 1 hour, 200 ng/ml of Brefeldin A was added and the cells were incubated under standard culture conditions for additional 3 hours. After washing, cells were fixed in 4% paraformaldehyde for 15 minutes at 20° C. After three washing cycles, the cells were permeabilised with saponin and stained with anti-IL-2-PE (Pharmingen), anti-IFN-γ-FITC or isotype control. FIG. 16 shows typical profiles of intracellular IL-2 and IFN-γ in single positive CD8 cells of HTS-KBT$^{AE}$.4 and HTS-KBT$^{DP}$.12 cultures. Whilst both cultures contained cells producing IL-2, IFN-γ or both, HTS-KBT$^{DP}$.12 culture had wide range of production levels for IL-2 in contrast to HTS-KBT$^{AE}$.4 culture having wider range of IFN-γ concentration.

4.2.1.3 Cytotoxic Effector Functions of CD8+ Cells Generated from HTS Cultures

Figure 17:
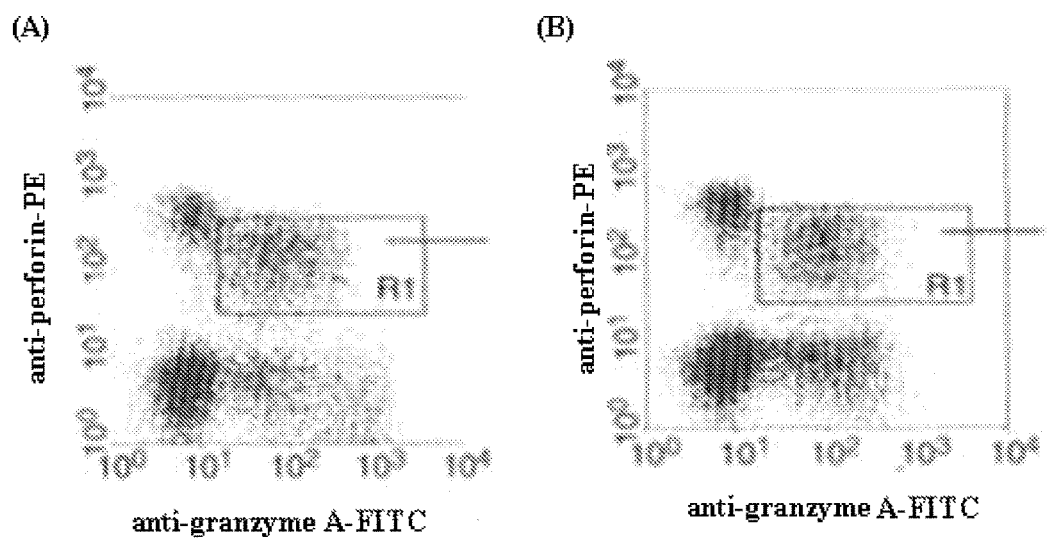
FIG. 17. Typical profiles of intracellular perforin and granzyme A in single CD8 positive cells of HTS-KBT$^{AE}$.4 (A) and HTS-KBT$^{DP}$.12 (B) cultures.

The production of intracellular cytotoxic granules is a major effector function indicating terminally differentiated T cells. For detection of intracellular cytotoxic granules, single positive CD8 cells from HTS cultures in T lymphocyte permitting conditions were fixed with 4% paraformaldehyde for 15 minutes at 20° C. After washing, the cells were permeabilised with saponin and stained with anti-perforin-PE (BD Pharmingen) and anti-granzyme A-FITC antibodies or isotype control. FIG. 17 shows typical profiles of intracellular perforin and granzyme A in single CD8 positive cells of HTS-KBT$^{AE}$.4 and HTS-KBT$^{DP}$.12 cultures. Both cultures contained cells either positive for perforin, granzyme A or both indicating functionally differentiated cytotoxic T cells. Approximately, 40% of the single CD8 positive cells in both cultures acquired such phenotype.

4.3. Transdifferentiation of HTS Cells into B Lymphocytes from HTS

Figure 18:
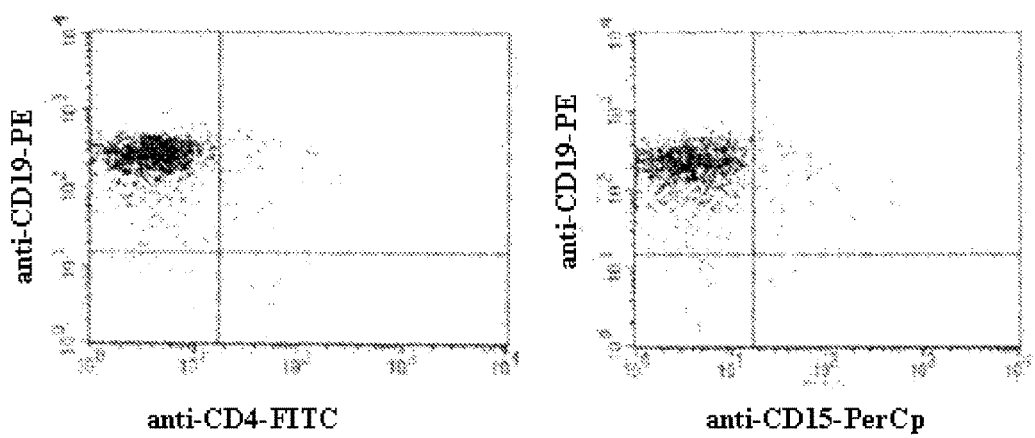
FIG. 18. Typical stainings of HTS-KBT$^{AE}$.6 culture with anti-CD19, anti-CD4 and anti-CD15 antibodies after 7 days in a B lymphoid promoting environment.

The cells derived from the following HTS populations HTS-KMW.1 and HTS-KMW.5 described in Section 3.1.4; HTS-KBT described in Section 3.2.3.1; HTS-KBT$^{AE}$.1 and HTS-KBT$^{AE}$.6 described in Section 3.2.3.3; HTS-KBT$^{DP}$.1 and HTS-KBT$^{DP}$.13 described in Section 3.2.3.5; HTS-WTM.1 and HTS-WTM.7 described in Section 3.3.4 as well as control cultures of K562, MOLT4 and WIL2NS were used for differentiation of B lymphocytes in presence of human bone marrow stromal cell line HS-5. The HS-5 cell line was routinely maintained in Dulbecco's modified Eagles' medium (DMEM) supplemented with 4 mM of L-glutamine, 1.5 g/L sodium bicarbonate and 10% (v/v) of FCS. One or two days before differentiation experiments, HS-5 cells were plated in 24-well plates at 60,000 cells per well in 1 ml of culture medium or in 96-flat-bottom well plates at 6,000 cells per well in 100 μl of culture medium. The B-lymphocyte differentiation co-cultures were initiated by removing HS-5 growth medium and seeding selected HTS cell populations in 24-well plates at 1,000 to 40,000 cells per well in 1 ml and in 96-well plates at 100 cells per well in 100 μl. The standard culture medium was supplemented with additives to promote B lymphoid lineage, specifically soluble CD40L at 4 ng/ml (Invitrogen), human IL-4 at 10 ng/ml (Invitrogen), human IL-5 at 5 ng/ml (Invitrogen), human IL-6 at 10 ng/ml (Invitrogen), human IL-10 at 10 ng/ml (Invitrogen), human IL-2 at 5 ng/ml (Invitrogen), human IL-7 at 20 ng/ml (Invitrogen), Flt3 ligand at 20 ng/ml (Invitrogen), stem cell-derived factor 20 ng/ml (BD Bioscience), human IL-3 at 10 ng/ml (Invitrogen) and agonist anti-CD40 mAb at 5 μg/ml (clone HM40-3, BD Bioscience). The culture medium was replaced on days 5 and 7 with fresh medium supplemented with additives to promote B lymphoid lineage. The non-adherent cells from HTS-KMW.1, HTS-KMW.5, HTS-KBT, HTS-WTM.1, HTS-WTM.7 and control cultures K562, MOLT4 and WIL2NS were collected and stained with mouse anti-CD4-FITC, mouse anti-CD19-PE and mouse anti-CD15-PerCP and analysed by flow cytometry as described in Section 1.3.3. FIG. 18 shows a typical staining profile of HTS-KBT$^{AE}$.6 culture with 100% single CD19+ cells after induced differentiation towards B lymphocytes. In the case of HTS-KBT$^{AE}$.1 and HTS-KBT$^{AE}$.6 cultures, the non-adherent cells were stained with anti-human CD3-FITC instead of anti-CD4-FITC. For HTS-KBT$^{DP}$.1 and HTS-KBT$^{DP}$.13 cultures, mouse anti-human CD20-PE was used instead of anti-CD 19-PE.

4.3.1 Characterisation of CD19$^+$ Cells Generated from HTS Cultures

Single positive CD19 cells derived from B lymphoid HTS cultures were sorted out and further analysed for B cell markers, presence of B-specific transcripts and functional characteristics such as immunoglobulin secretion and differentiation into plasma cells.

4.3.1.1 Surface Expression of Other B Cell Markers

CD19$^+$ cells derived from B lymphoid driven HTS cultures were further analysed for the expression of the following molecules on the cell surface either exclusively expressed on the surface of B cells or important for B cell functions: CD1c-MHC class I-like molecules associated with β2-microglobulin which have specialized role in antigen presentation; CD10 -zinc metalloproteinase involved in B cell development; CD20-B cell activation molecule; CD22—adhesion molecule expressed on mature B cells which is responsible for B cell interaction with monocytes and T cells; CD38—cell activation; CD40—B cell differentiation and co-stimulation involved in isotype switching and rescuing B cells from apoptosis; surface IgM and IgG.

For this purpose, CD19$^+$ cells derived from B lymphoid-driven HTS cultures were labelled with mouse anti-human CD1c-PE, mouse anti-human CD10-FITC, mouse anti-human CD20-PE, mouse anti-human CD22-FITC, mouse anti-human CD38-FITC, mouse anti-human CD40-FITC, mouse anti-human IgG-PE and mouse anti-human IgM-PE antibodies (BD Pharmingen). Essentially the same staining protocol was followed as described in Section 1.3.3 for all markers. Table 5 summarises a phenotypic profile of B lymphocytes derived from different HTS cultures.

No new marker expression, up-regulation or down-regulation was observed in control cultures of K562, WIL2NS and MOLT4.

When HTS-KBT$^{AE}$ populations derived originally from CD5$^+$ B cells were cultured in a B lymphoid promoting environment, more activated CD20$^+$, more mature CD22$^+$ and CD40$^+$ cells were detected. Given that these cultures also contained more IgG positive cells after the LPS stimulation (Table 6), the results indicate the ability of these particular populations to differentiate into functional B cells and plasma cells.

The appearance of CD10 on the cell surface, marker for pre-B cells coupled with disappearance of IgM expression on the cell surface, particularly in HTS-WTM cultures; strongly suggest de-differentiation of CD19$^+$ cells into more primitive pre-B cells.

4.3.1.2 Ability to Differentiate to Plasma Cells

On day 14, the cultures were exposed to 3.5 mg/ml of lipopolysaccharide (Sigma) to activate B lymphocytes and induce plasma cell formation. Secreted IgM and IgG were quantitated for all HTS-B lymphoid cultures by a standard ELISA using 96-ELISA-well plates and plastic-absorbed goat-affinity-purified antibodies to human μ and γ chains. The bound antibodies were revealed with HRP-conjugated sheep anti-human Ig antibodies. All antibodies used were from Sigma. ABTS was used as a substrate and optical densities were measured at 405 nm. Table 6 shows changes in phenotypic profile of the CD19$^+$ cells after exposure to LPS and Table 7 summarises levels of IgM and IgG detected in the B lymphocyte culture after day 7 and day 17.

TABLE 5

Phenotypic analysis of CD19$^+$ cell generated from HTS in B Lymphoid promoting environment

| HTS culture | % single CD19+ | % of CD19+ Cells Expressing |  |  |  |  |  |  |  |
|---|---|---|---|---|---|---|---|---|---|
| | | CD1c | CD10 | CD20 | CD22 | CD38 | CD40 | IgM | IgG |
| KMW.1 | 55 | 100 | <1 | 4 | 3 | 100 | <1 | 100 | <1 |
| KMW.5 | 100 | 100 | <1 | 7 | 6 | 100 | <1 | 100 | <1 |
| KBT | 96 | 100 | 5 | 9 | 9 | 100 | 4 | 100 | <1 |
| KBT$^{AE}$.1 | 99 | 100 | 3 | 7 | 16 | 100 | 6 | 100 | <1 |
| KBT$^{AE}$.6 | 100 | 100 | 2 | 4 | 13 | 100 | 7 | 100 | <1 |
| WTM.1 | 84 | 93 | 28 | 3 | 4 | 100 | <1 | 70 | <1 |
| WTM.7 | 68 | 91 | 31 | 5 | 9 | 100 | <1 | 68 | <1 |

TABLE 6

Phenotypic analysis of CD19+ B cells after stimulation with LPS

| HTS culture | % single CD19+ | % of CD19+ Cells Expressing | | | | | | | |
|---|---|---|---|---|---|---|---|---|---|
| | | CD1c | CD10 | CD20 | CD22 | CD38 | CD40 | IgM | IgG |
| KMW.1 | 58 | 100 | <1 | 4 | 3 | 100 | <1 | 100 | <1 |
| KMW.5 | 100 | 100 | <1 | 7 | 6 | 100 | <1 | 100 | <1 |
| KBT | 89 | 100 | 5 | 12 | 11 | 100 | 4 | 91 | 4 |
| KBT$^{AE}$.1 | 94 | 100 | 3 | 15 | 20 | 100 | 23 | 88 | 8 |
| KBT$^{AE}$.6 | 80 | 100 | 2 | 24 | 38 | 100 | 25 | 89 | 7 |
| WTM.1 | 82 | 92 | 15 | 6 | 8 | 100 | 2 | 82 | <1 |
| WTM.7 | 69 | 89 | 28 | 8 | 11 | 100 | 5 | 70 | 2 |

The reduction in numbers of single CD19$^+$ cells in HTS-KBT cultures could be attributed to further differentiation to plasma cells as the number of CD22$^+$ cells increased accompanied by an increase in CD40$^+$ positive cells as well as IgG bearing cells. The numbers of less mature CD10$^+$ pre-B cells in WTM cultures also decreased with rise in CD40$^+$ and CD22$^+$ positive cells.

The ELISA results confirm that there is a degree of progression from mature B cells to plasma cells in LPS stimulated cultures, particularly in HTS-KBT cultures where IgG was detected for the first time.

TABLE 7

Concentration of IgM and IgG in supernatants of HTS cultures in B lymphoid promoting environment

| HTS culture | Ig concentration in HTS cultures, ng/ml | | | |
|---|---|---|---|---|
| | day 7 | day 17 | day 7 | day 17 |
| KMW.1 | 28 | 159 | 0 | 0 |
| KMW.5 | 40 | 210 | 0 | 0 |
| KBT | 15 | 238 | 0 | 28 |
| KBT$^{AE}$.1 | 60 | 410 | 0 | 43 |
| KBT$^{AE}$.6 | 68 | 361 | 0 | 39 |
| WTM.1 | 20 | 164 | 0 | 0 |
| WTM.7 | 15 | 158 | 0 | 10 |

4.4. Transdifferentiation of HTS Cells into Macrophages

Figure 19:
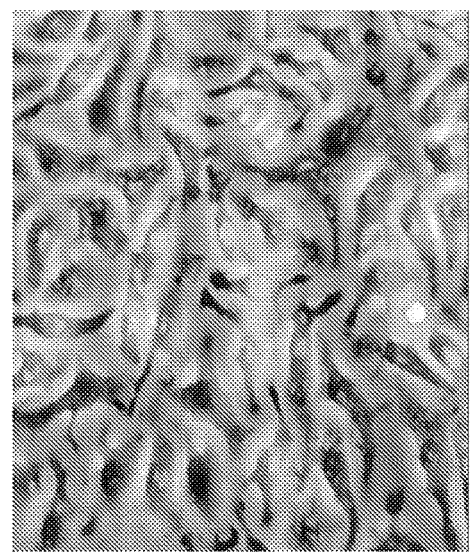
FIG. 19. Adherent morphology of cells generated from HTS culture after 8 days in a macrophage permissive growth medium.

The HTS cells derived from the following subpopulation HTS-WTM.4 and described in Section 3.3 as well as control culture of WIL2NS were transferred into fresh culture medium and the cell concentration was adjusted to 100,000 to 200,000 cells per ml. The cell culture was supplemented with 50 ng/ml of human IL-7 (Invitorgen), 50 ng/ml of human IL-6 (Invitrogen), 10 ng/ml of human IL3 (Invitrogen), 100 ng/ml of human M-CSF (BD Biosciences), 30 ng/ml of human GM-CSF (BD Biosciences) and 50 ng/ml of Flt3L (Invitrogen) and seeded in 24-well-flat-bottom plates at 1 ml per well. Fresh culture medium was replenished every 3 to 4 days to the culture by replacing half of the culture medium with a fresh one. FIG. 19 shows morphology of the HTS culture after 8 days where the cells assumed growth characteristics of adherent cells.

Figure 20:
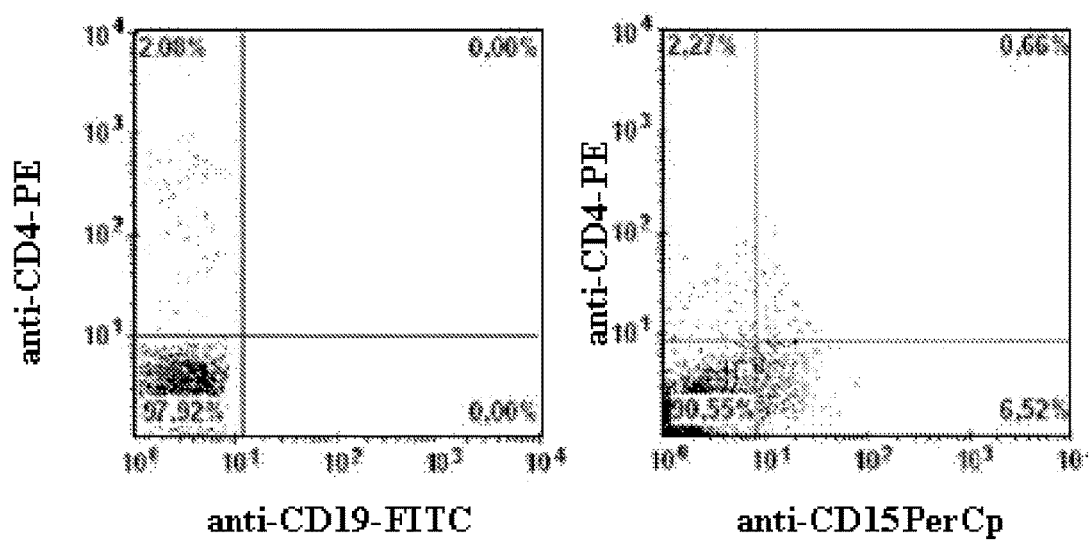
FIG. 20. Profile of CD19, CD15 and CD4 expression on HTS-WTM.4 cells after 8 days in macrophage permissive growth medium showing small percentage of cells still positive for CD4 and 7% of cells retaining myelomonocytic CD15 marker on the surface whilst losing expression of CD19 completely.

Cells then were labeled with mouse anti-human CD4, anti-human CD19 and anti-human CD15 antibodies as described in Section 1.3.3. FIG. 20 shows that majority of cells lost the expression of all markers after being in the macrophage permissive culture for 8 days with the exception of CD15 where approximately 7% of cells remained positive for the myelomonocytic lineage marker Only 2% of cells were positive for CD4 and none for CD19. Whereas no changes were observed in control WIL2NS culture.

4.4.1 Characterisation of Macrophages Generated from HTS

HTS-generated macrophages were subjected to analysis for expression of other macrophage lineage markers as well as functional performance.

4.4.1.1 Expression of Other Macrophage Markers

Figure 21:
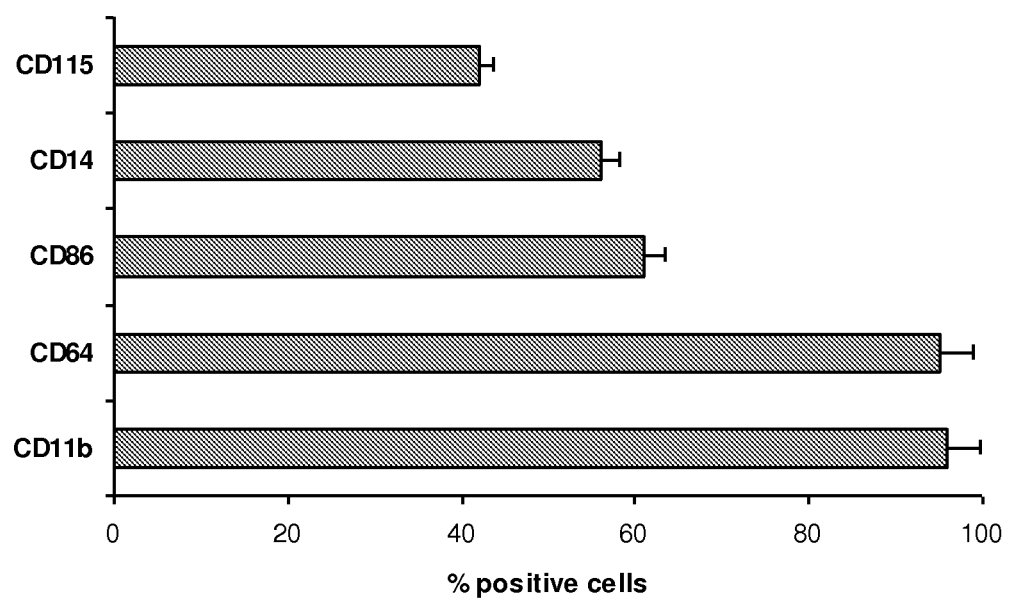
FIG. 21. Expressions of macrophage-like markers on the surface of HTS-WTM.4 cells after 8 hours in macrophage permissive growth media.

As there is no single marker exclusively characterising human macrophages, HTS generated adherent cells were also further analysed for expression of CD11b, CD86, CD64, CD14 and CD115, which are characteristics of macrophage lineage. For this purpose, adherent cells derived from macrophage-driven HTS cultures were labelled with anti-human CD11b-PE, CD86-FITC, CD64-FITC, CD14-PE and anti-CD115-PE antibodies (BD Pharmingen). Essentially the same staining protocol was followed as described in Section 1.3.3 for all markers, with exception to CD115-PE. The binding of M-CSF to its receptor CD115 may result in receptor internalisation and thus reduce the intensity of surface staining. Therefore, prior to staining with anti-CD115-PE, the cells were fixed and permeabilised with Cytofix/Cytoperm kit (BD Biosciences) so that the surface and intracellular CD115 could be assessed. Five separate cultures were analysed for the expression of macrophage like factors on the cell surface after 8 days in macrophage permissive medium. FIG. 21 summarises the distribution of macrophage-like CD markers (mean±SD) on HTS cells where approximately 96% of cells were positive for CD11b, 95% of cells for CD64, 61% for CD86, 56% for CD14 and 42% for CD115. Given that some of these markers may be expressed at various levels on granulocytes and dendritic cells (DCs), additional staining for human CD1a, CD83, CD15 and CD3 was performed using the protocol described in Section 1.3.3. Little (CD15) to no staining was observed. These results show that HTS cells when transferred into macrophage permissive medium acquire surface molecules crucial for macrophage functions such adhesion (CD11b), growth (CD 115 which is a receptor for M-CSF), phagocytosis (CD86) and immune phagocytosis (CD64 which is receptor for IgG).

4.4.1.2 Functional Characterisation of Macrophages Generated from HTS.

To assess functional characteristics, the macrophages generated in FITS were further analysed for phagocytic ability and production of nitric oxide (NO).

Figure 22:
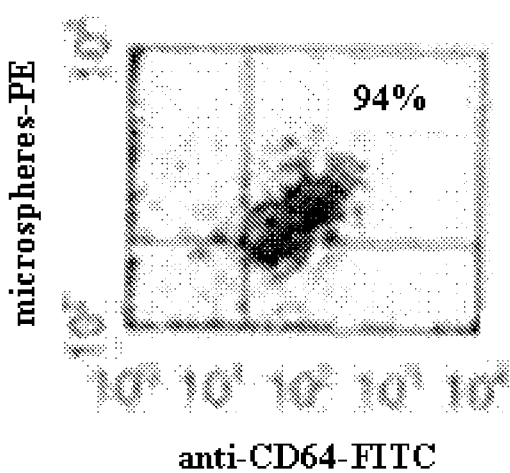
FIG. 22. Phagocytosis of 1000 nm microspheres by CD64 positive macrophages derived from HTS-WTM.4 culture after 8 days in macrophage permissive environment.

The phagocytic ability of was assessed by flow cytometry by the ability to phagocytose fluorescent microspheres (Molecular Probes). After 8 days in macrophage permissive medium the HTS cells were incubated at 1,000,000 cells per ml in 24-well plates for 18 hours with 5 µg/ml of LPS (Sigma) and carboxylated 40 nm and 1000 nm polystyrene microspheres with fluorescent phycoerythrin (PE) labels. The cells were collected and incubated on ice for 45 minutes with anti-human FITC-conjugated antibodies to CD64 in cold 2% (w/v) BSA/PBS, washed twice and analysed by flow cytometry. The double positive cells were assessed. FIG. 22 shows a typical profile of phagocytic activity in macrophage-driven HTS cells. Approximately, 94% of the cells exhibited phagocytic ability for small and large beads.

Figure 23:
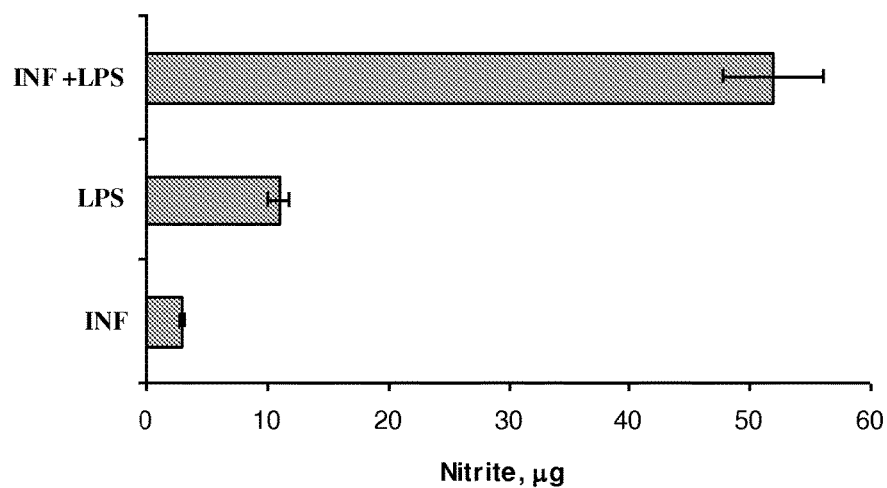
FIG. 23. Production of nitric oxide by LPS stimulated HTS-WTM.4 cells after 8 days in a macrophage permissive growth medium.

The production of NO was assessed by culturing macrophage driven HTS cells with 10 ng/ml of LPS, 100 U/ml of human interferon-γ (IFN-γ) or both in a 96-well flat bottom plate seeded at 200,000 cell per well in a total volume of 200 μl. After overnight stimulation, 50 μl of cell free supernatant were incubated with 50 μl of Griess reagent (1% sulfanilamide, 0.1% naphthylenediamine dihydrochloride, 2.5% $H_3PO_4$) at room temperature for 5 minutes, and the absorbance at 550 nm was selected in microplate reader. The concentration of NO was determined from a linear-regression analysis of a sodium nitrite standard curve. As shown in FIG. 23, the HST cells after being exposed to macrophage permissive medium produced nitric oxide in response to stimulation with LPS and IFN.

EXAMPLE 5

5. Transdifferentiation of HTS Cells into Different Cell Phenotypes by Hybridization With Cells of Mature Phenotype To further demonstrate the versatility of HTS and its insensitivity to the mechanism of transdifferentiation employed, the HTS cells were hybridized with mature effector T or B cell. The same strategy can also be employed for trans-differentiating cells of different phenotype.

Figure 24:
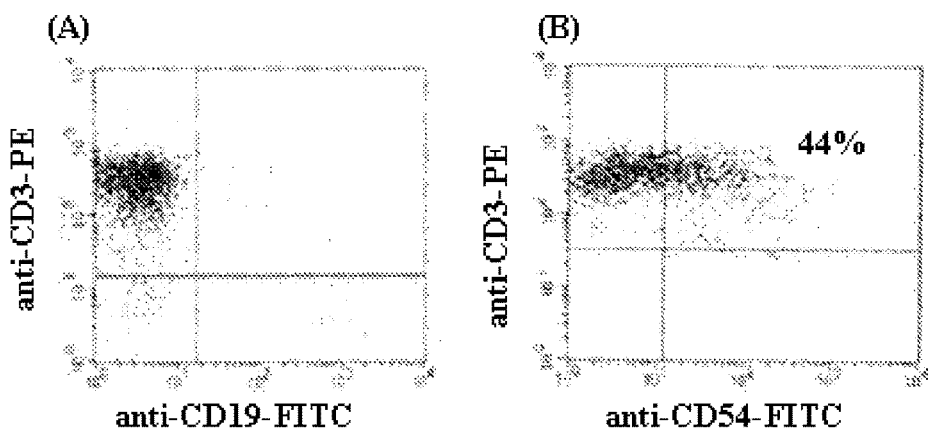
FIG. 24. Typical profiles of CD3 and CD54 expression by CD19$^+$ B lymphocytes derived from HTS-KBT$^{AE}$.6 trans-differentiated into T cells by somatic cell hybridisation with primary CD54+ human T cells.

5.1 Trans-Differentiation of HTS Cells into CD4 Positive T Cells by Hybridization with Primary $CD54^+$ T Cell The B cells derived from HTS subpopulations were used for trans-differentiating into $CD54^+$ T cells via electrical cell hybridisation. Specifically, cells derived from HTS-KMW.5 (single $CD19^+$ cells) described in Section 3.1.4, HTS-KB-$T^{AE}$.6 (single $CD19^+$ cells) described in Section 3.2.3.3 and HTS-KBT$^{DP}$.13 ($CD20^+CD72^+$ cells) described in Section 3.2.3.5 were used for transdifferentiation in this particular example. Primary human CD54 positive T cells isolated as described in Section 1.3.8 were used as a source of $CD54^+$ T cells. The hybridisation procedure was essentially the same as that used for the creation of corresponding HTS (see Section 3.1.2). After the resulting hybrids became stable, they were maintained as a cell line under standard culture conditions (see Section 1.1) and analysed for surface marker expression following protocol described in Section 1.3.3. All B cell subpopulations trans-differentiated this way lost their $CD19^+$ and became CD3+ cells as evidence by the representative example in FIG. 24A. They were further analysed for CD54 expression. In brief, $1 \times 10^5$ cells per 100 μl aliquots were labelled with mouse anti-human CD54-FITC and mouse anti-human C3-PE antibodies following the same protocol as described in Section 1.3.8 (isolation of $CD54^+$ T cells). The number of cells positive for CD54 ranged between 42 to 85% as presented in FIG. 24(B).

Figure 25:
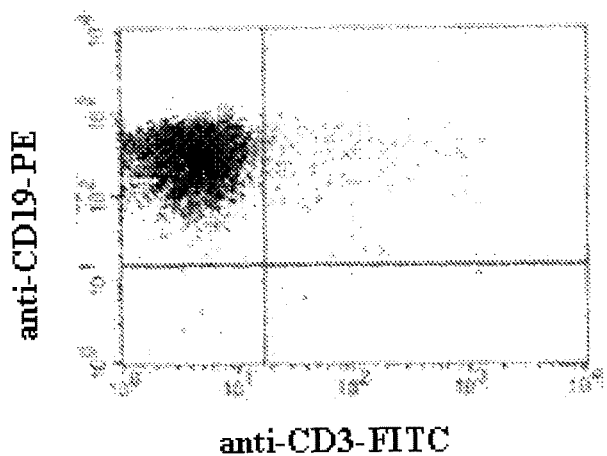
FIG. 25. A representative profile of transdifferentiation of CD3$^+$ HTS-KBT$^{AE}$.4 cells after somatic hybridisation with CD40 activated IgM positive B cells showing the loss of CD3 expression and acquisition of surface IgM.

5.2 Trans-Differentiation of HTS Cells into CD19 Positive B Cells by Hybridization with Primary Ig Secreting B Cells The T cells derived from the following HTS subpopulations were used for trans-differentiating into immunoglobulin (Ig) secreting cells. HTS-KMW.6 cells (single $CD4^+$ population) described in Section 3.1.4, HTS-KBT$^{AE}$.4 (single $CD3^+$ population) described in Section 3.2.3.3, HTS-KBT$^{DP}$.4 ($CD4^+CD8^+$ population) described in Section 3.2.3.5 were used for this purpose. Primary CD40 activated either IgM positive or IgG positive B cells isolated as described in Section 1.4 were used as a source of primary Ig secreting B cell. The electrical cell hybridisation procedure was essentially the same as that used for the creation of the corresponding HTS as described in Section 3.1.2. After the resulting hybrids became stable, they were maintained and analysed for expression of CD19, CD40 and surface Ig. All HTS subpopulations trans-differentiated in this manner lost their T cell marker expression (CD3, CD4, and CD8) and became CD19, CD40 and sIg positive cells. FIG. 25 shows a representative example of trans-differentiating $CD3^+$ HTS-KBT$^{AE}$.4 cells after hybridisation with CD40 activated IgM positive B cells showing loss of CD3 expression and acquisition of surface IgM.

The supernatants of B trans-differentiated T cell cultures were analysed for the presence of IgM or IgG by ELISA described earlier (see Section 1.4). The cells were seeded in round bottom 96-well plates at $1 \times 10^5$ cells per well and cultured under standard conditions for 24 hours. The results are summarised in Table 8. Each value is given as mean±SD of three independent measurements.

TABLE 8

Production of human IgM and IgG by HTS T cells after transdifferentiation to B cells

| HTS culture | IgM production when hybridized with IgM producing B cell (ng/ml) | IgG production when hybridized with IgG producing B cell (ng/ml) |
|---|---|---|
| HTS-KMW.4 | 31 ± 12.3 | 10 ± 1.9 |
| HTS-KBT$^{AE}$.4 | 18 ± 5.1 | 21 ± 3.7 |
| HTS-KBT$^{DP}$.4 | 38 ± 7.5 | 24 ± 4.3 |

EXAMPLE 6

6. De-Differentiation of Mature B Lymphocytes Derived from HTS Cells Via Exposure to Change Environmental Conditions $CD19^+$ cells derived from HTS-WTM.1 and HTS-WTM.7 and cultured in B lymphoid promoting environment as described in Section 4.3.1.1 showed an indication of de-differentiation to less mature B cell types when studied for expression of other B lymphoid markers, especially up-regulation of CD10 and down-regulation of surface IgM expression (see Section 4.3.1.1). In order to confirm the de-differentiation process initiated in these cultures, the cells were placed into a hematopoietic stem cell promoting environment described in Section 7.1 and after 5 days in such culture were also checked for the transcript presence of other early B cell markers such as Pax-5, λ-like and CD34.

In brief, total RNA was prepared from cultured cells using the RNeasy kit (RNeasy Mini kit, Qiagen). cDNA synthesis was performed with cDNA-Kit (Amersham Pharmacia) according to the manufacturer's protocol, and PCR was performed essentially as described by Sewing et al. The PCR reaction mixture was analysed by agarose gel (2%) electrophoresis and visualised by ethidium bromide staining. The oligonucleotide primer pairs had the sequences as follows:

```
human β2-microglobulin: sense,
                                            (SEQ ID NO: 1)
5'ACCCCCACTGAAAAAGATGA3', and anti-sense,
                                            (SEQ ID NO: 2)
5'ATCTTCAAACCTCCATGATG3',
```

-continued at 54° C.;

CD34: sense,
5'CTCTTCTGTCCAGTCACAGACC3', and (SEQ ID NO: 3)

anti-sense,
5'GAATAGCTCTGGTGGCTTGCAA3', (SEQ ID NO: 4)
at 64° C.;

CD10: sense,
5'CTGTGACAATGATCGCACTCTATG3', and (SEQ ID NO: 5)

anti-sense,
5'GATTCCAGTGCATTCATAGTAATCTC3', (SEQ ID NO: 6)
at 65° C.;

λ-like: sense,
5'ATGCATGCGGCCGCGGCATGTGTTTGGCAGC3', and (SEQ ID NO: 7)

anti-sense,
5'ATCCGCGGCCGCATCGATAGGTCACCGTCAAGATT3', (SEQ ID NO: 8)
at 67° C.;

Pax-5: sense,
5'AGCAGGACAGGACATGGAGGA3', and (SEQ ID NO: 9)

anti-sense
5'ATCCTGTTGATGGAACTGACGC3', (SEQ ID NO: 10)
at 64° C.;

CD19: sense,
5'TCACCGTGGCAACCTGACCATG3', and (SEQ ID NO: 11)
anti-sense
5'GAGACAGCACGTTCCCGTTACTG3', (SEQ ID NO: 12)
at 67° C.;

VHconsensus-Cμ: sense,
5'GACACGGCCGTGTATTACTG3', and (SEQ ID NO: 13)

anti-sense,
5'ATCCGCGGCCGCGGAATTCTCACACAGGAGAC-GA3', (SEQ ID NO: 14)
at 60° C.;

Vκconsensus: sense,
5*ATGACCCAGTCTCCATCCTCCCTG3*, and (SEQ ID NO: 15)

-continued anti-sense
5'ATGCGGCCGCGGGAAGATGAAGACAGATG3', (SEQ ID NO: 16)
at 67° C.

Figure 26:
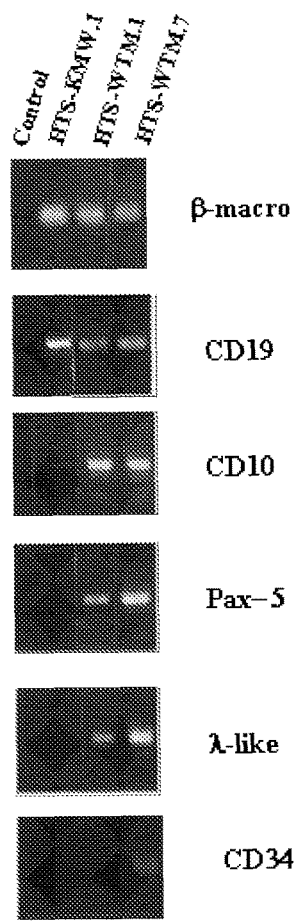
FIG. 26. RT-PCR transcripts for early B cell development markers in HTS-WTM cultures 1 and 7 initiated from 100% homogeneous culture of CD19+ cells and showing signs of de-differentiation when compared to HTS-KMW.1. The presence of Pax-5 and λ-like transcripts alone with up-regulation of CD10 in both HTS-WTM and an appearance of CD34 in HTS-WTM.7 indicates de-differentiation of mature B cells into B cells of earlier stages in response to change environmental conditions.

FIG. 26 shows that HTS-WTM cultures indeed showed expression of transcripts for early B cell development such as Pax-5 and λ-like when compared to HTS-KMW.1 cultures which did not contain such transcripts. In addition, CD34 is also being transcribed in HTS-WTM.7 cultures. This result strongly indicates de-differentiation of mature CD19+ cells into early stage B cells in response to changed environmental conditions.

EXAMPLE 7

7. Dedifferentiation of Mature Cells of Different Phenotypes Derived from HTS Cells Via Somatic Cell Hybridization To further demonstrate plasticity of HTS, the phenotypically distinct subpopulations derived from various HTS cultures were subjected to de-differentiation via somatic hybridization with primary hematopoietic stem cells. The CD34+ bone marrow stem cells were selected as described in Section 1.2.2. Essentially, the same protocol for somatic cell hybridization was used as described in Section 3.1.2.

7.1 De-Differentiation of B Cells Trans-Differentiated from HTS Cultures

B cells derived from the cultures of $KBT^{AE}.6$ and KMW.5 grown in B lymphoid promoting environment were used in this particular example. The cultures were selected for their purity as 100% of all the cells in both cultures were positive for CD19+. The marker expression profile of these HTS cultures after exposure to B lymphoid promoting environment is summarised in Table 5 (see Section 4.3.1.1). KMW.5 represents a case where all the three cells used to create HTS had immortal phenotype, whereas $KBT^{AE}.6$ was derived from immortal myeloid progenitor and primary B and T lymphocytes. After hybridisation with CD34+ stem cell derived from bone marrow, the HTS cultures were grown in standard culture medium supplemented with human IL-6 at 20 ng/ml, human SCF at 300 ng/ml, human fms-like tyrosine kinase 3 ligand (hFLT3L) at 100 ng/ml, human thrombopoietin (hTPO) at 20 ng/ml, and human IL-3 at 60 ng/ml. After I month in the culture, the cell populations were analysed for expression of B lymphocyte associated markers described in Section 4.3.1.1, as well as CD34 and CD130. The cells were labelled with the same mouse antibodies as described in Section 1.2.2 as well as mouse anti-human CD34-PE and mouse anti-human CD130-FITC using the same protocol as described for the isolation of CD34+ cells from bone marrow (see Section 1.2). Table 9 summarises a CD profile of cells after de-differentiation initiation.

TABLE 9

Phenotypic profile of the cells de-differentiated from B lymphocytes derived from HTS cultures (%)

| HTS culture | CD34+ | CD38+ | CD130+ | CD19+ | CD1c+ | CD10+ | CD20+ | CD22+ | CD40+ | IgM | IgG |
|---|---|---|---|---|---|---|---|---|---|---|---|
| KMW.5 | 95 | 100 | 100 | 10 | 11 | 83 | 0 | 0 | 0 | 8 | 0 |
| $KBT^{AE}.6$ | 67 | 100 | 100 | 30 | 29 | 54 | 0 | 0 | 0 | 24 | 0 |

In both cultures vast majority of cells lost its landmark markers of B cell lineage such as surface Ig and CD19, whilst up-regulating CD10 expression and acquiring CD34.

7.2 De-Differentiation of CD4+ T Cells Trans-Differentiated from HTS Cultures

CD4+ T cells derived from the culture of KMW.6 grown in a T lymphoid promoting environment were used in this particular example. The cultures were selected for their purity as 100% of all the cells being positive for CD4+. The marker expression profile of these HTS culture after exposure to T lymphoid promoting environment is summarised in Table 2 (see Section 4.1.1.1). After hybridisation with CD34+ stem cell derived from bone marrow, the HTS cultures were grown in standard culture medium supplemented with various cytokines promoting growth of hematopoietic stem cells (HSC) (see Section 7.1). After 1 month in the HSC environment, the cells were analysed for the expression of CD4+ T cells associated markers described in Section 4.1.1.1 as well as CD34 and CD130. Table 10 below shows a profile of CD expression on the surface of dedifferentiated CD4+ cells.

TABLE 10

Phenotypic profile of dedifferentiated CD4+ T cells derived from HTS cultures (%)

| HTS culture | CD34+ | CD38+ | CD130+ | CD4+ | TCRαβ | CD25 | CD27 | CD28 | CD62L | CD69 | CD95 | CD45 |
|---|---|---|---|---|---|---|---|---|---|---|---|---|
| KMW.6 | 92 | 100 | 100 | 10 | 8 | 63 | 0 | 0 | 0 | 0 | 0 | $100^{low}$ |

The vast majority of the cells lost expression of CD4 and TCR whilst up-regulating expression of CD25 and acquiring expression of CD34.

7.3 De-Differentiation of CD8+ T Cells Trans-Differentiated from HTS Cultures

CD8+ T cells derived from the culture of $KBT^{DP}.12$ grown in T lymphoid promoting environment were used in this particular example. The cultures were selected for their purity as 100% of all the cells being positive for CD8+. The marker expression profile of these HTS culture after exposure to T lymphoid promoting environment is summarised in Table 4 (see Section 4.2.1.1). After hybridisation with CD34+ stem cell derived from bone marrow, the HTS culture were grown in standard culture medium supplemented with various cytokines promoting growth of hematopoietic stem cells (HSC) (see Section 7.1). After 1 month in the HSC environment, the cells were analysed for the expression of CD8+ T cells associated markers described in Section 4.2.1.1 as well as CD34 and CD130. Table 11 below shows profile of CD expression on the surface of dedifferentiated CD8+ cells.

TABLE 11

Phenotypic profile of dedifferentiated CD8+ T cells derived from HTS cultures (%)

| HTS culture | CD34+ | CD38+ | CD130+ | CD8+ | TCRαβ | CD27 | CD28 | CD62L | CD95 | CD45 | CD8α | CD8β |
|---|---|---|---|---|---|---|---|---|---|---|---|---|
| $KBT^{DP}.12$ | 97 | 100 | 100 | <1 | <1 | 0 | 0 | 0 | 0 | $100^{low}$ | <1 | <1 |

Almost all the cells lost their CD8 and TCR expression whilst acquiring expression of CD34.

Although the invention has been described with reference to specific examples, it will be appreciated by those skilled in the art that the invention may be embodied in many other forms, in keeping with the broad principles and the spirit of the invention described herein.

REFERENCES

Beug et al, Genes Dev 1:277-286, 1987
Borzello et al, Mol. Cell. Biol. 10:2703-2714, 1990
Boyd et al, Nature 297:691-693, 1982
DeKoter et al, Science 288: 146-149, 2000
Frampton et al, EMBO J. 14: 2866-2875, 1995
Golay et al, Cell 55: 1147-1158, 1987;
Graf et al Cell 70:201-213, 1992;
Graf et at, Blood 99: 3089-3101, 2002.
Jackson et al, J. Clin. Invest. 107: 1395-1402, 2001
Kee et al, Curr. Opin. Immunol. 13: 180-185, 2001
Kee et al, J. Exp. Med. 188: 699-713, 1998
Klinken et al, Cell 53: 857-867, 1988
Klinken et al, Cell 53: 857-867, 1988
Kohler and Milstein, C. Nature, 256, 495-497, 1975
Kondo et al, Nature 407: 383-386, 2000
Krause et al, Cell 105: 369-377, 2001
Kulessa et al, Genes Dev. 9: 1250-1262, 1995
Lagasse et al, Nature Med. 6: 1229-1234, 2000
Lee et al, J. Immunol. 166: 5964-5989, 2001
Lindeman et al, Immunity 1: 517-527, 1994
Mahaworasilpa, Cell Electro-Dynamics: The mechanics of living cells in intense alternating electric fields. PhD Thesis, University of New South Wales, Sydney, Australia, 1992
Mahaworasilpa et al, Biochim. Biophys. Acta. 1193:118-126, 1994
McIlroy et al, J. Virol. 69:4737-4745, 1995
McNagny et al, J. Cell. Biol. 138:1395-14-7, 1997
Montecino-Rodriguez et al, Nat. Immunol. 2: 83-88, 2001
Neil, and Zimmermann, U Electro, Meth. Enzymol 220, 174, 1993
Nutt et al, Nature 401: 556-562, 1999
Orkin, Nature Rev. Genet.1: 57-64, 2000
Orlic et al, Ann. NY Acad. Sci. 938:221-230, 2001
Orlic et al, Nature 410: 701-705, 2001
Pohl, Dielectrophoresis, Cambridge University Press, London 1978
Rolink et al, Nature 401:556-562, 1999
Romanow et al, Mol. Cell. 5: 343-353, 2000
Rossi et al, Curr. Biol. 6: 866-872, 1988
Rossi et al, EMBO J. 15: 1894-1901, 1996
Sokolovsky M et al, Proc Natl. Acad. Sci. USA 95: 6573-6575, 1998
Stoffel et al, Proc Natl. Acad. Sci. USA 96: 698-702, 1999
Wojciersyn et al, J. Cell. Biol. 96: 151-159, 1983
Zimmermann, Biochim. Biophys. Acta. 694: 227-277, 1982

The invention claimed is:

1. A method of generating CD8+ T-cell from a tri-hybrid cell, said method comprising the steps of
   (i) hybridizing a first, a second and a third cell to produce a tri-hybrid cell that exhibits genetic stability, phenotypic plasticity and cellular markers of said first, second and third cell, wherein a myeloma cell is not included in the hybridization, wherein the first cell is an immortalized myeloid cell, wherein the second cell is selected from the group consisting of a CD19+ mature B cells, a CD20−CD72+ early B cells, a CD20+CD72+ activated B cells and a CD19−CD5+ antigen experienced B cells, and wherein the third cell is selected from group consisting of a CD4+ helper T cell, a CD3+CD5+ antigen-experienced T cells, CD3+ T cell and a CD4+CD8+ T cells;
   (ii) determining cellular markers of said first, second and third cell in the tri-hybrid cell to establish the presence in the genetically stable tri-hybrid cell of all the cellular markers of said first, second and third cell; and
   (iii) culturing said genetically stable tri-hybrid cell with human thymic stromal cells to produce a CD8 expressing T-cell.

2. The method according to claim 1, wherein said first cell is a K562 cell.

3. The method according to claim 1, wherein said second cell is a WIL2NS cell and said third cell is a MOLT4cell.

4. The method according to claim 1, wherein said second cell is a WIL2NS cell.

5. The method according to claim 1, wherein said third cell is a MOLT4cell.

6. The method according to claim 1, wherein said first cell is a K562cell, said second cell is a WIL2NS cell and said third cell is a MOLT4 cell.

7. The method according to claim 1, wherein said first cell is a K562cell, said second cell is a primary B cell and said third cell is a primary T cell.

* * * * *